US012589073B2

(12) United States Patent
Peruzzi et al.

(10) Patent No.: US 12,589,073 B2
(45) Date of Patent: Mar. 31, 2026

(54) LEVERAGING LIPID-PROTEIN INTERACTIONS TO ENGINEER SPATIAL ORGANIZATION IN CELL-FREE SYSTEMS

(71) Applicant: Northwestern University, Evanston, IL (US)

(72) Inventors: Justin Alexander Peruzzi, Evanston, IL (US); Neha Prashant Kamat, Evanston, IL (US); Jan Steinkuehler, Evanston, IL (US)

(73) Assignee: Northwestern University, Evanston, IL (US)

( * ) Notice: Subject to any disclaimer, the term of this patent is extended or adjusted under 35 U.S.C. 154(b) by 591 days.

(21) Appl. No.: 18/054,131

(22) Filed: Nov. 9, 2022

(65) Prior Publication Data

US 2023/0277456 A1 Sep. 7, 2023

Related U.S. Application Data

(60) Provisional application No. 63/376,979, filed on Sep. 23, 2022, provisional application No. 63/278,442, filed on Nov. 11, 2021.

(51) Int. Cl.
*A61K 9/1271* (2025.01)
*A61K 9/1275* (2025.01)
*A61K 9/1278* (2025.01)

(52) U.S. Cl.
CPC .......... *A61K 9/1271* (2013.01); *A61K 9/1275* (2013.01); *A61K 9/1278* (2013.01)

(58) Field of Classification Search
None
See application file for complete search history.

(56) References Cited

U.S. PATENT DOCUMENTS

| | | | |
|---|---|---|---|
| 8,735,096 B2 | 5/2014 | Zhou et al. | |
| 11,028,383 B2 | 6/2021 | King et al. | |
| 2010/0189774 A1* | 7/2010 | Lenormand | ............ A61K 47/62 |
| | | | 530/350 |

FOREIGN PATENT DOCUMENTS

WO WO-2020077007 A1 * 4/2020 .............. A61P 25/16

OTHER PUBLICATIONS

Taehoon Kim Kyu Il Lee, Phillip Morris, Richard W. Pastor, Olaf S. Andersen, and Wonpil Im. "Influence of Hydrophobic Mismatch on Structures and Dynamics of Gramicidin A and Lipid Bilayers." Biophysical Journal, vol. 102, Apr. 2012, pp. 1551-1560. (Year: 2012).*

Armando J. de Jesus, Toby W. Allen. "The determinants of hydrophobic mismatch response for transmembrane helices." Biochimica et Biophysica Acta, vol. 1828, 2013, pp. 851-863. (Year: 2013).*

Taehoon Kim Kyu Il Lee, Phillip Morris, Richard W. Pastor, Olaf S. Andersen, and Wonpil Im. "Influence of Hydrophobic Mismatch on Structures and Dynamics of Gramicidin A and Lipid Bilayers." Biophysical Journal, vol. 102, Apr. 2012, pp. 1551-1560 and S1-S19. (Year: 2012).*

(Continued)

*Primary Examiner* — Isaac Shomer

(74) *Attorney, Agent, or Firm* — Quarles & Brady LLP

(57) ABSTRACT

The present disclosure provides methods and compositions for controlling the localization of proteins in lipid structures. The disclosure also provides methods for selecting appropriate proteins for desired localization and distribution in lipid structures based on hydrophobic thickness.

14 Claims, 24 Drawing Sheets

Specification includes a Sequence Listing.

(56)          References Cited

OTHER PUBLICATIONS

Hermann-Josef Kaiser et al. "Lateral sorting in model membranes by cholesterol-mediated hydrophobic matching." Proceedings of the National Academy of Sciences, vol. 108, No. 40, Oct. 4, 2011, pp. 16628-16633 and 8 supplemental pages. (Year: 2011).*

J.N. Israelachvili, S. Marcelja, and R.G. Horn. "Physical principles of membrane organization." Quarterly Reviews of Biophysics, vol. 13(2), 1980, pp. 121-200. (Year: 1980).*

Dov Lichtenberg, Hasna Ahyayauch, Alicia Alonso, and Felix M. Goni. "Detergent solubilization of lipid bilayers: a balance of driving forces." Trends in Biochemical Sciences, vol. 38(2), Feb. 2013, pp. 85-93. (Year: 2013).*

Michael A. White, Kathleen M. Clark, Elizabeth J. Grayhack and Mark E. Dumont. "Characteristics Affecting Expression and Solubilization of Yeast Membrane Proteins." Journal of Molecular Biology, vol. 365, 2007, pp. 621-636. (Year: 2007).*

P. Lujan, F. Campelo, Should I stay or should I go? Golgi membrane spatial organization for protein sorting and retention. Archives of Biochemistry and Biophysics. 707, 108921 (2021).

Y. Guo, D. W. Sirkis, R. Schekman, Protein Sorting at the trans-Golgi Network. http://dx.doi.org/10.1146/annurev-cellbio-100913-013012. 30, 169-206 (2014).

S. Rodriguez-Gallardo, K. Kurokawa, S. Sabido-Bozo, A. Cortes-Gomez, A. Ikeda, V. Zoni, A. Aguilera-Romero, A. M. Perez-Linero, S. Lopez, M. Waga, M. Araki, M. Nakano, H. Riezman, K. Funato, S. Vanni, A. Nakano, M. Muñiz, Ceramide chain length-dependent protein sorting into selective endoplasmic reticulum exit sites. Science Advances. 6, 8237-8248 (2020).

R. Prasad, A. Sliwa-gonzalez, Y. Barral, Mapping bilayer thickness in the ER membrane (2020).

H. J. Sharpe, T. J. Stevens, S. Munro, A Comprehensive Comparison of Transmembrane Domains Reveals Organelle-Specific Properties. Cell. 142, 158 (2010).

J. H. Lorent, K. R. Levental, L. Ganesan, G. Rivera-Longsworth, E. Sezgin, M. Doktorova, E. Lyman, I. Levental, Plasma membranes are asymmetric in lipid unsaturation, packing and protein shape. Nature Chemical Biology 2020 16:6. 16, 644-652 (2020).

J. H. Lorent, B. Diaz-Rohrer, X. Lin, K. Spring, A. A. Gorfe, K. R. Levental, I. Levental, Structural determinants and functional consequences of protein affinity for membrane rafts. Nature Communications. 8, 1-10 (2017).

T. Harayama, H. Riezman, Understanding the diversity of membrane lipid composition. Nature Reviews Molecular Cell Biology 2018 19:5. 19, 281-296 (2018).

K. A. Schwarz, N. M. Daringer, T. B. Dolberg, J. N. Leonard, Rewiring human cellular input-output using modular extracellular sensors. Nature Chemical Biology 2016 13:2. 13, 202-209 (2016).

C. Y. Wu, K. T. Roybal, E. M. Puchner, J. Onuffer, W. A. Lim, Remote control of therapeutic T cells through a small molecule-gated chimeric receptor. Science (1979). 350 (2015), doi:10.1126/SCIENCE.AAB4077/SUPPL_FILE/WU.SM.PDF.

J. G. Rurik, I. Tombácz, A. Yadegari, P. O. Méndez Fernández, S. v. Shewale, L. Li, T. Kimura, O. Y. Soliman, T. E. Papp, Y. K. Tam, B. L. Mui, S. M. Albelda, E. Puré, C. H. June, H. Aghajanian, D. Weissman, H. Parhiz, J. A. Epstein, CAR T cells produced in vivo to treat cardiac injury. Science (1979). 375, 91-96 (2022).

Y. Lin, J. Wu, W. Gu, Y. Huang, Z. Tong, L. Huang, J. Tan, Y. Lin, J. Wu, W. Gu, J. Tan, Y. Huang, Z. Tong, L. Huang, Exosome-Liposome Hybrid Nanoparticles Deliver CRISPR/Cas9 System in MSCs. Advanced Science. 5, 1700611 (2018).

T. Q. Vu, J. A. Peruzzi, L. E. Sant'Anna, E. W. Roth, N. P. Kamat, Lipid phase separation in vesicles enhances TRAIL-mediated cytotoxicity, Nano Letters, doi:10.1021/ACS.NANOLETT.1C04365 (2022).

Z. jie Yang, Z. yan Yu, Y. ming Cai, R. rong Du, L. Cai, Engineering of an enhanced synthetic Notch receptor by reducing ligand-independent activation. Communications Biology 2020 3:1. 3, 1-7 (2020).

P. Lu, D. Min, F. DiMaio, K. Y. Wei, M. D. Vahey, S. E. Boyken, Z. Chen, J. A. Fallas, G. Ueda, W. Sheffler, V. K. Mulligan, W. Xu, J. U. Bowie, D. Baker, Accurate computational design of multipass transmembrane proteins. Science (1979). 359, 1042-1046 (2018).

C. Xu, P. Lu, T. M. Gamal El-Din, X. Y. Pei, M. C. Johnson, A. Uyeda, M. J. Bick, Q. Xu, D. Jiang, H. Bai, G. Reggiano, Y. Hsia, T. J. Brunette, J. Dou, D. Ma, E. M. Lynch, S. E. Boyken, P. S. Huang, L. Stewart, F. DiMaio, J. M. Kollman, B. F. Luisi, T. Matsuura, W. A. Catterall, D. Baker, Computational design of transmembrane pores. Nature 2020 585:7823. 585, 129-134 (2020).

F. A. Heberle, M. Doktorova, H. L. Scott, A. D. Skinkle, M. N. Waxham, I. Levental, Direct label-free imaging of nanodomains in biomimetic and biological membranes by cryogenic electron microscopy. Proc Natl Acad Sci U S A. 117, 19943-19952 (2020).

M. L. Jacobs, M. A. Boyd, N. P. Kamat, Diblock copolymers enhance folding of a mechanosensitive membrane protein during cell-free expression. Proc Natl Acad Sci U S A. 116, 4031-4036 (2019).

G. S. Waldo, B. M. Standish, J. Berendzen, T. C. Terwilliger, Rapid protein-folding assay using green fluorescent protein. Nature Biotechnology 1999 17:7. 17, 691-695 (1999).

A .. D. Silverman, N. Kelley-Loughnane, J. B. Lucks, M. C. Jewett, Deconstructing Cell-Free Extract Preparation for in Vitro Activation of Transcriptional Genetic Circuitry. ACS Synthetic Biology. 8, 403-414 (2019).

C. E. Hilburger, M. L. Jacobs, K. R. Lewis, J. A. Peruzzi, N. P. Kamat, Controlling Secretion in Artificial Cells with a Membrane and Gate. ACS Synthetic Biology. 8 (2019), doi:10.1021/acssynbio.8b00435.

E. Sezgin, I. Levental, S. Mayor, C. Eggeling, The mystery of membrane organization: composition, regulation and roles of lipid rafts. Nature Reviews Molecular Cell Biology. 18, 361-374 (2017).

H. J. Kaiser, A. Orłowski, T. Róg, T. K. M. Nyholm, W. Chai, T. Feizi, D. Lingwood, I. Vattulainen, K. Simons, Lateral sorting in model membranes by cholesterol-mediated hydrophobic matching. Proc Natl Acad Sci U S A (2011), doi:10.1073/pnas.1103742108.

Q. Lin, E. London, Altering hydrophobic sequence lengths shows that hydrophobic mismatch controls affinity for ordered lipid domains (rafts) in the multitransmembrane strand protein perfringolysin O. Journal of Biological Chemistry. 288, 1340-1352 (2013).

J. P. Schlebach, P. J. Barrett, C. A. Day, J. H. Kim, A. K. Kenworthy, C. R. Sanders, Topologically Diverse Human Membrane Proteins Partition to Liquid-Disordered Domains in Phase-Separated Lipid Vesicles. Biochemistry. 55, 985-988 (2016).

L. v. Schäfer, D. H. de Jong, A. Holt, A. J. Rzepiela, A. H. de Vries, B. Poolman, J. A. Killian, S. J. Marrink, Lipid packing drives the segregation of transmembrane helices into disordered lipid domains in model membranes. Proc Natl Acad Sci U S A. 108, 1343-1348 (2011).

D. Lingwood, J. Ries, P. Schwille, K. Simons, Plasma membranes are poised for activation of raft phase coalescence at physiological temperature. Proceedings of the National Academy of Sciences. 105, 10005-10010 (2008).

B. Sorre, A. Callan-Jones, J. B. Manneville, P. Nassoy, J. F. Joanny, J. Prost, B. Goud, P. Bassereau, Curvature-driven lipid sorting needs proximity to a demixing point and is aided by proteins. Proceedings of the National Academy of Sciences. 106, 5622-5626 (2009).

S. Katira, K. K. Mandadapu, S. Vaikuntanathan, B. Smit, D. Chandler, Pre-transition effects mediate forces of assembly between transmembrane proteins. Elife. 5 (2016), doi:10.7554/eLife.13150.

J. Steinkühler, P. Fonda, T. Bhatia, Z. Zhao, F. S. C. Leomil, R. Lipowsky, R. Dimova, Superelasticity of Plasma- and Synthetic Membranes Resulting from Coupling of Membrane Asymmetry, Curvature, and Lipid Sorting. Advanced Science. 8, 2102109 (2021).

S. L. Veatch, S. L. Keller, Separation of Liquid Phases in Giant Vesicles of Ternary Mixtures of Phospholipids and Cholesterol. Biophysical Journal. 85, 3074 (2003).

J. T. Marinko, J. T. Marinko, A. K. Kenworthy, A. K. Kenworthy, C. R. Sanders, C. R. Sanders, C. R. Sanders, Peripheral myelin protein 22 preferentially partitions into ordered phase membrane domains. Proc Natl Acad Sci U S A. 117, 14168-14177 (2020).

A . . . S. Dixon, M. K. Schwinn, M. P. Hall, K. Zimmerman, P. Otto, T. H. Lubben, B. L. Butler, B. F. Binkowski, T. MacHleidt, T. A.

(56)　　　　　　References Cited

OTHER PUBLICATIONS

Kirkland, M. G. Wood, C. T. Eggers, L. P. Encell, K. v. Wood, NanoLuc Complementation Reporter Optimized for Accurate Measurement of Protein Interactions in Cells. ACS Chemical Biology. 11, 400-408 (2016).

Peruzzi et al. Hydrophobic mismatch drives self-organization of designer proteins into synthetic membranes. bioRxiv. manuscript posted Jun. 2, 2022. 34 pages.

* cited by examiner

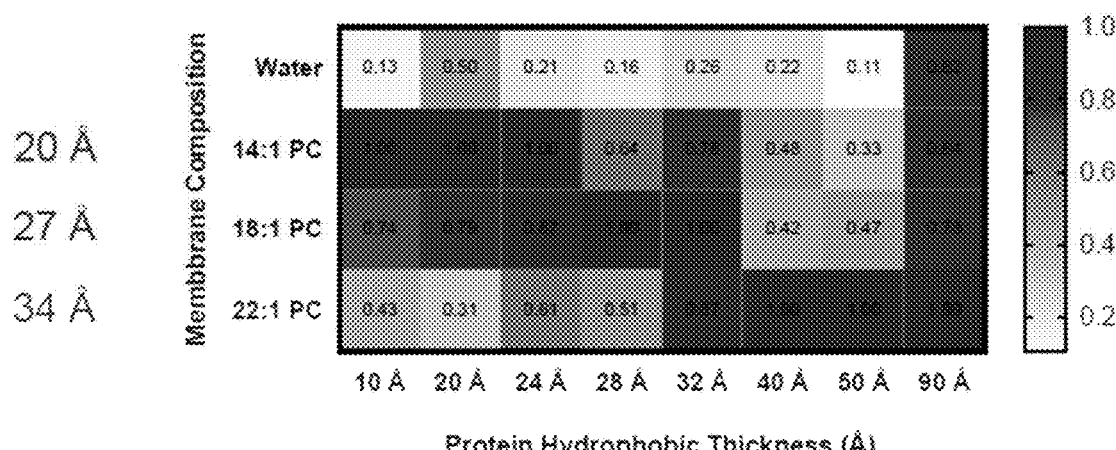
FIG. 4A
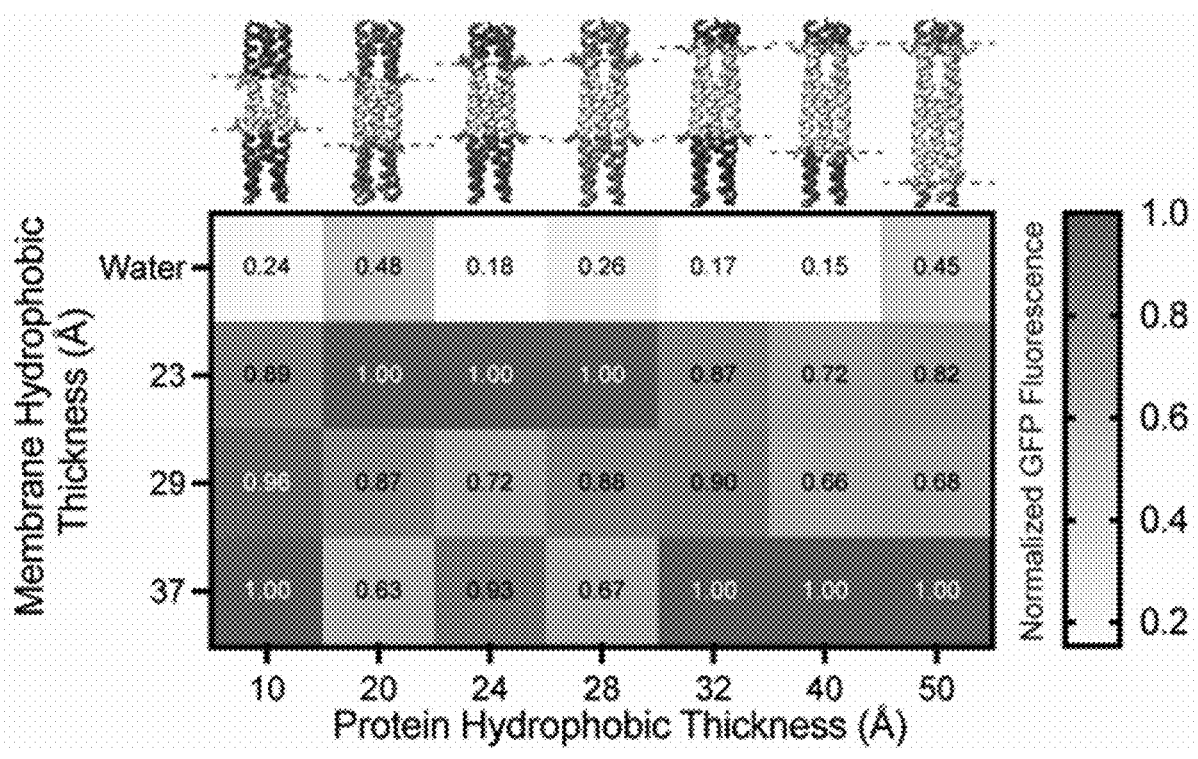
FIG. 4B

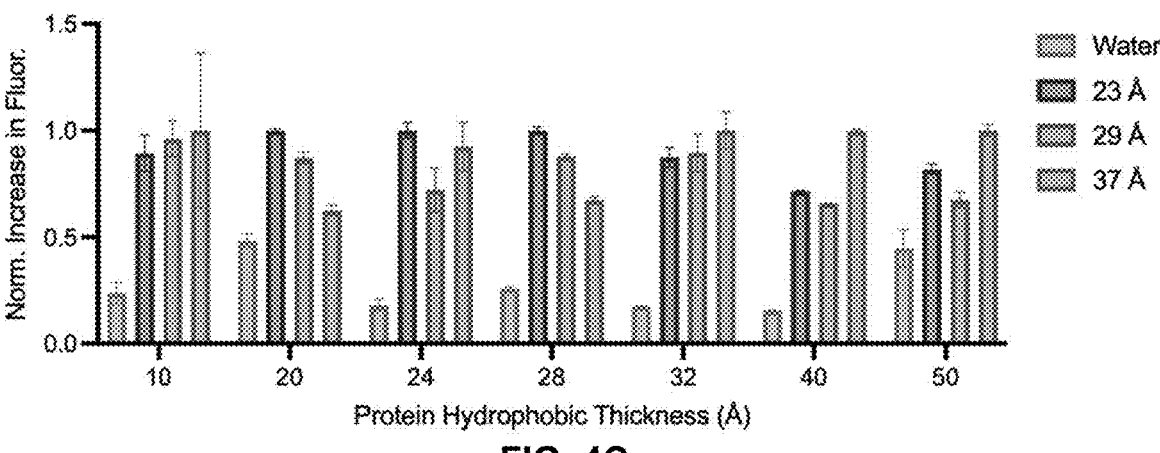
FIG. 4C
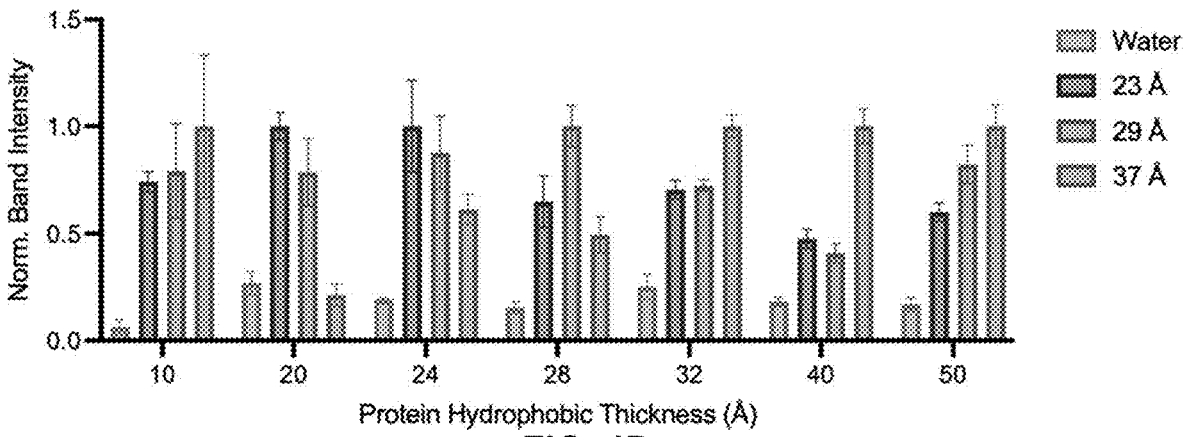
FIG. 4D
FIG. 4E

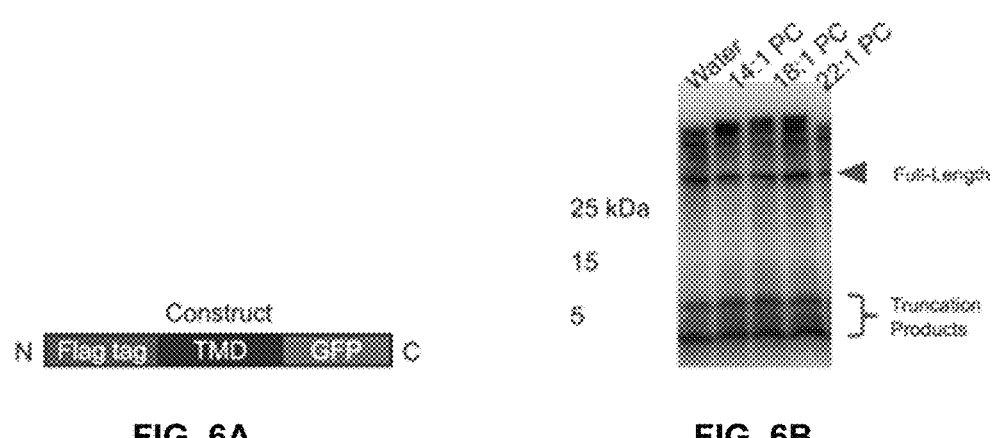
FIG. 6A                                    FIG. 6B
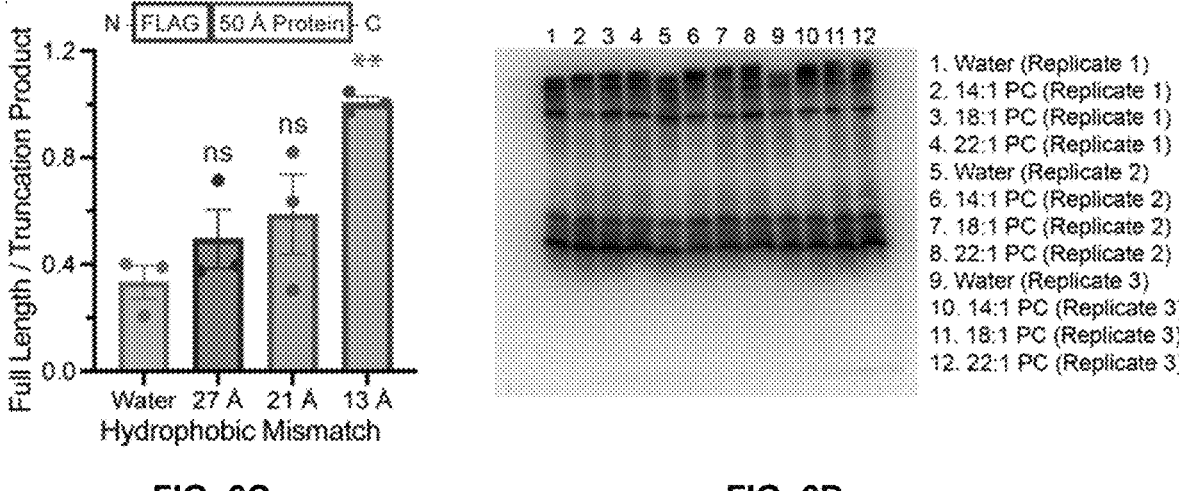
FIG. 6C                                    FIG. 6D

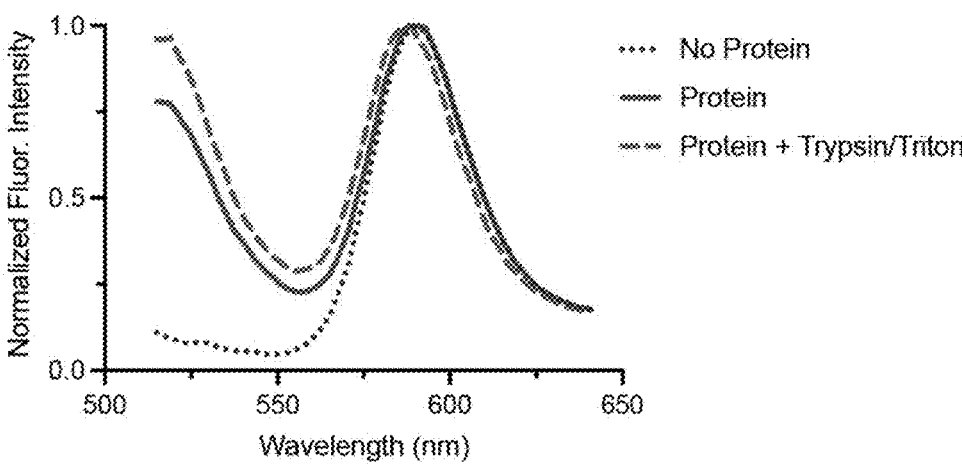
FIG. 15A
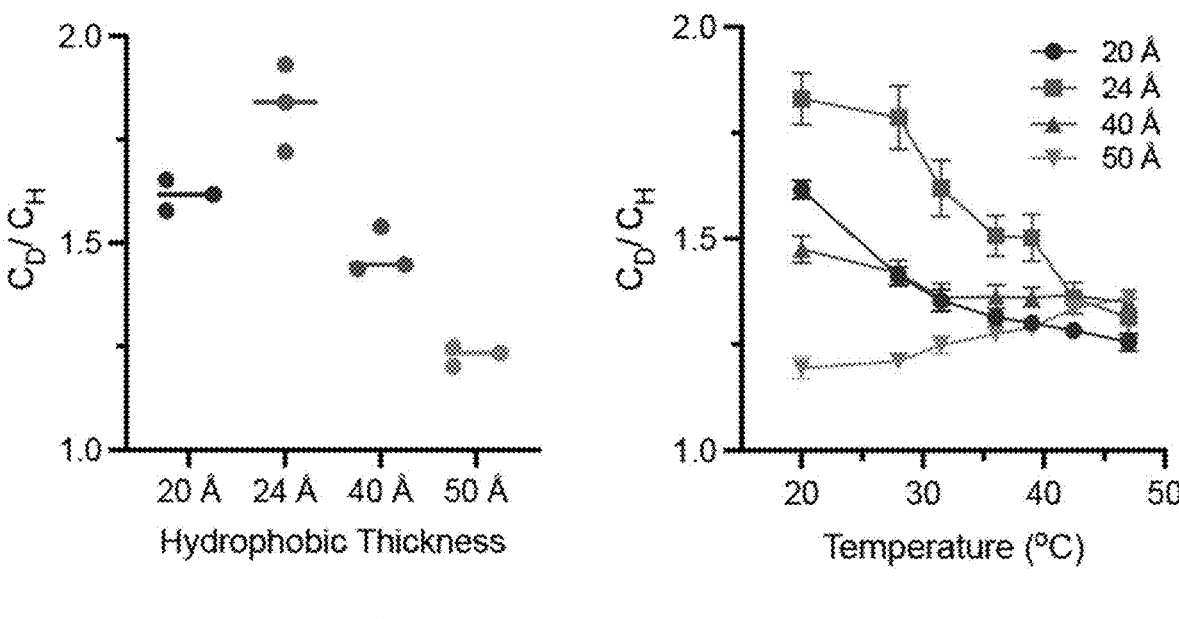
FIG. 15B                              FIG. 15C

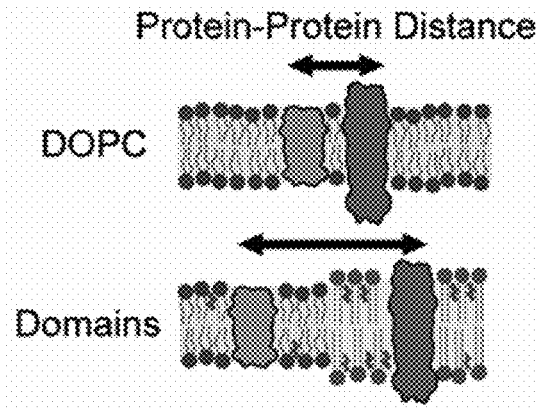
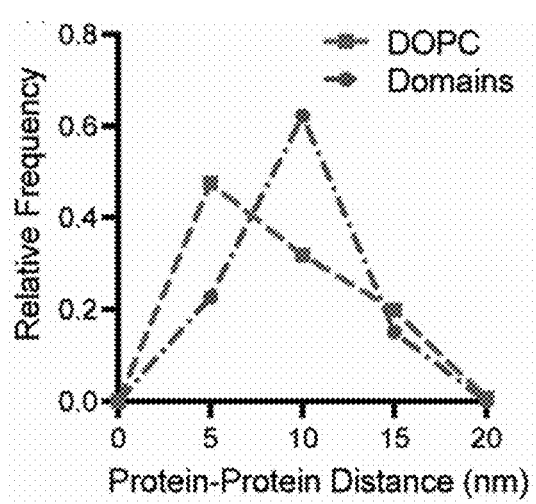
FIG. 16A
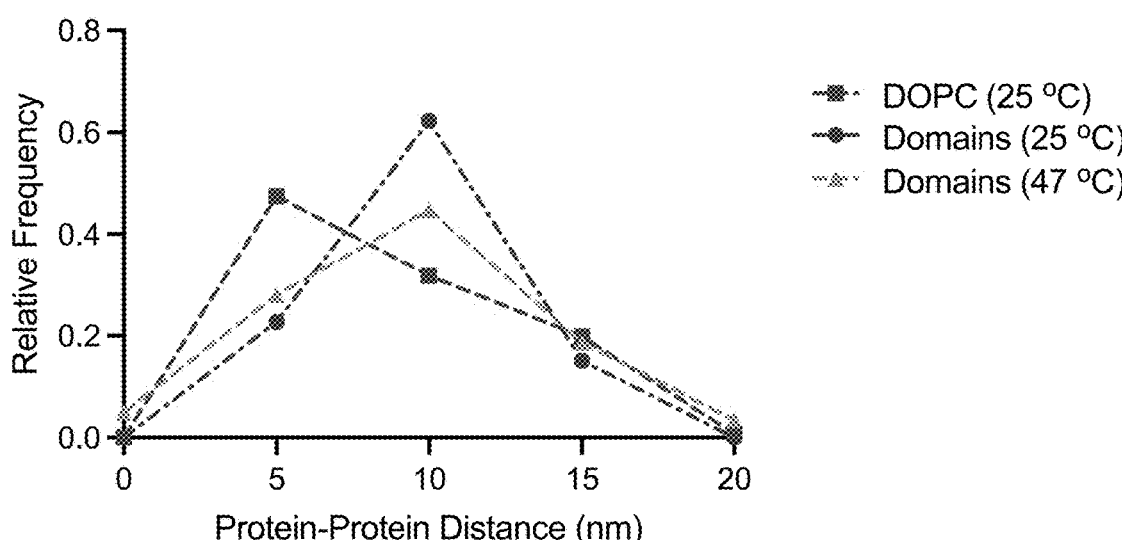
FIG. 16B

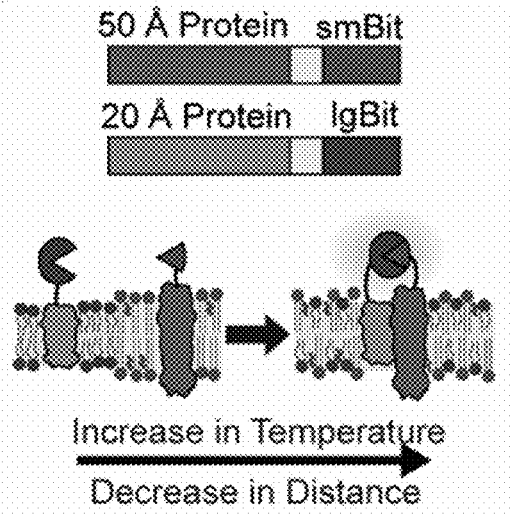
FIG. 17C
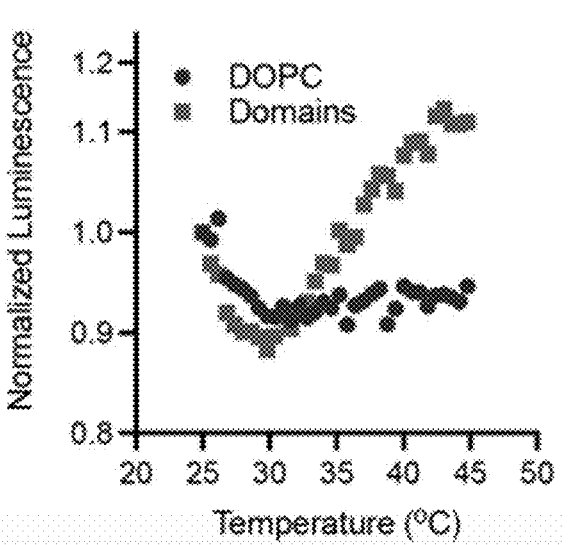
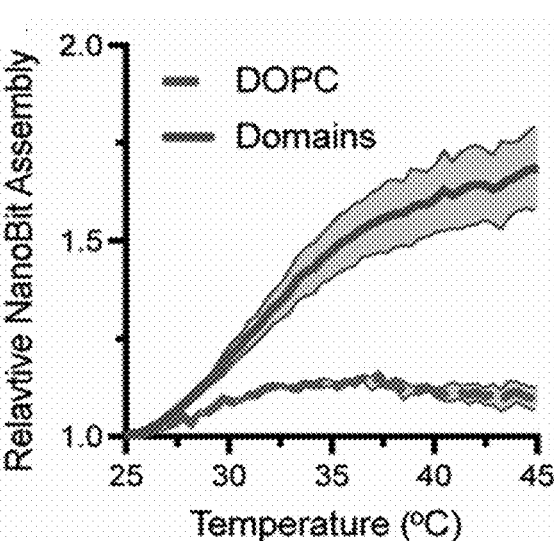
FIG. 17D

LEVERAGING LIPID-PROTEIN INTERACTIONS TO ENGINEER SPATIAL ORGANIZATION IN CELL-FREE SYSTEMS

CROSS-REFERENCE TO RELATED APPLICATIONS

This application claims priority to, and the benefit of, U.S. Application No. 63/278,442 filed Nov. 11, 2021, and U.S. Application No. 63/376,979 filed Sep. 23, 2022, the contents of which are incorporated herein by reference in their entireties.

STATEMENT REGARDING FEDERALLY SPONSORED RESEARCH OR DEVELOPMENT

This invention was made with government support under T32GM008449 awarded by the National Institutes of Health and 1844219, 1844336, 2145050, and 1935356 awarded by the National Science Foundation. The government has certain rights in the invention.

REFERENCE TO AN ELECTRONIC SEQUENCE LISTING

The contents of the electronic sequence listing (702581.02255.xml; Size: 45,753 bytes; and Date of Creation: Nov. 8, 2022) is herein incorporated by reference in its entirety.

FIELD

The field of the invention relates to methods and compositions for controlling protein localization within lipid membranes.

BACKGROUND

Biological cells leverage membrane bound compartments to perform complex functions with precise spatial and temporal control. To execute these processes, cells must insert and sort proteins into distinct membrane compartments. Cellular membranes possess a variety of mechanisms to control membrane protein location. Protein transport is largely mediated by different protein-protein interactions and protein machinery such as clathrin, COPI, and SNARE proteins (1, 2). It has also been hypothesized that lipid-protein interactions can drive inter- and intramembrane protein organization (3-5). Membranes and membrane-proteins have been shown to possess complementary physio-chemical properties, likely allowing for proper protein sorting and function within cells (5-7). Specifically, protein transmembrane domain length and geometry have been shown to correlate with protein localization between and within different cellular membranes (6, 7). These studies suggest that physical features of membranes and proteins, such as the hydrophobic thickness of transmembrane domains and lipid bilayers, are used by cells to organize membrane proteins into distinct organelle membranes, thereby controlling membrane-based behaviors.

A major challenge to probing the contribution of physical factors in membrane protein folding and sorting is the complexity of biological cells. Cells possess a diverse lipidome, unique protein structures, and complex protein sorting machinery, making it difficult to parse out the extent to which specific lipid-protein biophysical interactions influence membrane protein folding and trafficking (2, 8). Recent advances in de novo protein design and membrane-augmented cell-free protein synthesis systems offer a route to explore how protein and lipid properties affect membrane protein integration and dynamics in a controlled environment. Developing in vitro methods to characterize specific membrane-protein interactions, such as those influenced by membrane physical properties or protein sequence and structure is of interest. Advancement in this area will shed light on fundamental biological questions surrounding protein folding and sorting. In addition, this insight will enable the design of membrane-based materials (e.g. biosensors, drug delivery vehicles) with properties beyond what is possible in nature (9-14), critical in advancing applications in biosensing and therapeutics.

SUMMARY

The present disclosure provides methods for controlling the localization and distribution of proteins within lipid membranes. In an embodiment, the method comprises providing a first protein, the first protein having a first hydrophobic thickness; providing a lipid structure comprising a lipid bilayer, the lipid bilayer comprising a first domain having a second hydrophobic thickness; and combining the first protein and the lipid structure under conditions that promote integration of the first protein into the first domain of the lipid bilayer, wherein the first protein traverses the lipid bilayer, and wherein the first hydrophobic thickness and the second hydrophobic thickness have a difference of no greater than about 5 angstroms.

In an aspect, the step of providing the first protein comprises synthesizing the first protein using a cell-free system. In an aspect, the step of providing the first protein, providing the lipid structure, and combining the first protein and the lipid structure are performed simultaneously. In an aspect, the first protein is an isolated protein. In an aspect, the first protein is a pore protein.

In another aspect, the lipid structure is a synthetic vesicle. In an aspect, prior to providing the synthetic vesicle the method further comprises preparing the vesicle with cholesterol and one or more phosphatidylcholines. In an aspect, the lipid structure is a cell or an organelle. In an aspect, lipid structure is a lipid nanoparticle.

In another aspect, the first hydrophobic thickness is between about 20 and about 40 angstroms.

In an aspect, the method further comprises incubating the lipid structure with a molecule after the first protein integrates into the lipid bilayer. In an aspect, the molecule is selected from an analyte and a drug.

In an aspect, the lipid bilayer comprises a second domain having a third hydrophobic thickness, wherein the method further comprises providing a second protein having a fourth hydrophobic thickness, wherein the second hydrophobic difference and the third hydrophobic thickness have a difference of greater than about 5 angstroms, and wherein the third hydrophobic thickness and the fourth hydrophobic thickness have a difference of no greater than about 5 angstroms.

In another embodiment, provided are methods for organizing two or more proteins within a lipid bilayer having two or more domains, comprising providing the two or more proteins, each protein has a protein hydrophobic thickness, and wherein each protein hydrophobic thickness has a difference of greater than about 5 angstroms; providing a lipid structure comprising the lipid bilayer, wherein each of the two or more domains has a bilayer hydrophobic thickness, and wherein each bilayer hydrophobic thickness has a difference of greater than about 5 angstroms; combining the proteins and the lipid structure under conditions that promote integration of the proteins into the lipid bilayer, wherein the proteins traverse the lipid bilayer, and wherein each protein thickness is no greater than 5 angstroms different than the bilayer hydrophobic thickness of one of the two or more domains.

In an aspect, the step of combining the proteins and the lipid structure is performed at a temperature of between about 20 and about 37° C. In an aspect, the method further comprises increasing the temperature to between about 37 and about 80° C. after the proteins are integrated into the lipid bilayer.

In an aspect, the step of providing the proteins, providing the lipid structure, and combining the proteins and the lipid structure are performed simultaneously. In an aspect, the step of providing the protein comprises synthesizing the protein using a cell-free system. In an aspect, the protein is an isolated protein. In an aspect, the protein is a pore protein.

In an aspect, the lipid structure is a synthetic vesicle or a lipid nanoparticle. In an aspect, prior to providing the synthetic vesicle the method further comprises preparing the vesicle with cholesterol and one or more phosphatidylcholines.

In the aspect, the lipid structure is a cell. In an aspect, the lipid structure is an organelle. In an aspect, the method further comprises incubating the lipid structure with a molecule after the protein integrates into the lipid bilayer. In an aspect, the molecule is selected from an analyte and a drug.

In another embodiment, provided herein is a composition for preparing a synthetic vesicle having a transmembrane protein comprising: the synthetic vesicle; and a cell free protein expression system for expressing the transmembrane protein, wherein the transmembrane protein has a protein hydrophobic thickness; wherein the synthetic vesicle comprises a lipid bilayer having a domain, wherein the domain has a bilayer hydrophobic thickness; wherein the protein thickness is no greater than 5 angstroms different than the bilayer hydrophobic thickness.

In an aspect, the synthetic vesicle comprises one or more phosphatidylcholines and less than 30% cholesterol. In an aspect, the synthetic vesicle further comprises a plurality of transmembrane proteins and a plurality of domains, wherein each bilayer hydrophobic thickness has a difference of greater than about 5 angstroms, and wherein each protein thickness has a difference of greater than about 5 angstroms.

In another embodiment, provided herein is a method comprising combining a selected protein-lipid domain pair, wherein the selected protein-lipid domain pair comprises a protein having a protein hydrophobic thickness matched to a lipid domain in a lipid structure.

In an aspect, the method further comprises selecting the protein for combination with the lipid domain, wherein the protein is selected to have a protein hydrophobic thickness less than 5 angstrom different than a lipid hydrophobic thickness of the lipid domain and wherein the combined protein traverses the lipid domain. In an aspect, the method further comprises selecting the lipid structure comprising the lipid domain for combination with the protein. In an aspect, combining the protein and the lipid structure comprises expressing the protein with a cell-free system and incubating the expressed protein with lipid structure.

In an aspect, the protein is expressed in the presence of the lipid structure. In an aspect, the protein is an isolated protein. In an aspect, the protein is a pore protein. In an aspect, the lipid structure is a synthetic vesicle. In an aspect, the lipid structure is a cell. In an aspect, the lipid structure is an organelle. In an aspect, the lipid hydrophobic thickness is between about 20 and about 40 angstroms.

In an embodiment, provided herein is a lipid structure prepared by the methods and compositions disclosed herein.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and description herein for interpreting the scope of the invention.

BRIEF DESCRIPTION OF THE DRAWINGS

FIG. 2A is a schematic illustrating the experimental design. FIG. 2B shows the analysis performed for a 20 Å protein. FIG. 2C shows the analysis performed for a 28 Å protein. FIG. 2D shows the analysis performed for a 50 Å protein. The horizontal dotted lines represent the hydrophobic thickness of the protein. FIG. 2E shows the datapoints derived from simulations of the 20, 28, and 50 Å proteins for three membrane compositions (thin, medium, thick).

FIGS. 4A-4E illustrate the effects of hydrophobic mismatch on protein expression. FIGS. 4A and 4B illustrate that reducing hydrophobic mismatch maximizes protein expression, as measured by increased GFP fluorescence, is maximized in hydrophobically matched membranes. Values represent the mean of 3 independent replicates, normalized to the maximum increase in fluorescence for each protein construct. FIG. 4C illustrates the effect of hydrophobic mismatch on protein expression using GFP fluorescence. Increase in GFP fluorescence was normalized to the maximum increase for each construct. n=3, error bars represent S. E. M. FIG. 4D illustrates the effect of hydrophobic mismatch on protein expression using Western blot. Protein band intensity was normalized to the most intense band for each construct. n=3, error bars represent S. E. M. FIG. 4E illustrates the correlation of increase in GFP fluorescence with membrane compression, as measured by MD simulation.

FIGS. 6A-6D. FIG. 6A illustrates a construct including an N-terminal flag tag added to the 50 Å hairpin protein for enabling the detection of all protein products. FIG. 6B shows protein formation assessed by western blot. The construct was expressed in the presence of water, 14:1 PC, 18:1 PC, and 22:1 PC. FIG. 6C illustrates a plot of the intensity of the full-length product and truncation products of FIG. 6B, measured using ImageJ. The ratio of full-length to truncation product intensity is shown. FIG. 6D shows an uncropped western blot for all replicates is displayed in FIG. 6B.

FIG. 11A illustrates expression of protein in the presence of two populations of vesicles, followed by bead capture and flow cytometry for characterization of protein organization. FIG. 11B illustrates the gating strategy for bead-based protein sorting assays were first gated on sizes (left panel) to analyze larger beads and reduce analysis of unbound vesicles, then gated by the presence of antibody (right panel). FIG. 11C illustrates the effect of increase in hydrophobic thickness of designed membranes on protein-mediated binding of membrane vesicles to beads. Vertical dotted lines correspond to membrane hydrophobic thickness. FIG. 11D is a schematic illustrating cargo delivery in vesicle populations. FIG. 11E illustrates cargo delivery to thick and thin vesicles. FIG. 11F illustrates the gating strategy for pore permeability flow data of FIG. 11D. FIG. 11G illustrates population metrics for pore permeability flow data of FIG. 11E.

FIG. 14A illustrates lipid organization detected by lipid-lipid-FRET.

FIG. 14B illustrates lipid-protein FRET between C-terminal AlexaFluor 488-SNAP tag and Rhodamine conjugated lipids. FIG. 14C illustrates association of 20 Å and 50 Å proteins with Rhodamine conjugated lipids.

FIGS. 15A-15C illustrate in vitro analysis of lipid-protein FRET and protein-lipid interactions using SNAP conjugated fluorophores. FIG. 15A illustrates spectra of SNAP conjugated proteins in a homogenous DOPC membrane. FIG. 15B illustrates $C_D/C_H$ values for long and short transmembrane domains at room temperature. FIG. 15C illustrates $C_D/C_H$ values for long and short transmembrane domains at elevated temperature.

FIGS. 16A-16B illustrate analysis of localization of different sized proteins in lipid membranes. FIG. 16A illustrates modulation of protein-protein distance by lipid composition of synthetic membranes. FIG. 16B illustrates protein-protein distance at elevated temperatures as predicted by MD simulations.

FIGS. 17A-17D illustrate analysis of protein dimerization in lipid membranes. FIG. 17A illustrates a NanoBit assembly experiment. FRB and FKBP were fused to the C-terminus of the 20 and 50 Å protein, respectively. Addition of rapamycin forced proteins to dimerize and NanoBit to become reconstituted, enabling the evaluation of protein-protein interactions. FIG. 17B illustrates luminescence due to protein dimerization. FIG. 17C illustrates a NanoBit assembly experiment in which domain formation is observed in view of temperature. FIG. 17D illustrates the NanoBit assembly as temperature increases in domain forming lipid mixtures compared to DOPC.

FIG. 18A illustrates raw luminescence data of split luciferase constructs in DOPC and domain forming membranes. FIG. 18B illustrates luminescence vs temperature for soluble NanoBit. FIG. 18C illustrates changes in luminescence in view of 20 and 50 Å protein for DOPC and domain forming membranes after normalization by the initial value.

DETAILED DESCRIPTION

Figure 1:
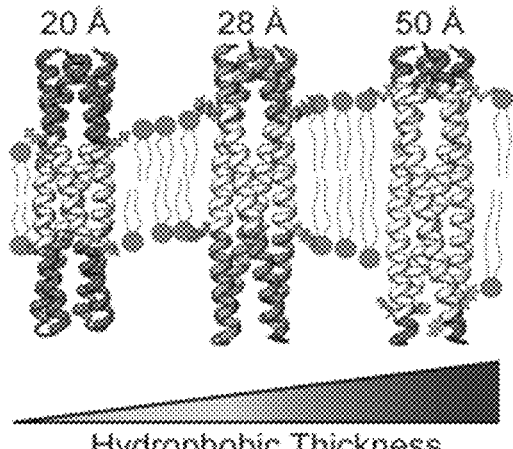
FIG. 1 is a schematic illustrating interactions between de novo designed membrane proteins of varying hydrophobic thicknesses and synthetic membranes.

Disclosed herein are methods for controlling the localization and distribution of proteins within lipid membranes. The methods assess hydrophobic mismatch between the proteins and the membranes to facilitate the selection of proteins for desired function and protein-protein interactions. Cell-mimetic membranes have proven to be powerful tools for studying lipid-protein interactions and engineering membrane-based materials. In cells, lipid-protein interactions drive inter- and intra-membrane protein organization. The methods disclosed herein leverage the hydrophobic mismatch and changes in membrane order and packing parameters between proteins and membranes to spatially organize proteins between and within membranes. The methods enable the self-assembly of membrane compartments with a unique composition of transmembrane proteins incorporated within them, in one pot. The methods also enable the organization of proteins within one membrane. This provides a dynamic membrane-based protein scaffold for controlling protein-protein interactions, which may be used for enzyme/multi enzyme assembly and protein surface display. This technology benefits the design of bioreactors, targeted therapeutics, biosensors, etc.

In some embodiments, the protein and the lipid structure are combined under conditions that promote integration of the protein into the lipid bilayer of the structure, wherein the protein has a hydrophobic thickness that is no greater than about 5 angstroms different than the hydrophobic thickness of the lipid bilayer. The difference between the hydrophobic thickness of the protein and the hydrophobic thickness of the lipid bilayer (or the "hydrophobic mismatch") may be less than about 5 angstroms, less than about 4 angstroms, less than about 3 angstroms, less than about 2 angstroms, or less than about 1 angstrom. A protein and lipid combination which have less than about 5 angstroms difference in hydrophobic thickness may be referred to herein as "protein-lipid pair." Determining protein-lipid pairs may be facilitated by computational modeling.

In some embodiments, the protein is synthesized using a cell-free system before or while combining the protein and the lipid structure. In other embodiments, the protein is an isolated protein. Proteins for use in the invention may be proteins that facilitate analysis of cellular functions and biochemical processes, as well as drug delivery, such as biosensors and pore proteins. In some embodiments, the hydrophobic thickness of the protein is no less than about 10 angstroms. In some embodiments, the hydrophobic thickness of the protein is no greater than 50 angstroms. The protein may have a hydrophobic thickness between about 10 angstroms and 50 angstroms, and any thickness in between.

The methods may further comprise incubating the lipid structure with a molecule after the protein is integrated into the bilayer. Such molecules may include analytes, drugs, and any other small molecules.

In some embodiments, the methods include combining two or more proteins with a lipid structure having two or more domains, wherein the domains have a hydrophobic thickness no less than 5 angstroms different than any other domain in the structure. The proteins and lipid structure may be combined at a temperature of between about 20 and about 35° C. After the proteins are integrated into the lipid bilayer, the temperature may be increased to between about 37 and about 45° C., or to between about 37 and about 80° C. to facilitate disorganization of the membrane and encourage co-localization of the proteins. Other methods to dissolve domains to facilitate disorganization may also be used including, but not limited to adding drugs or altering the chemical composition of the lipid membrane, such as by adding external lipids. Methods involving changing membrane tension, or adding oligomerizing or phase-segregating soluble components may be used.

The present invention is described herein using several definitions, as set forth below and throughout the application.

Definitions

The disclosed subject matter may be further described using definitions and terminology as follows. The definitions and terminology used herein are for the purpose of describing particular embodiments only and are not intended to be limiting.

A "lipid layer," "lipid structure," or "lipid membrane" means a continuous, self-assembled barrier comprising a plurality of amphiphilic lipids. In some embodiments, the lipid layer comprises a single layer of amphiphilic lipids, e.g., a micelle or a reverse micelle, having a hydrophilic surface and a hydrophobic surface. In other embodiments, the lipid layer is a lipid bilayer comprising two layers of amphiphilic lipids having an inner-hydrophilic surface, an outer-hydrophilic surface, and a hydrophobic core disposed between the inner-hydrophilic surface and the outer-hydrophilic surface, e.g., a liposome, a lipid nanoparticle, a cell, a cellular organelle, or a 2-dimensional membrane.

"Amphiphilic lipid" means any chemical compound having both hydrophilic and hydrophobic properties and typically composed of a polar head group and lipophilic tail. The polar head group may charged or uncharged. Suitably, the polar head groups may comprise anionic head groups (such as carboxylates, sulfates, sulfonates, or phosphates), cationic head groups (such as ammoniums), or uncharged head groups (such as alcohols). The lipophilic tail is typically a saturated or unsaturated alkyl or a saturated or unsaturated alkylene having at least four carbon atoms, suitably between 6 and 24 carbon atoms. Exemplary amphiphilic lipids include, without limitation, phospholipids (e.g., sphingomyelins or phosphoglycerides such as phosphatidylserines, phosphatidylethanolamines, phosphatidylinositols, or phosphatidylcholines), glycolipids, fatty acids, amphiphilic di-block copolymers, amphiphilic tri-block copolymers, amphiphilic dendrimers, amphiphilic dendrons, or peptide amphiphiles.

The lipid layers may comprise additional components. Suitably, the lipid layer may comprise a protein, a carbohydrate, a sterol, or any combination thereof. Proteins may be surface proteins, integral proteins, transmembrane proteins, globular proteins, glycoproteins, and, as used herein, also include oligopeptides.

Vesicles may be formed from lipid layers. A "vesicle" means any closed-structure comprising a lipid layer enclosing a liquid or gas. Vesicles may vary in size from about 10 nm to about 100 μm in diameter. In some cases, the vesicles may be characterized as "small" (typically less than 100 nm in diameter), "large" (typically 100 nm to 1 μm), or "giant" (typically greater than 1 μm). Vesicles may be unilamellar or multilamellar. Exemplary vesicles include, without limitation, micelles, reverse micelles, small unilamellar liposome vesicles (SUVs), large unilamellar liposome vesicles (LUVs), giant unilamellar liposome vesicles (GUVs), cells, organelles, vacuoles, lysosomes, transport vesicles, secretory vesicles, exosomes, microvesicles, membrane particles, apoptotic blebs, polymersomes, dendrimersomes, peptide-amphiphile vesicles, gas vesicles, and synthetically made vesicles.

A "transmembrane protein" is an integral membrane protein that spans the entirety of a lipid bilayer or lipid structure. Transmembrane proteins include largely hydrophobic segments that span the lipid layer, and hydrophilic segments exposed on aqueous spaces on either side of the lipid bilayer. Transmembrane proteins may reside in the membranes of synthetic vesicles, cells, organelles, etc.

"Hydrophobic thickness" means the length of the hydrophobic segment of a protein or a lipid layer.

"Hydrophobic mismatch" means the difference between the length of the hydrophobic segment of two components, such as a protein and a lipid layer.

A "domain," as used herein refers to a lateral segment of a lipid layer having a different hydrophobic thickness than the remainder of the lipid layer. A lipid layer may include two or more domains. In contrast, a lipid layer having no domains is of a uniform hydrophobic thickness throughout its entirety.

Nucleic acids, proteins, and/or other compositions described herein may be purified. As used herein, "purified" means separate from the majority of other compounds or entities, and encompasses partially purified or substantially purified. Purity may be denoted by a weight by weight measure and may be determined using a variety of analytical techniques such as but not limited to mass spectrometry, HPLC, spectrophotometer, etc.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

EXAMPLES

The following Examples are illustrative and should not be interpreted to limit the scope of the claimed subject matter.

Example 1—Materials and Methods

Materials 1,2-dioleoyl-sn-glycero-3-phosphocholine (DOPC), 1,2-dimyristoleoyl-sn-glycero-3-phosphocholine (14:1 PC), 1,2-dierucoyl-sn-glycero-3-phosphocholine (22:1 PC), Cholesterol, 1,2-dipalmitoyl-sn-glycero-3-phosphocholine (DPPC), 1,2-dioleoyl-sn-glycero-3-phosphoethanolamine-N-(7-nitro-2-1,3-benzoxadiazol-4-yl)1,2-dioleoyl-snglycero-3-phosphoethanolamine-N-(lissamine rhodamine B sulfonyl) (18:1 Rhodamine), and 1,2-dioleoyl-sn-glycero-3-phosphoethanolamine-N-(Cyanine 5.5) (Cy 5.5 PE) were purchased from Avanti Polar Lipids. PURExpress and SNAP Alexa Fluor 488 were obtained from New England Biosciences. gBlocks and primers were ordered from Integrated DNA technologies and DNA was amplified and assembled using enzymes from Thermo Fisher. Phosphate-buffered Saline (PBS), sucrose, and Sepharose 4B (45-165 mm bead diameter) were obtained from Sigma Aldrich. Protein A/G beads, Calcein dye, streptavidin, Alexa Fluor 488 Biocytin, and rapamycin were purchased from Thermo Fisher. Nanoflit substrate was purchased from Promega.

Methods

Protein design: Transmembrane proteins with different transmembrane spans were designed (with a range of 20-50 Å) by resurfacing the outside of the de novo designer transmembrane proteins with patterned hydrophobic residues and adding RK- and YW-rings at the intracellular and extracellular boundary region, respectively. The protein sequences are listed in Table 1, below. Briefly, hydrophobic residues were designed based on amino acid propensity in the membrane, replacing all polar residues exposed to the membrane. The design models of TMHC2 and TMH4C4 were used as the starting model. The sequences

TABLE 1

Sequences of protein designs. Transmembrane domains are marked in boldface.

| SEQ ID NO: | Design | Hydrophobic Length (A) | Sequence |
|---|---|---|---|
| 1 | PL421 | 10 | MTRKEIIEKLEKSLRRQKELAERLLILLLLLR LLHELLELLRRLEELQRRGSSDEEVHELLRRIIE LVERIIYLVIFIIALVREIIKLAEHQRRLVEELKK QD |
| 2 | PL422 | 20 | MTRKEIIEKLEKSLRRQKLARFLLILLLLLLA LLLELLELLRRLEELQRRGSSDEEVHELLRRIIE LVEYIILLVLFIIVLVRIIIKLAEHQRRLVEELK KQD |
| 3 | PL191 | 24 | MTRTEIIRELERSLREQRVLAIFLLALLIVLLW LLQQLKELLRELERLQREGSSDEDVRELLREIK ELVENIVYLVIIIMVLVLVIIALARTQKYLVEE LKRQD |
| 4 | PL 145 | 28 | MTRTEIIRELERSLRLQLVLAIFLLGLLIVLLW LLQQLKELLRELERLQREGSSDEDVRELLREIK ELVENIVYLVIIIMVLVLVIIALTVTQKYLVEE LKRQD |
| 5 | PL424 | 32 | MTRTEIITRLSFSLLLQLVLAIFLLALLIVLLW LLQQLKELLRELERLQREGSSDEDVRELLREIK ELVENIVYLVIIIMVLVLVIIALAVLQMYLVRE LKRQD |

TABLE 1-continued

Sequences of protein designs. Transmembrane domains are marked in boldface.

| SEQ ID NO: | Design | Hydrophobic Length (A) | Sequence |
|---|---|---|---|
| 6 | PL 193 | 40 | MTRTEIITRLSFSLLLQLVLAIFLLALLIVLLVL LIYLKELLRELERLQREGSSDEDVRELLREIKW LVIVIVALVIIIMVLVLVIIALAVLQMYLVREL KRQD |
| 7 | PL209 | 50 | MVLSHHFGKEFASATMTRTEIITRLSFSLLLQ LVLAIFLLALLIVLLVLLIVLMILLIALEYLQK EGSSDEDVKELLVLIMILVIVIVALVIIIMVLV LVIIALAVLQMYLVRELKRQD |
| 8 | TMH4C4-20 | 20 | MSAEELLRRSREYLKKVAKFQLVIALVFLILL EILSRRSEELIRELEEKGAASEAELARMKQQHM TAYLQAALTAWEIISKSLIALLLLQQNQLNLE LNTDTDKNVAEELLRRSREYLKKVAKKQLVI AFVFLILLEILSRRSEELIRELEEKGAASEAELA RMKQQHMTAYLQAALTAWEIISKSLIALLLL QQNQLNLELRH |
| 9 | TMH4C4-24 | 24 | MSAEELLRRSREYLKKVAKIQLVIALVFLILLI ILSRRSEELIRELEEKGAASEAELARMKQQHMT AYLQAALTAWEIISKSVIALLLLQQNQLNLEL NTDTDKNVAEELLRRSREYLKKVAKIQLVIAF VFLILLIILSRRSEELIRELEEKGAASEAELARM KQQHMTAYLQAALTAWEIISKSRIALLLLQQ NQLNLELRH |
| 10 | TMH4C4-40 | 40 | MSAEELLRRSRKYLILVALIQLVIAFVFLILLIL LSWLSWLLIRELEEKGAASEAELARMKIQMM TAYLQAALTAWEIIVKAVIALLLLRQNQLNL ELNTDTDKNVAEELLRRSRKYLIIVALIQLVIA FVFLILLILLSWKSWELIRELEEKGAASEAELA RMKMQVMLAYLQAALTAWEIIAKSVIALLLL LQNQLNLELRH |
| 11 | TMH4C4-50 | 50 | MSAEELLRWSRIYLVIVALIQLVIAFVFLILLIL LSWLSLVLIWELEEKGAASEAELARMILQVM TAYLQAALTAWEIIAKVVIALLLLVVNQLNL ELNTDTDKNVAEELLRRSLLYLIMVALIQLVI AFVFLILLILLSWISLLLIWELEEKGAASEAEL ARMAIQLMIAYLQAALTAWEIIAKSVIALLL LILNQLNLELRH |

Coarse grained simulations: Coarse-grained molecular dynamics simulations were conducted using the MARTINI force-field (v2.2) using GROMACS (2020.1). Simulations were performed using semi-isotropic pressure coupling to yield laterally tensionless membranes using the "martini straight" parameters (34). The secondary structure of simulated protein was fixed in the simulations by an elastic network parametrized from the predicted protein structure (35, 36). Membranes of varying lipid compositions and protein assemblies were assembled using insane.py (37) and initially equilibrated for a minimum of 10 ns, productions runs were 6 μs with three replicates and sampled every 1 ns. If not indicated otherwise, the simulation was conducted at 295° K. Trajectories were analyzed using MDAnalysis version 0.20.1 (38). Type of analysis and simulation size varying between systems: Data in FIG. 2 was obtained for single component membranes with 216 MARTINI DYPC, DOPC or DGPC lipids per leaflet. The position in normal direction to the membrane of the PO4 bead (representing the phosphate headgroup) was analyzed around a single centered protein construct for both membrane leaflets. Then PO4 positions were binned by the radial distance from the protein center with 1 nm bin width. The difference between the PO4 position for each leaflet bin then determined the membrane thickness shown as an average over the whole trajectory. For simulations shown in FIG. 3A, membranes were composed of 138 DPPC, 92 DYPC and 99 cholesterol molecules per leaflet. In a radial selection around the protein center of mass, corresponding to the first layer of surrounding lipid molecules, individual lipid types were determined. The time average of detected lipids, then determined average membrane composition around the protein center at varying temperatures. For FIG. 16A the same DPPC:DYPC:cholesterol membranes as above were compared to membranes with 326 DOPC lipids per leaflet. Both membranes contained two copies of two different protein constructs. The distributions of center of mass protein-protein distances were determined for the two membrane compositions.

Gene Assembly and Cloning: Genes listed in Table 2 (below) were ordered as gene blocks and cloned into a high copy plasmid used in previous work (39). Different fusion proteins were generated using standard restriction enzyme cloning techniques using Phusion DNA polymerase and restriction enzymes from Thermo Fisher. Pore proteins were toxic and prone to mutation and thus were not cloned into plasmids. Protein pores were ordered as gene blocks with elements required for gene transcription and translation (T7 promoter and terminator, ribosome binding site) and were amplified via PCR.

TABLE 2

DNA sequences for all proteins used in this study

| SEQ ID NO: | Construct | Sequence (DNA and protein) |
|---|---|---|
| 12 | 10 Å hairpin-mEGFP | ATGGGCTCGACCCGCAAGGAGATCATTGAAAAGTTGGAGA<br>AATCCCTTCGTCGTCAAAAAGAGTTGGCGGAACGCCTTTTG<br>ATTCTTCTGTTGTTGTTATTGCGTTTATTACATGAGTTGCTTG<br>AGCTTTTGCGCCGTCTGGAAGAATTGCAGCGTCGCGGGTCG<br>TCAGATGAGGAGGTGCATGAACTTCTGCGTCGCATTATTGA<br>ATTGGTCGAGCGCATCATTTATCTTGTCATCTTTATCATTGC<br>TCTGGTACGCGAAATTATCAAACTTGCAGAGCACCAGCGTC<br>GTTTGGTAGAAGAGCTTAAAAAGCAGGACGGTAGCAGCGG<br>ATCCATGGTGAGCAAGGGCGAGGAGCTGTTCACCGGGG<br>TGGTGCCCATCCTGGTCGAGCTGGACGGCGACGTAAAC<br>GGCCACAAGTTCAGCGTGTCCGGCGAGGGCGAGGGCGA<br>TGCCACCTACGGCAAGCTGACCCTGAAGTTCATCTGCAC<br>CACCGGCAAGCTGCCCGTGCCCTGGCCCACCCTCGTGA<br>CCACCCTGACCTACGGCGTGCAGTGCTTCAGCCGCTACC<br>CCGACCACATGAAGCAGCACGACTTCTTCAAGTCCGCCA<br>TGCCCGAAGGCTACGTCCAGGAGCGCACCATCTTCTTCA<br>AGGACGACGGCAACTACAAGACCCGCGCCGAGGTGAAG<br>TTCGAGGGCGACACCCTGGTGAACCGCATCGAGCTGAA<br>GGGCATCGACTTCAAGGAGGACGGCAACATCCTGGGGC<br>ACAAGCTGGAGTACAACTACAACAGCCACAACGTCTATA<br>TCATGGCCGACAAGCAGAAGAACGGCATCAAGGTGAAC<br>TTCAAGATCCGCCACAACATCGAGGACGGCAGCGTGCA<br>GCTCGCCGACCACTACCAGCAGAACACCCCCATCGGCG<br>ACGGCCCCGTGCTGCTGCCCGACAACCACTACCTGAGC<br>ACCCAGTCCAAGCTGAGCAAAGACCCCAACGAGAAGCG<br>CGATCACATGGTCCTGCTGGAGTTCGTGACCGCCGCCG<br>GGATCACTCTCGGCATGGACGAGCTGTACAAGTAA |
| 13 | 20 Å hairpin-mEGFP | ATGGGCTCGACTCGCAAGGAAATCATTGAGAAGTTAGAAA<br>AGAGCCTGCGTCGCCAGAAGAAACTGGCACGTTTCCTTTTA<br>ATCTTACTTTTACTGTTGTTAGCTCTGCTGCTTGAATTATTG<br>GAGCTTTTGCGCCGTCTGGAAGAGTTGCAGCGTCGCGGCTC<br>AAGTGACGAAGAAGTCCATGAATTATTACGCCGTATCATTG<br>AGCTTGTGGAATATATTATCCTTCTGGTGTTGTTCATCATCG<br>TACTTGTCCGCATCATCATCAAATTAGCAGAGCATCAACGC<br>CGCTTGGTTGAGGAACTGAAGAAGCAGGACGGTAGCAGCG<br>GATCCATGGTGAGCAAGGGCGAGGAGCTGTTCACCGGG<br>GTGGTGCCCATCCTGGTCGAGCTGGACGGCGACGTAAA<br>CGGCCACAAGTTCAGCGTGTCCGGCGAGGGCGAGGGCG<br>ATGCCACCTACGGCAAGCTGACCCTGAAGTTCATCTGCA<br>CCACCGGCAAGCTGCCCGTGCCCTGGCCCACCCTCGTG<br>ACCACCCTGACCTACGGCGTGCAGTGCTTCAGCCGCTAC<br>CCCGACCACATGAAGCAGCACGACTTCTTCAAGTCCGCC<br>ATGCCCGAAGGCTACGTCCAGGAGCGCACCATCTTCTTC<br>AAGGACGACGGCAACTACAAGACCCGCGCCGAGGTGAA<br>GTTCGAGGGCGACACCCTGGTGAACCGCATCGAGCTGA<br>AGGGCATCGACTTCAAGGAGGACGGCAACATCCTGGGG<br>CACAAGCTGGAGTACAACTACAACAGCCACAACGTCTAT<br>ATCATGGCCGACAAGCAGAAGAACGGCATCAAGGTGAA<br>CTTCAAGATCCGCCACAACATCGAGGACGGCAGCGTGC<br>AGCTCGCCGACCACTACCAGCAGAACACCCCCATCGGC<br>GACGGCCCCGTGCTGCTGCCCGACAACCACTACCTGAG<br>CACCCAGTCCAAGCTGAGCAAAGACCCCAACGAGAAGC<br>GCGATCACATGGTCCTGCTGGAGTTCGTGACCGCCGCC<br>GGGATCACTCTCGGCATGGACGAGCTGTACAAGTAA |
| 14 | 24 Å hairpin-mEGFP | ATGATGGGCACCAGGACAGAGATCATCAGGGAGCTTGAGC<br>GATCCTTGCGAGAGCAGCGCGTGCTTGCTATTTTCCTCCTGG<br>CGTTGCTCATCGTACTTCTCTGGCTGCTGCAACAACTTAAAG<br>AATTGTTGCGCGAGCTGGAACGGCTGCAAAGAGAAGGTTC<br>ATCCGACGAGGATGTAAGAGAATTGCTTAGAGAAATCAAA<br>GAACTTGTTGAGAACATTGTATATCTGGTAATAATAATCAT<br>GGTCCTCGTCCTGGTAATCATAGCCCTGGCAAGAACGCAAA<br>AATACCTTGTCGAAGAGCTGAAGCGGCAGGATGGTAGCAG<br>CGGATCCATGGTGAGCAAGGGCGAGGAGCTGTTCACCG<br>GGGTGGTGCCCATCCTGGTCGAGCTGGACGGCGACGTA<br>AACGGCCACAAGTTCAGCGTGTCCGGCGAGGGCGAGGG<br>CGATGCCACCTACGGCAAGCTGACCCTGAAGTTCATCTG<br>CACCACCGGCAAGCTGCCCGTGCCCTGGCCCACCCTCG<br>TGACCACCCTGACCTACGGCGTGCAGTGCTTCAGCCGCT<br>ACCCCGACCACATGAAGCAGCACGACTTCTTCAAGTCCG<br>CCATGCCCGAAGGCTACGTCCAGGAGCGCACCATCTTCT<br>TCAAGGACGACGGCAACTACAAGACCCGCGCCGAGGTG<br>AAGTTCGAGGGCGACACCCTGGTGAACCGCATCGAGCT<br>GAAGGGCATCGACTTCAAGGAGGACGGCAACATCCTGG |

TABLE 2-continued

DNA sequences for all proteins used in this study

| SEQ ID NO: | Construct | Sequence (DNA and protein) |
|---|---|---|
| | | GGCACAAGCTGGAGTACAACTACAACAGCCACAACGTC |
| | | TATATCATGGCCGACAAGCAGAAGAACGGCATCAAGGT |
| | | GAACTTCAAGATCCGCCACAACATCGAGGACGGCAGCG |
| | | TGCAGCTCGCCGACCACTACCAGCAGAACACCCCCATC |
| | | GGCGACGGCCCCGTGCTGCTGCCCGACAACCACTACCT |
| | | GAGCACCCAGTCCAAGCTGAGCAAAGACCCCAACGAGA |
| | | AGCGCGATCACATGGTCCTGCTGGAGTTCGTGACCGCC |
| | | GCCGGGATCACTCTCGGCATGGACGAGCTGTACAAGTA |
| | | A |
| 15 | 28 Å hairpin-mEGFP | ATGACCCGAACGGAAATCATTAGGGAGCTGGAGCGAAGTT |
| | | TGCGCCTCCAGCTGGTCCTTGCGATATTTCTGCTCGGACTTT |
| | | TGATCGTACTTCTGTGGCTGTTGCAGCAGCTGAAAGAACTG |
| | | TTGCGGGAGCTTGAAAGGCTCCAACGGGAGGGTAGCAGCG |
| | | ATGAGGACGTTCGGGAGCTGCTTAGGGAGATTAAGGAGCTT |
| | | GTGGAGAACATTGTTTATTTGGTCATTATTATCATGGTGTTG |
| | | GTTCTCGTAATAATAGCACTCACTGTAACTCAAAAGTATCT |
| | | GGTGGAGGAACTTAAACGGCAGGATGGCGGCGGATCCATG |
| | | GTGAGCAAGGGCGAGGAGCTGTTCACCGGGGTGGTGCC |
| | | CATCCTGGTCGAGCTGGACGGCGACGTAAACGGCCACA |
| | | AGTTCAGCGTGTCCGGCGAGGGCGAGGGCGATGCCACC |
| | | TACGGCAAGCTGACCCTGAAGTTCATCTGCACCACCGGC |
| | | AAGCTGCCCGTGCCCTGGCCCACCCTCGTGACCACCCT |
| | | GACCTACGGCGTGCAGTGCTTCAGCCGCTACCCCGACC |
| | | ACATGAAGCAGCACGACTTCTTCAAGTCCGCCATGCCCG |
| | | AAGGCTACGTCCAGGAGCGCACCATCTTCTTCAAGGAC |
| | | GACGGCAACTACAAGACCCGCGCCGAGGTGAAGTTCGA |
| | | GGGCGACACCCTGGTGAACCGCATCGAGCTGAAGGGCA |
| | | TCGACTTCAAGGAGGACGGCAACATCCTGGGGCACAAG |
| | | CTGGAGTACAACTACAACAGCCACAACGTCTATATCATG |
| | | GCCGACAAGCAGAAGAACGGCATCAAGGTGAACTTCAA |
| | | GATCCGCCACAACATCGAGGACGGCAGCGTGCAGCTCG |
| | | CCGACCACTACCAGCAGAACACCCCCATCGGCGACGGC |
| | | CCCGTGCTGCTGCCCGACAACCACTACCTGAGCACCCA |
| | | GTCCAAGCTGAGCAAAGACCCCAACGAGAAGCGCGATC |
| | | ACATGGTCCTGCTGGAGTTCGTGACCGCCGCCGGGATC |
| | | ACTCTCGGCATGGACGAGCTGTACAAGTAA |
| 16 | 32 Å hairpin-mEGFP | ATGGGCTCGACCCGTACCGAAATCATTACCCGTCTGAGCTT |
| | | CAGCCTGCTGCTGCAGCTGGTTCTGGCGATTTTTTCTGCTGGC |
| | | GCTGCTGATCGTGCTGCTGTGGCTGCTGCAGCAACTGAAGG |
| | | AACTGCTGCGTGAGCTGGAACGTCTGCAACGTGAGGGTAGC |
| | | AGCGACGAAGATGTTCGTGAGCTGCTGCGTGAGATTAAAGA |
| | | ACTGGTGGAGAACATCGTTTACCTGGTGATCATTATCATGG |
| | | TGCTGGTTCTGGTGATTATCGCGCTGGCGGTTCTGCAGATGT |
| | | ATCTGGTGCGTGAACTGAAGCGTCAAGACGGTAGCAGCGG |
| | | ATCCATGGTGAGCAAGGGCGAGGAGCTGTTCACCGGGG |
| | | TGGTGCCCATCCTGGTCGAGCTGGACGGCGACGTAAAC |
| | | GGCCACAAGTTCAGCGTGTCCGGCGAGGGCGAGGGCGA |
| | | TGCCACCTACGGCAAGCTGACCCTGAAGTTCATCTGCAC |
| | | CACCGGCAAGCTGCCCGTGCCCTGGCCCACCCTCGTGA |
| | | CCACCCTGACCTACGGCGTGCAGTGCTTCAGCCGCTACC |
| | | CCGACCACATGAAGCAGCACGACTTCTTCAAGTCCGCCA |
| | | TGCCCGAAGGCTACGTCCAGGAGCGCACCATCTTCTTCA |
| | | AGGACGACGGCAACTACAAGACCCGCGCCGAGGTGAAG |
| | | TTCGAGGGCGACACCCTGGTGAACCGCATCGAGCTGAA |
| | | GGGCATCGACTTCAAGGAGGACGGCAACATCCTGGGGC |
| | | ACAAGCTGGAGTACAACTACAACAGCCACAACGTCTATA |
| | | TCATGGCCGACAAGCAGAAGAACGGCATCAAGGTGAAC |
| | | TTCAAGATCCGCCACAACATCGAGGACGGCAGCGTGCA |
| | | GCTCGCCGACCACTACCAGCAGAACACCCCCATCGGCG |
| | | ACGGCCCCGTGCTGCTGCCCGACAACCACTACCTGAGC |
| | | ACCCAGTCCAAGCTGAGCAAAGACCCCAACGAGAAGCG |
| | | CGATCACATGGTCCTGCTGGAGTTCGTGACCGCCGCCG |
| | | GGATCACTCTCGGCATGGACGAGCTGTACAAGTAA |
| 17 | 40 Å hairpin-mEGFP | ATGACTAGGACGGAGATTATAACTAGGCTCTCTTTTTCTCTT |
| | | TTGTTGCAGCTCGTGCTCGCTATATTTCTCCTTGCTCTTCTGA |
| | | TAGTCCTTCTTGTTCTGCTTATCTATTTGAAGGAACTTCTCC |
| | | GCGAGTTGGAGCGACTCCAGAGGGAGGGGTCAAGCGACGA |
| | | AGATGTACGAGAATTGTTGCGCGAAATTAAATGGTTGGTAA |
| | | TTGTGATTGTGGCTCTCGTAATCATTATAATGGTCTTGGTAT |
| | | TGGTAATCATCGCTCTTGCTGTGTTGCAAATGTACCTCGTTC |
| | | GCGAACTGAAACGGCAGGATGGCGGCGGATCCATGGTGAG |
| | | CAAGGGCGAGGAGCTGTTCACCGGGGTGGTGCCCATCC |

TABLE 2-continued

DNA sequences for all proteins used in this study

| SEQ ID NO: | Construct | Sequence (DNA and protein) |
|---|---|---|
| | | TGGTCGAGCTGGACGGCGACGTAAACGGCCACAAGTTC<br>AGCGTGTCCGGCGAGGGCGAGGGCGATGCCACCTACGG<br>CAAGCTGACCCTGAAGTTCATCTGCACCACCGGCAAGCT<br>GCCCGTGCCCTGGCCCACCCTCGTGACCACCCTGACCTA<br>CGGCGTGCAGTGCTTCAGCCGCTACCCCGACCACATGA<br>AGCAGCACGACTTCTTCAAGTCCGCCATGCCCGAAGGCT<br>ACGTCCAGGAGCGCACCATCTTCTTCAAGGACGACGGC<br>AACTACAAGACCCGCGCCGAGGTGAAGTTCGAGGGCGA<br>CACCCTGGTGAACCGCATCGAGCTGAAGGGCATCGACT<br>TCAAGGAGGACGGCAACATCCTGGGGCACAAGCTGGAG<br>TACAACTACAACAGCCACAACGTCTATATCATGGCCGAC<br>AAGCAGAAGAACGGCATCAAGGTGAACTTCAAGATCCG<br>CCACAACATCGAGGACGGCAGCGTGCAGCTCGCCGACC<br>ACTACCAGCAGAACACCCCCATCGGCGACGGCCCCGTG<br>CTGCTGCCCGACAACCACTACCTGAGCACCCAGTCCAAG<br>CTGAGCAAAGACCCCAACGAGAAGCGCGATCACATGGT<br>CCTGCTGGAGTTCGTGACCGCCGCCGGGATCACTCTCG<br>GCATGGACGAGCTGTACAAGTAA |
| 18 | 50 Å hairpin-mEGFP | ATGGTGCTGTCTCATCATTTTGGCAAAGAATTCGCTAGCGC<br>CACCATGACCCGCACGGAGATTATCACCAGGCTCAGTTTTT<br>CCCTTTTGTTGCAACTTGTCTTGGCAATTTTTTTTGCTCGCACT<br>GCTGATCGTACTCTTGGTGCTTTTGATAGTTCTGATGATTCT<br>CCTTATAGCGTTGGAATATCTTCAAAAAGAGGGATCTTCAG<br>ATGAGGATGTGAAAGAACTCCTGGTGCTCATAATGATTTTG<br>GTGATAGTGATTGTTGCCCTGGTAATTATAATCATGGTACTG<br>GTCCTCGTTATAATCGCTCTGGCTGTGTTGCAGATGTACCTG<br>GTTCGGGAACTCAAGCGACAAGACGGCGGCGGATCCATGG<br>TGAGCAAGGGCGAGGAGCTGTTCACCGGGGTGGTGCCC<br>ATCCTGGTCGAGCTGGACGGCGACGTAAACGGCCACAA<br>GTTCAGCGTGTCCGGCGAGGGCGAGGGCGATGCCACCT<br>ACGGCAAGCTGACCCTGAAGTTCATCTGCACCACCGGC<br>AAGCTGCCCGTGCCCTGGCCCACCCTCGTGACCACCCT<br>GACCTACGGCGTGCAGTGCTTCAGCCGCTACCCCGACC<br>ACATGAAGCAGCACGACTTCTTCAAGTCCGCCATGCCCG<br>AAGGCTACGTCCAGGAGCGCACCATCTTCTTCAAGGAC<br>GACGGCAACTACAAGACCCGCGCCGAGGTGAAGTTCGA<br>GGGCGACACCCTGGTGAACCGCATCGAGCTGAAGGGCA<br>TCGACTTCAAGGAGGACGGCAACATCCTGGGGCACAAG<br>CTGGAGTACAACTACAACAGCCACAACGTCTATATCATG<br>GCCGACAAGCAGAAGAACGGCATCAAGGTGAACTTCAA<br>GATCCGCCACAACATCGAGGACGGCAGCGTGCAGCTCG<br>CCGACCACTACCAGCAGAACACCCCCATCGGCGACGGC<br>CCCGTGCTGCTGCCCGACAACCACTACCTGAGCACCCA<br>GTCCAAGCTGAGCAAAGACCCCAACGAGAAGCGCGATC<br>ACATGGTCCTGCTGGAGTTCGTGACCGCCGCCGGGATC<br>ACTCTCGGCATGGACGAGCTGTACAAGTAA |
| 19 | 50 Å hairpin-Malachite Green Aptamer | taatacgactcactatagggagaccacaacggtttccctctagaaataattttgtttaactttaagaagg<br>agatatacaTATGATGGTGCTGTCTCATCATTTTGGCAAAGAA<br>TTCGCTAGCGCCACCATGACCCGCACGGAGATTATCACC<br>AGGCTCAGTTTTTCCCTTTTGTTGCAACTTGTCTTGGCA<br>ATTTTTTTGCTCGCACTGCTGATCGTACTCTTGGTGCTTT<br>TGATAGTTCTGATGATTCTCCTTATAGCGTTGGAATATC<br>TTCAAAAAGAGGGATCTTCAGATGAGGATGTGAAAGAA<br>CTCCTGGTGCTCATAATGATTTTGGTGATAGTGATTGTT<br>GCCCTGGTAATTATAATCATGGTACTGGTCCTCGTTATA<br>ATCGCTCTGGCTGTGTTGCAGATGTACCTGGTTCGGGAA<br>CTCAAGCGACAAGACGGCGGCGGATCCGACTATAAAGA<br>CGATGACGATAAATAAGtcgac<u>GGGATCCCGACTGGCGAGA<br>GCCAGGTAACGAATGGATCGGGTCGGCATGGCATCTCCACC<br>TCCTCGCGGTCCGACCTGGGCATCCGAAGGAGGACGTCGTC<br>CACTCGGATGGCTAAGGGA</u>cggctgctaacaaagcccgaaaggaagctgag<br>ttggctgctgccaccgctgagcaataactagcataaccccttggggcctctaaacgggtcttgaggg<br>gttttttg |
| 20 | FLAG-50 Å Hairpin-mEGFP | ATGGATTACAAGGATGACGACGATAAGcatATGGTGCTGTCT<br>CATCATTTTGGCAAAGAATTCGCTAGCGCCACCATGACCCG<br>CACGGAGATTATCACCAGGCTCAGTTTTTCCCTTTTGTTGCA<br>ACTTGTCTTGGCAATTTTTTTTGCTCGCACTGCTGATCGTACT<br>CTTGGTGCTTTTGATAGTTCTGATGATTCTCCTTATAGCGTT<br>GGAATATCTTCAAAAAGAGGGATCTTCAGATGAGGATGTGA<br>AAGAACTCCTGGTGCTCATAATGATTTTGGTGATAGTGATT<br>GTTGCCCTGGTAATTATAATCATGGTACTGGTCCTCGTTATA<br>ATCGCTCTGGCTGTGTTGCAGATGTACCTGGTTCGGGAACT |

TABLE 2-continued

DNA sequences for all proteins used in this study

| SEQ ID NO: | Construct | Sequence (DNA and protein) |
|---|---|---|
| | | CAAGCGACAAGACGGCGGCGGATCCATGGTGAGCAAGGG<br>CGAGGAGCTGTTCACCGGGGTGGTGCCCATCCTGGTCG<br>AGCTGGACGGCGACGTAAACGGCCACAAGTTCAGCGTG<br>TCCGGCGAGGGCGAGGGCGATGCCACCTACGGCAAGCT<br>GACCCTGAAGTTCATCTGCACCACCGGCAAGCTGCCCGT<br>GCCCTGGCCCACCCTCGTGACCACCCTGACCTACGGCG<br>TGCAGTGCTTCAGCCGCTACCCCGACCACATGAAGCAG<br>CACGACTTCTTCAAGTCCGCCATGCCCGAAGGCTACGTC<br>CAGGAGCGCACCATCTTCTTCAAGGACGACGGCAACTA<br>CAAGACCCGCGCCGAGGTGAAGTTCGAGGGCGACACCC<br>TGGTGAACCGCATCGAGCTGAAGGGCATCGACTTCAAG<br>GAGGACGGCAACATCCTGGGGCACAAGCTGGAGTACAA<br>CTACAACAGCCACAACGTCTATATCATGGCCGACAAGCA<br>GAAGAACGGCATCAAGGTGAACTTCAAGATCCGCCACA<br>ACATCGAGGACGGCAGCGTGCAGCTCGCCGACCACTAC<br>CAGCAGAACACCCCCATCGGCGACGGCCCCGTGCTGCT<br>GCCCGACAACCACTACCTGAGCACCCAGTCCAAGCTGA<br>GCAAAGACCCCAACGAGAAGCGCGATCACATGGTCCTG<br>CTGGAGTTCGTGACCGCCGCCGGGATCACTCTCGGCAT<br>GGACGAGCTGTACAAGTAA |
| 21 | 20 Å hairpin-SNAP | ATGGGCTCGACTCGCAAGGAAATCATTGAGAAGTTAGAAA<br>AGAGCCTGCGTCGCCAGAAGAAACTGGCACGTTTCCTTTTA<br>ATCTTACTTTTACTGTTGTTAGCTCTGCTGCTTGAATTATTG<br>GAGCTTTTGCGCCGTCTGGAAGAGTTGCAGCGTCGCGGCTC<br>AAGTGACGAAGAAGTCCATGAATTATTACGCCGTATCATTG<br>AGCTTGTGGAATATATTATCCTTCTGGTGTTGTTCATCATCG<br>TACTTGTCCGCATCATCATCAAATTAGCAGAGCATCAACGC<br>CGCTTGGTTGAGGAACTGAAGAAGCAGGACGGTAGCAGCG<br>GATCCATGGACAAAGATTGCGAAATGAAACGTACCACCC<br>TGGATAGCCCGCTGGGCAAACTGGAACTGAGCGGCTGC<br>GAACAGGGCCTGCATGAAATTAAACTGCTGGGTAAAGG<br>CACCAGCGCGGCCGATGCGGTTGAAGTTCCGGCCCCGG<br>CCGCCGTGCTGGGTGGTCCGGAACCGCTGATGCAGGCG<br>ACCGCGTGGCTGAACGCGTATTTTCATCAGCCGGAAGC<br>GATTGAAGAATTTCCGGTTCCGGCGCTGCATCATCCGGT<br>GTTTCAGCAGGAGAGCTTTACCCGTCAGGTGCTGTGGA<br>AACTGCTGAAAGTGGTTAAATTTGGCGAAGTGATTAGCT<br>ATCAGCAGCTGGCGGCCCTGGCGGGTAATCCGGCGGCC<br>ACCGCCGCCGTTAAAACCGCGCTGAGCGGTAACCCGGT<br>GCCGATTCTGATTCCGTGCCATCGTGTGGTTAGCTCTAG<br>CGGTGCGGTTGGCGGTTATGAAGGTGGTCTGGCGGTGA<br>AAGAGTGGCTGCTGGCCCATGAAGGTCATCGTCTGGGT<br>AAACCGGGTCTGGGATAA |
| 22 | 24 Å hairpin-SNAP | ATGGGCACCAGGACAGAGATCATCAGGGAGCTTGAGCGAT<br>CCTTGCGAGAGCAGCGCGTGCTTGCTATTTTCCTCCTGGCGT<br>TGCTCATCGTACTTCTCTGGCTGCTGCAACAACTTAAAGAAT<br>TGTTGCGCGAGCTGGAACGGCTGCAAAGAGAAGGTTCATCC<br>GACGAGGATGTAAGAGAATTGCTTAGAGAAATCAAAGAAC<br>TTGTTGAGAACATTGTATATCTGGTAATAATAATCATGGTCC<br>TCGTCCTGGTAATCATAGCCCTGGCAAGAACGCAAAAATAC<br>CTTGTCGAAGAGCTGAAGCGGCAGGATGGCGGCGGATCCA<br>TGGACAAAGATTGCGAAATGAAACGTACCACCCTGGATA<br>GCCCGCTGGGCAAACTGGAACTGAGCGGCTGCGAACAG<br>GGCCTGCATGAAATTAAACTGCTGGGTAAAGGCACCAG<br>CGCGGCCGATGCGGTTGAAGTTCCGGCCCCGGCCGCCG<br>TGCTGGGTGGTCCGGAACCGCTGATGCAGGCGACCGCG<br>TGGCTGAACGCGTATTTTCATCAGCCGGAAGCGATTGAA<br>GAATTTCCGGTTCCGGCGCTGCATCATCCGGTGTTTCAG<br>CAGGAGAGCTTTACCCGTCAGGTGCTGTGGAAACTGCT<br>GAAAGTGGTTAAATTTGGCGAAGTGATTAGCTATCAGCA<br>GCTGGCGGCCCTGGCGGGTAATCCGGCGGCCACCGCCG<br>CCGTTAAAACCGCGCTGAGCGGTAACCCGGTGCCGATT<br>CTGATTCCGTGCCATCGTGTGGTTAGCTCTAGCGGTGCG<br>GTTGGCGGTTATGAAGGTGGTCTGGCGGTGAAAGAGTG<br>GCTGCTGGCCCATGAAGGTCATCGTCTGGGTAAACCGG<br>GTCTGGGATAA |
| 23 | 40 Å hairpin-SNAP | ATGACTAGGACGGAGATTATAACTAGGCTCTCTTTTTCTCTT<br>TTGTTGCAGCTCGTGCTCGCTATATTTCTCCTTGCTCTTCTGA<br>TAGTCCTTCTTGTTCTGCTTATCTATTTGAAGGAACTTCTCC<br>GCGAGTTGGAGCGACTCCAGAGGGAGGGGTCAAGCGACGA<br>AGATGTACGAGAATTGTTGCGCGAAATTAAATGGTTGGTAA<br>TTGTGATTGTGGCTCTCGTAATCATTATAATGGTCTTGGTAT |

TABLE 2-continued

DNA sequences for all proteins used in this study

| SEQ ID NO: | Construct | Sequence (DNA and protein) |
|---|---|---|
| | | TGGTAATCATCGCTCTTGCTGTGTTGCAAATGTACCTCGTTC GCGAACTGAAACGGCAGGATGGCGGCGGATCCATGGACA AAGATTGCGAAATGAAACGTACCACCCTGGATAGCCCG CTGGGCAAACTGGAACTGAGCGGCTGCGAACAGGGCCT GCATGAAATTAAACTGCTGGGTAAAGGCACCAGCGCGG CCGATGCGGTTGAAGTTCCGGCCCCGGCCGCCGTGCTG GGTGGTCCGGAACCGCTGATGCAGGCGACCGCGTGGCT GAACGCGTATTTTCATCAGCCGGAAGCGATTGAAGAATT TCCGGTTCCGGCGCTGCATCATCCGGTGTTTCAGCAGGA GAGCTTTACCCGTCAGGTGCTGTGGAAACTGCTGAAAGT GGTTAAATTTGGCGAAGTGATTAGCTATCAGCAGCTGGC GGCCCTGGCGGGTAATCCGGCGGCCACCGCCGCCGTTA AAACCGCGCTGAGCGGTAACCCGGTGCCGATTCTGATT CCGTGCCATCGTGTGGTTAGCTCTAGCGGTGCGGTTGG CGGTTATGAAGGTGGTCTGGCGGTGAAAGAGTGGCTGC TGGCCCATGAAGGTCATCGTCTGGGTAAACCGGGTCTG GGATAA |
| 24 | 50 Å hairpin-SNAP | ATGGTGCTGTCTCATCATTTTGGCAAAGAATTCGCTAGCGC CACCATGACCCGCACGGAGATTATCACCAGGCTCAGTTTTT CCCTTTTGTTGCAACTTGTCTTGGCAATTTTTTTGCTCGCACT GCTGATCGTACTCTTGGTGCTTTTGATAGTTCTGATGATTCT CCTTATAGCGTTGGAATATCTTCAAAAAGAGGGATCTTCAG ATGAGGATGTGAAAGAACTCCTGGTGCTCATAATGATTTTG GTGATAGTGATTGTTGCCCTGGTAATTATAATCATGGTACTG GTCCTCGTTATAATCGCTCTGGCTGTGTTGCAGATGTACCTG GTTCGGGAACTCAAGCGACAAGACGGCGGCGGATCCATGG ACAAAGATTGCGAAATGAAACGTACCACCCTGGATAGCC CGCTGGGCAAACTGGAACTGAGCGGCTGCGAACAGGGC CTGCATGAAATTAAACTGCTGGGTAAAGGCACCAGCGC GGCCGATGCGGTTGAAGTTCCGGCCCCGGCCGCCGTGC TGGGTGGTCCGGAACCGCTGATGCAGGCGACCGCGTGG CTGAACGCGTATTTTCATCAGCCGGAAGCGATTGAAGAA TTTCCGGTTCCGGCGCTGCATCATCCGGTGTTTCAGCAG GAGAGCTTTACCCGTCAGGTGCTGTGGAAACTGCTGAA AGTGGTTAAATTTGGCGAAGTGATTAGCTATCAGCAGCT GGCGGCCCTGGCGGGTAATCCGGCGGCCACCGCCGCCG TTAAAACCGCGCTGAGCGGTAACCCGGTGCCGATTCTG ATTCCGTGCCATCGTGTGGTTAGCTCTAGCGGTGCGGTT GGCGGTTATGAAGGTGGTCTGGCGGTGAAAGAGTGGCT GCTGGCCCATGAAGGTCATCGTCTGGGTAAACCGGGTC TGGGATAA |
| 25 | TMH4C4 20 Å-FLAG | ATGAGTGCCGAGGAACTGCTGCGTCGTTCGCGCGAATATCT TAAGAAGGTTGCTAAGTTTCAACTTGTGATCGCACTCGTATT CCTTATCCTGCTGGAAATCCTTTCGCGCCGTAGCGAGGAGC TGATCCGTGAATTAGAAGAGAAAGGCGCAGCCTCAGAGGC GGAGCTGGCCCGCATGAAACAACAACACATGACTGCCTACC TGCAAGCCGCGTTAACCGCCTGGGAGATCATCAGCAAGAGC CTCATCGCCCTGTTATTACTCCAGCAGAATCAGCTCAATCTG GAACTTAACACGGATACAGACAAGAACGTAGCCGAGGAGT TACTTCGTCGTAGCCGTGAGTATCTTAAGAAGGTGGCGAAG AAGCAACTGGTTATTGCTTTTGTATTCCTCATCTTGCTCGAG ATTTTAAGCCGCCGTAGTGAGGAGTTAATTCGTGAGTTAGA GGGAGAAGGGCGCGGCGTCGGAAGCCGAGTTGGCTCGCATG AAGCAACAACACATGACCGCCTATTTGCAGGCAGCGCTGAC TGCCTGGGAGATCATTTCCAAATCTTTAATCGCGCTCCTGCT TCTGCAACAGAATCAACTGAATCTCGAGCTCCGCCATGGCG GATCCGGGAGCGACTACAAAGACGATGACGATAAGTAA |
| 26 | TMH4C4 24 Å-FLAG | ATGTCCGCCGAGGAGTTACTGCGCCGTTCCCGCGAGTACTT AAAGAAGGTCGCTAAAATTCAGCTGGTTATTGCTCTCGTCT TCTTGATCCTTCTCATCATTTTGTCCCGCCGTAGCGAGGAAC TCATCCGCGAACTCGAGGAGAAGGGCGCCGCCAGCGAGGC CGAGTTGGCCCGCATGAAGCAACAACACATGACGGCGTATT TGCAGGCCGCGTTGACTGCTTGGGAAATCATCTCAAAATCT GTTATTGCTCTGTTACTTTTGCAACAGAATCAATTAAATTTG GAGCTTAATACCGACACCGACAAGAATGTGGCTGAGGAGT ATTACGCCGCTCACGTGAGTATCTGAAGAAGGTAGCAAAGA TCCAGTTAGTTATCGCCTTCGTGTTCCTTATTCTTCTGATCAT TTTAAGCCGTCGCTCAGAGGAGCTGATTCGTGAGCTTGAAG AAAAGGGAGCGGCTTCAGAAGCGGAACTGGCCCGTATGAA GCAACAGCACATGACGGCATATCTTCAGGCCGCGTTAACGG |

TABLE 2-continued

DNA sequences for all proteins used in this study

| SEQ ID NO: | Construct | Sequence (DNA and protein) |
|---|---|---|
| | | CTTGGGAGATTATTTCAAAGAGTCGCATCGCATTGCTTCTGT<br>TACAACAAAATCAGTTGAACCTGGAGCTCCGTCACGGTGGA<br>TCCGGGTCAGACTATAAAGATGATGACGACAAGTAA |
| 27 | TMH4C4<br>40 Å-<br>FLAG | ATGTCAGCCGAGGAGTTGCTGCGTCGCTCTCGCAAGTACTT<br>AATTTTGGTGGCTTTGATTCAACTGGTGATCGCCTTCGTTTT<br>CCTCATTCTTCTGATTCTTTTGAGCTGGCTCTCATGGCTGTT<br>AATTCGTGAGCTCGAGGAGAAAGGGGCAGCGAGCGAGGCT<br>GAGTTGGCGCGCATGAAGATTCAGATGATGACTGCCTATCT<br>GCAGGCCGCGCTGACCGCCTGGGAGATCATTGTTAAAGCCG<br>TTATTGCCTTGCTCCTGCTCCGCCAAAATCAACTGAATCTTG<br>AGCTCAACACTGACACAGACAAGAATGTGGCAGAGGAGCT<br>TCTCCGTCGTAGCCGCAAGTACTTAATCATTGTGGCCTTAAT<br>TCAGTTGGTAATCGCATTCGTCTTTCTGATCCTGTTAATCTT<br>GCTTTCATGGAAGTCGTGGGAGCTGATTCGCGAGCTTGAAG<br>AGAAGGGCGCCGCCTCGGAAGCCGAACTCGCTCGTATGAA<br>GATGCAAGTGATGTTAGCCTATCTCCAAGCAGCTCTGACCG<br>CTTGGGAAATTATTGCGAAGTCAGTAATTGCGTTATTACTTC<br>TCCTGCAAAACCAATTAAACCTGGAGCTGCGCCACGGCGGA<br>TCCGGAAGTGACTACAAGGATGACGATGACAAGTAA |
| 28 | TMH4C4<br>50 Å-<br>FLAG | ATGTCTGCTGAGGAGTTGTTACGTTGGAGCCGCATTTATTTA<br>GTCATCGTGGCCTTAATCCAGTTGGTTATCGCTTTCGTATTC<br>CTTATTTTGCTCATCTTGCTGTCCTGGCTTTCATTAGTGCTCA<br>TCTGGGAGTTAGAGGAGAAGGGCGCTGCAAGTGAGGCGGA<br>GCTTGCGCGCATGATTCTCCAGGTCATGACGGCGTACTTGC<br>AAGCAGCCTTAACTGCGTGGGAGATTATCGCAAAGGTCGTA<br>ATTGCCCTGCTCCTGCTTGTGGTTAACCAGCTTAATCTCGAG<br>CTGAACACGGACACAGATAAGAACGTCGCCGAGGAGCTGT<br>TACGCCGTTCCCTTTTGTATCTGATCATGGTAGCCCTCATTC<br>AATTAGTCATTGCATTCGTATTCCTTATCTTGTTAATTCTCTT<br>GAGCTGGATCTCGCTTCTGCTTATCTGGGAACTCGAGGAAA<br>AGGGCGCTGCGAGCGAAGCAGAGCTCGCCCGTATGGCGAT<br>CCAATTAATGATTGCTTATCTCCAAGCGGCCCTGACCGCAT<br>GGGAGATCATTGCAAAGAGCGTCATCGCCTTGCTTCTTCTC<br>ATCTTAAATCAACTGAATCTTGAACTGCGTCACGGAGGATC<br>CGGTAGTGACTACAAGGACGACGACGACAAGTAA |
| 29 | 20 Å<br>Hairpin-<br>FKBP-<br>LgBit | ATGGGCTCGACTCGCAAGGAAATCATTGAGAAGTTAGAAA<br>AGAGCCTGCGTCGCCAGAAGAAACTGGCACGTTTCCTTTTA<br>ATCTTACTTTTACTGTTGTTAGCTCTGCTGCTTGAATTATTG<br>GAGCTTTTGCGCCGTCTGGAAGAGTTGCAGCGTCGCGGCTC<br>AAGTGACGAAGAAGTCCATGAATTATTACGCCGTATCATTG<br>AGCTTGTGGAATATATTATCCTTCTGGTGTTGTTCATCATCG<br>TACTTGTCCGCATCATCATCAAATTAGCAGAGCATCAACGC<br>CGCTTGGTTGAGGAACTGAAGAAGCAGGACGGTAGCAGCG<br>GATCCGCAAGTCCGGCAGCACCGGCACCGGCATCACCAGCT<br>GCACCAGCACCTAGTGCACCGGCAGGCGGT<u>ATTCTGTGGCA</u><br><u>TGAAATGTGGCACGAAGGTCTGGAAGAAGCAAGCCGTCTG</u><br><u>TATTTTGGTGAACGTAATGTGAAAGGCATGTTTGAAGTTCT</u><br><u>GGAACCGCTGCATGCAATGATGGAACGTGGTCCGCAGACA</u><br><u>CTGAAAGAAACCAGCTTTAATCAGGCCTATGGTCGTGATCT</u><br><u>GATGGAAGCACAAGAATGGTGTCGCAAATACATGAAAAGC</u><br><u>GGTAACGTTAAAGATCTGCTGCAGGCATGGGATCTGTATTA</u><br><u>TCATGTTTTTCGTCGCATTAGCAAAGGTGGTAGCGGTGGTG</u><br><u>GTGGTTCTGGTGGTAGCAGCTCAGGTGGT</u>GTTTTTACCCTG<br>GAAGATTTTGTTGGTGATTGGGAACAGACCGCAGCATAT<br>AATCTGGATCAGGTGCTGGAACAAGGTGGTGTGAGCAG<br>CCTGCTGCAGAATCTGGCAGTTAGCGTTACCCCGATTCA<br>GCGTATTGTTCGTAGCGGTGAAAATGCCCTGAAAATTGA<br>TATTCATGTGATCATCCCGTATGAAGGTCTGAGCGCAGA<br>TCAGATGGCACAGATTGAAGAAGTGTTCAAAGTTGTTTA<br>TCCGGTGGATGACCACCATTTTAAAGTTATTCTGCCGTA<br>TGGCACCCTGGTTATTGATGGTGTGACCCCGAATATGCT<br>GAATTATTTCGGTCGTCCTTATGAAGGTATTGCCGTTTT<br>TGATGGCAAAAAAATCACCGTTACCGGTACACTGTGTGAA<br>CGGTAACAAAATTATCGATGAACGTCTGATTACACCGGA<br>TGGTAGCATGCTGTTTCGTGTTACCATTAACAGCTAA |
| 30 | 50 Å<br>Hairpin-<br>FRB-<br>SmBit | ATGGGTGCTGTCTCATCATTTTGGCAAAGAATTCGCTAGCGC<br>CACCATGACCCGCACGGAGATTATCACCAGGCTCAGTTTTT<br>CCCTTTTGTTGCAACTTGTCTTGGCAATTTTTTTGCTCGCACT<br>GCTGATCGTACTCTTGGTGCTTTTGATAGTTCTGATGATTCT<br>CCTTATAGCGTTGGAATATCTTCAAAAAGAGGGATCTTCAG<br>ATGAGGATGTGAAAGAACTCCTGGTGCTCATAATGATTTTG |

TABLE 2-continued

DNA sequences for all proteins used in this study

SEQ ID
NO:    Construct    Sequence (DNA and protein)

GTGATAGTGATTGTTGCCCTGGTAATTATAATCATGGTACTG
                    GTCCTCGTTATAATCGCTCTGGCTGTGTTGCAGATGTACCTG
                    GTTCGGGAACTCAAGCGACAAGACGGCGGCGGATCCGCAA
                    GTCCGGCAGCACCGGCACCGGCATCACCAGCTGCACCAGCA
                    CCTAGTGCACCGGCAGGCGGTGGTGTTCAGGTTGAAACCAT
                    TAGTCCTGGTGATGGTCGTACCTTTCCGAAACGTGGTCAGA
                    CCTGTGTTGTTCATTACACCGGTATGCTGGAAGATGGCAAA
                    AAATTCGATAGCAGCCGTGATCGTAATAAGCCGTTTAAATT
                    CATGCTGGGTAAACAAGAAGTTATTCGCGGTTGGGAAGAG
                    GGTGTTGCACAGATGAGCGTTGGTCAGCGTGCAAAACTGAC
                    CATTTCACCGGATTATGCCTATGGTGCAACCGGTCATCCGG
                    GTATTATTCCGCCTCATGCAACCCTGGTTTTTGATGTTGAAC
                    TGCTGAAACTGGAAGGTGGTAGCGGTGGTGGTGGTTCTGGT
                    GGTAGCAGCTCAGGTGGTGTTACCGGTTATCGTCTGTTTG
                    AAGAAATTCTGTAA

Vesicle Preparation: Throughout this study, vesicles were prepared via the thin film hydration method. Briefly, lipid was deposited into a glass vial and dried with a stream of nitrogen and placed under vacuum for 3 hours. Films were then rehydrated in Milli-Q water and heated at 60° C. for a minimum of 3 hours, and up to overnight. Vesicles were then briefly vortexed and extruded 21× through a 100 nm polycarbonate filter.

Analysis of folding and insertion of cell-free expressed proteins into synthetic membranes: Protein expression was performed with the PURExpress In Vitro Protein Synthesis kit (E6800, NEB) according to the manufacturer's instructions. 30 μL reactions were assembled with a final concentration of 10 mM of lipid and 3.3 nM plasmid. Reactions were allowed to progress at 37° C. for 3 hours. GFP folding and fluorescence was monitored using a Molecular Devices Spectra Max i3 plate reader (ex 480 nm, em. 507 nm). Increase in GFP fluorescence was then calculated by subtracting the fluorescence at t=0 from the fluorescence at t=3 hours.

Protein expression was measured via western blot. Cell-free protein synthesis reactions were spun at 20,000 g for 10 minutes to pellet and remove uninserted protein. The supernatant was collected and run on a 12% Mini-PROTEAN TGX Precast Protein Gel (Bio-Rad) for all experiments, except the truncation experiments. For truncation experiments, samples were run on a 16.5% Tricine Mini-PROTEAN Precast Protein Gel to enhance the separation of smaller protein products. Wet transfer was performed onto a PVDF membrane (Bio-Rad) for 45 min at 100 V. Membranes were then blocked for an hour at room temperature in 5% milk in TBST (pH 7.6: 50 mM Tris, 150 mM NaCl, HCl to pH 7.6, 0.1% Tween) and incubated for 1 hour at room temperature or overnight at 4° C. with primary solution (anti GFP, diluted 1:1000 in 5% milk in TBST). Primary antibody solution was decanted, and the membrane was washed three times for 5 minutes in TBST and then incubated in secondary solution at room temperature for 1 hour (HRP-anti-Mouse (CST 7076) diluted 1:3000 in 5% milk in TBST). Membranes were then washed in TBST and incubated with Clarity Western ECL Substrate (Bio-Rad) for 5 min. Membranes were then imaged in an Azure Biosystems c280 imager and bands were quantified with ImageJ.

Preparation of Giant Unilamellar Vesicles: Giant, micron sized, vesicles were prepared via electroformation using the Nanion Vesicle Prep Pro (Nanion Technologies) standard vesicle preparation protocol. To visualize protein, proteins were expressed into liposomes containing 0.1 mol % 18:1 PC Cy5.5. Following expression, liposomes were diluted to 1 mM and 10 μL were deposited onto indium tin oxide slides and allowed to dry under vacuum for 30 minutes. Samples were then rehydrated with 290 mOsm sucrose. To visualize domains, 10 mM mixtures of lipid in chloroform were prepared with 0.1 mol % Rhod-PE. 10 μL of each solution was then drop-casted onto indium tin oxide slides and placed under vacuum for 20 minutes to eliminate solvent and rehydrated with 290 mOsm sucrose. GUVs were observed under a Nikon confocal microscope. Glass bottomed Lab-Tek II microscope chambers (Thermo Fischer) were used to image GUVs. 200 μL of bovine serum albumin was placed into each chamber and allowed to sit for 30 min. Each well was then washed with 290 mOsm PBS and 1 mL of 1 mM of GUVs were added to 250 mL of PBS and allowed to settle in each chamber. A 20× objective was used to visualize vesicles. Images were analyzed using NIS software.

Calcein Leakage: Vesicles were rehydrated with 50 mM Calcein in 10 mM HEPES. Calcein vesicles were purified using a size exclusion column packed with Sepharose 4B immediately before experimentation. PURExpress reactions were then assembled and calcein leakage was read (ex. 480 nm/em. 520 nm) on the plate reader (Molecular Devices Spectra Max i3) for 3 hours at 37° C. 1% Triton-X was then added to achieve a maximum dequenching of calcein, which served as the fluorescence intensity for 100% mixing. Percent content mixing was calculated using the following equation:

$$\% \text{ Calcein Release} = 100 \cdot \frac{I_{t=3 \, hr} - I_{t=0 \, hr}}{I_{triton} - I_{t=0 \, hr}}$$

where $I_{t=0hr}$ is the initial fluorescence intensity, It=3 hr is the fluorescence intensity at 3 hours, and $I_{triton}$ is the fluorescence intensity after the addition of Triton-X. To determine the relative calcein release per protein, western blots were performed on samples. Calcein release values were then divided by total protein intensity for each sample to calculate the calcein release relative to protein expression.

Assessing protein sorting between distinct compartments via immunoprecipitation: 100 nm 14:1 and 22:1 PC vesicles were prepared as outlined above with 0.1 mol % 18:1 PC Cy5.5 and 18:1 PC Rhodamine respectively. PURExpress reactions were assembled with 3.3 nM plasmid encoding either the 20, 24, 40, or 50 Å pore protein and 5 mM each of 14:1 and 22:1 PC vesicles. Reactions were allowed to progress at 37° C. for 3 hours. Samples were then incubated with Pacific-blue anti-flag antibody conjugated protein A/G beads for 1 hour at room temperature. Samples were washed 3 times and then analyzed via flow cytometry. Beads were gated for size (only larger beads were selected to eliminate unbound vesicles) and anti-flag antibody (405 nm excitation, 450/50 nm emission). Beads were analyzed for Rhodamine (550 nm excitation, 582/15 nm emission) and Cy5.5 (640 nm excitation, 730/45 nm emission with 685 longpass filter). At least 10,000 events were recorded, and beads were re-gated in FlowJo (TreeStar).

Figure 11A:
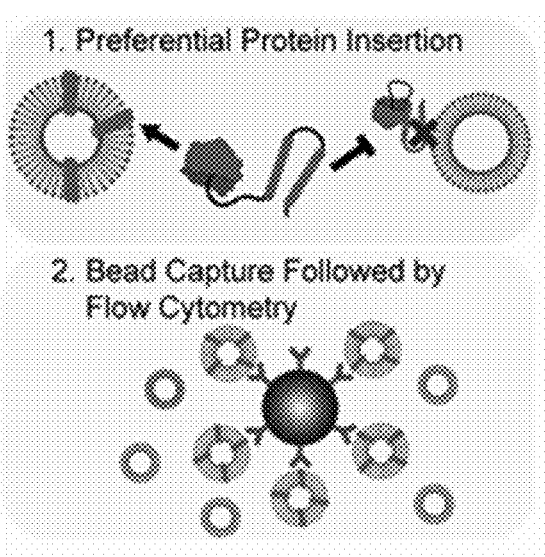
FIG. 11A-11G.
Figure 11B:
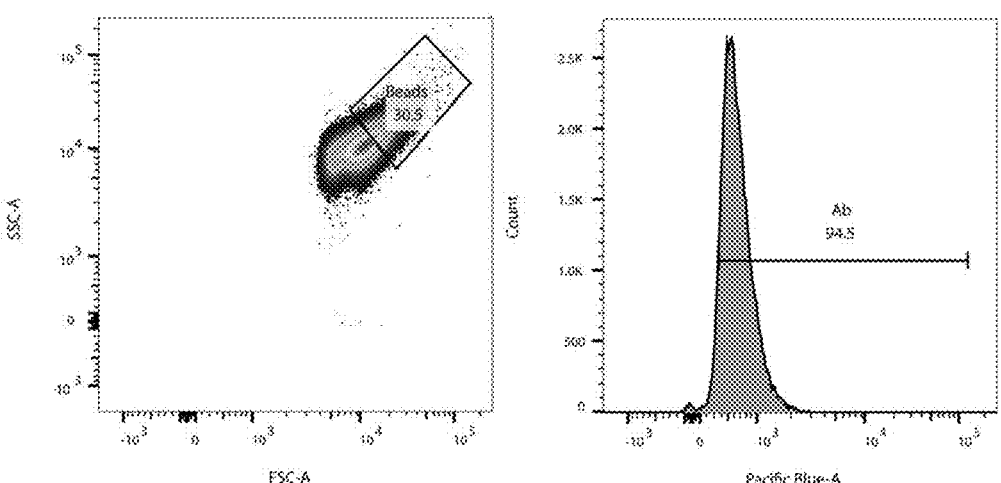
Figure 11C:
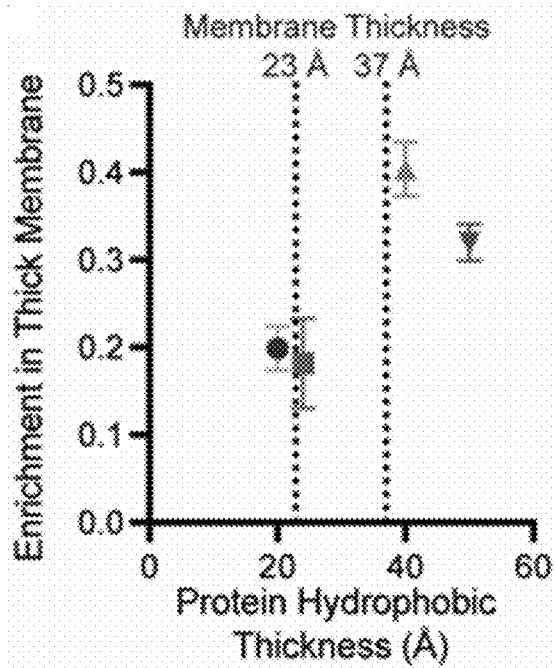
Figure 11D:
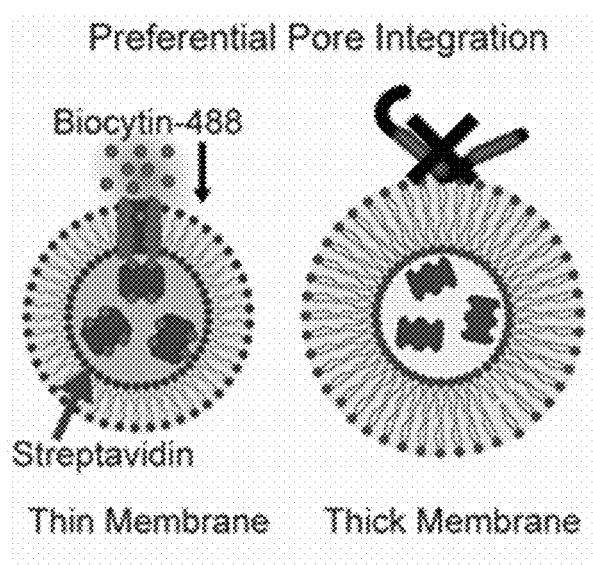
Figure 11E:
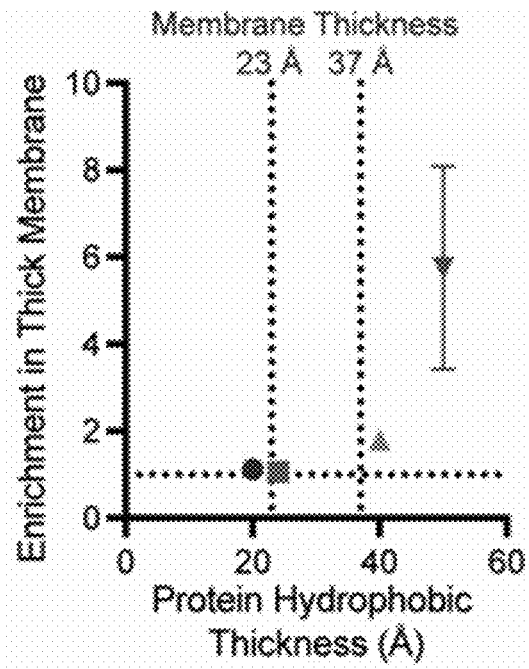
Figure 11F:
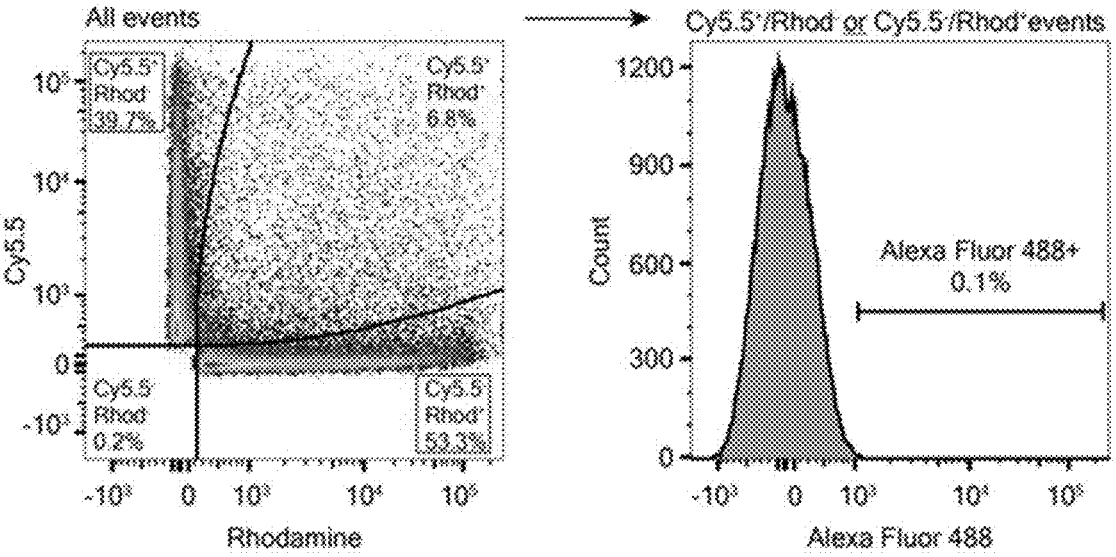
Figure 11G:
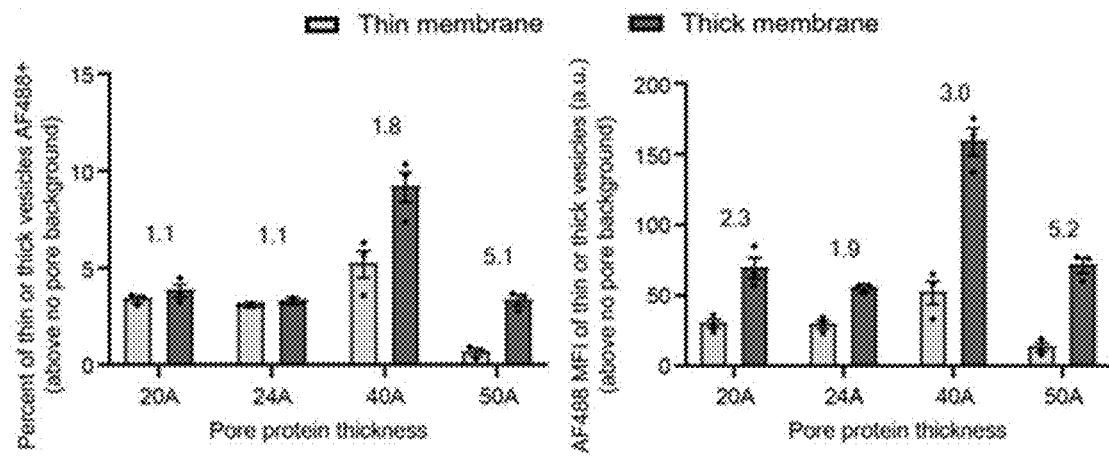

Analyzing differential pore activity: 14:1 and 22:1 PC vesicles were prepared as outlined above with 0.1 mol % 18:1 PC Cy5.5 and 18:1 PC Rhodamine respectively. Lipid films were rehydrated with 5 µM streptavidin and extruded to 1 µm. PURExpress reactions were assembled with 3.3 nM plasmid encoding either the 20, 24, 40, or 50 Å pore protein and 5 mM each of 14:1 and 22:1 PC vesicles and incubated at 37° C. for 3 hours. Reactions were then purified via size exclusion chromatography to purify away unencapsulated streptavidin. Vesicles were incubated with 1 µM biocytin conjugated Alexa Fluor 488 for 24 hours. Samples were diluted to a lipid concentration of 1 µM in PBS and analyzed via flow cytometry on a BD LSR Fortessa Special Order Research Product (Robert H. Lurie Cancer Center Flow Cytometry Core). Alexa Fluor 488 was excited with a 488 nm laser and captured with a 505 nm long pass filter and a 530/30 nm bandpass filter, Rhodamine was excited with a 552 nm laser and captured with a 582/15 nm bandpass filter, and Cy5.5 was excited with a 640 nm laser and captured with a 685 nm longpass filter and a 730/45 nm bandpass filter. Events on the cytometer were thresholded on the presence of either Rhodamine or Cy5.5 detection to identify vesicles, and approximately 100,000 events were captured per reaction. Data was analyzed in FlowJo v10.8 and spectrally compensated. Samples were gated using curly quad gating of Rhodamine versus Cy5.5 to isolate single-dye positive events and thus restrict analysis to only thin or thick membrane vesicles (FIG. 11F-G). Curly quad gating (rather than quad gating) was necessary to account for photon counting and measurement error at high laser settings (40). Single lipid-dye positive events were then gated for Alexa Fluor 488 using samples containing vesicles but no Alexa Fluor 488. The percent of thin and thick vesicles identified as Alexa Fluor 488 positive and the mean fluorescent intensity (MFI) of each vesicle population was determined and analyzed. Vesicles that were prepared as above but that did not have a protein pore (i.e., the PURExpress reaction did not have pore-encoding DNA) was used to determine background. This background signal (e.g., percent positive vesicles or MFI) was subtracted as part of the data analysis process.

Lipid-Protein FRET experiments: Vesicles composed of DOPC or 42.5 mol % 14:1 PC/27.5 mol % DPPC/30 mol % cholesterol were prepared with 0.1 mol % 18:1 PC Rhodamine as outlined above. PURExpress reactions were prepared with 10 mM vesicles and 3.3 nM plasmid encoding the 20, 24, 40, or 50 Å hairpin proteins with a C-terminal SNAP tag. Reactions were performed at 37° C. for 3 hours. Samples were then incubated with 10 µM Alexa Fluor-SNAP substrate for 30 minutes at 37° C. Vesicles were purified away from free SNAP substrate via size exclusion chromatography. Vesicles were collected and FRET was measured using an Agilent Cary Eclipse Fluorescence Spectrophotometer by exciting the samples at 488 nm and recording the emission at 520 and 590 nm. Fluorescence measurements were recorded at temperatures ranging from 25 to 47° C. Vesicle samples were then treated with trypsin and 0.1% Triton X to disrupt vesicles and SNAP conjugated dye.

Relative FRET, noted here as $C_D/C_H$, was calculated using the following equation:

$$C_D/C_H = \ln\left(\frac{F}{F_o}\right)D/\ln\left(\frac{F}{F_o}\right)H$$

where F is the fluorescent intensity of donor in the presence of acceptor, $F_o$ is the fluorescent intensity of donor after the addition of trypsin and Triton-X. D denotes samples with domain forming membrane and H denotes samples with homogenous membranes. With this convention, $C_D/C_H$ will be high if Rhodamine (acceptor) and protein (donor) partition into the same lipid domain and low if they are segregated into different lipid domain (41).

NanoBit Experiments: Vesicles composed of DOPC or 42.5 mol % 14:1 PC/27.5 mol % DPPC/30 mol % Cholesterol were prepared as outlined above and extruded to 100 nm. PURExpress reactions were assembled with 1.7 nM of each DNA construct: 20 Å Hairpin/50 Å Hairpin, 20 Å Hairpin/20 Å Hairpin, 50 Å Hairpin/50 Å Hairpin. Reactions were allowed to progress for 3 hours at 37° C.

For rapamycin experiments, cell-free reactions were split into two and either rapamycin in DMSO or DMSO only was added to protein incorporated vesicles at a final concentration of 30 nM (or a DMSO mol fraction of 1 mol lipid: 0.0015 mol rapamycin). Samples were incubated for 2 hours at room temperature. NanoBiT reactions were setup using the Promega Nano-Glo Live Cell Assay System following the Technical Manual with minor modifications. Cell free reactions were diluted 1:4 in 1×PBS and the Nano-Glo Substrate was used at a 50× final dilution of the stock. Luminescence was read using a Molecular Devices Spectra Max i3 plate reader at room temperature for 10 minutes. To ensure the ratios of NanoBit to Substrate were in optimal range, luminescence was checked to be constant over the ten-minute read. Rapamycin induced luminescence was then calculated as:

$$\text{Rapamycin Induced Lum.}=\text{Luminesence}_{+Rap}/\text{Luminesence}_{-Rap}$$

where $\text{luminescence}_{+Rap}$ is the measured luminescence in the presence of rapamycin and $\text{luminescence}_{-Rap}$ is the measured luminescence in the presence of DMSO only.

To characterize protein-protein interactions with increasing temperature, the luminescence of samples was then recorded at varying temperatures from room temperature to 45° C. Relative NanoBit assembly was then calculated as:

$$\text{Relative NanoBit Assembly}=\text{Lum.}_{20\text{ Å-50 Å}}/0.5*(\text{Lum}_{20\text{ Å-20 Å}}+\text{Lum}_{50\text{ Å-50 Å}})$$

where $\text{Lum.}_{20\text{ Å-50 Å}}$ is the luminescence of samples with 20 Å and 50 Å hairpin proteins, $\text{Lum.}_{20\text{ Å-20 Å}}$ is the luminescence of samples with 20 Å and 20 Å hairpin proteins, and $\text{Lum.}_{50\text{ Å-50 Å}}$ is the luminescence of samples with 50 Å and 50 Å hairpin proteins. Luminesce values were then normalized to the luminesce value at room temperature. Dividing by the average of NanoBit fused to proteins of the same length allows for the increase in Nanobit assembly due to increases in lipid and protein mixing as systems with the same TMDs should reside in the same lipid domains.

Furthermore, this normalization accounts for luminescence differences due to temperature.

Figures 2A, 2B, 2C, 2D, 2E:
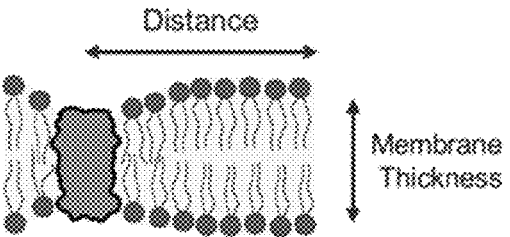
FIGS. 2A-2E illustrate the deforming of membranes to accommodate hydrophobic mismatch.

Example 2—Minimizing Hydrophobic Mismatch Maximizes Cell-Free Expression of Membrane Proteins into Synthetic Membranes The effect of hydrophobic mismatch on co-translational insertion of de novo designed hairpin proteins was assessed. Interactions between de novo designed membrane proteins of varying hydrophobic thicknesses and synthetic membranes is illustrated in FIG. 1A. Molecular dynamics (MD) simulations of proteins in a thin, medium, and thick lipid system were performed and membrane thickness as a function of distance from the protein was measured. FIG. 2A illustrates the measurements that were taken. As shown in FIGS. 2B, 2C, and 2D computationally probing membrane thickness as a function of distance from an inserted 20 Å, 28 Å, and 50 Å protein, respectively, revealed that membranes must deform more to accommodate larger hydrophobic mismatch. The horizontal line represents the hydrophobic thickness of the protein. Data represented in FIG. 2D was generated by subtracting the membrane thickness at 70 Å from the membrane thickness at 10 Å from the protein center. FIG. 2E shows datapoints derived from simulations of the 20, 28, and 50 Å proteins for the three membrane compositions (thin, medium, and thick). The membrane compression positively correlated with hydrophobic mismatch. Together, the results illustrate that membranes deform close to the protein insertion site, deforming more as hydrophobic mismatch increases.

Figure 3A:
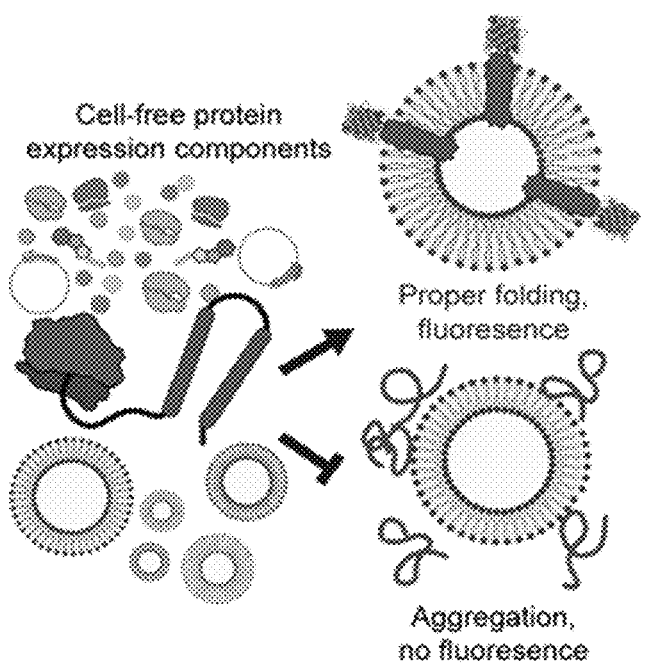
FIG. 3A is a schematic illustrating exploration of the effect of hydrophobic mismatch on protein expression and folding in a cell-free protein synthesis system using mEGFP as a folding reporter.
Figure 3B:
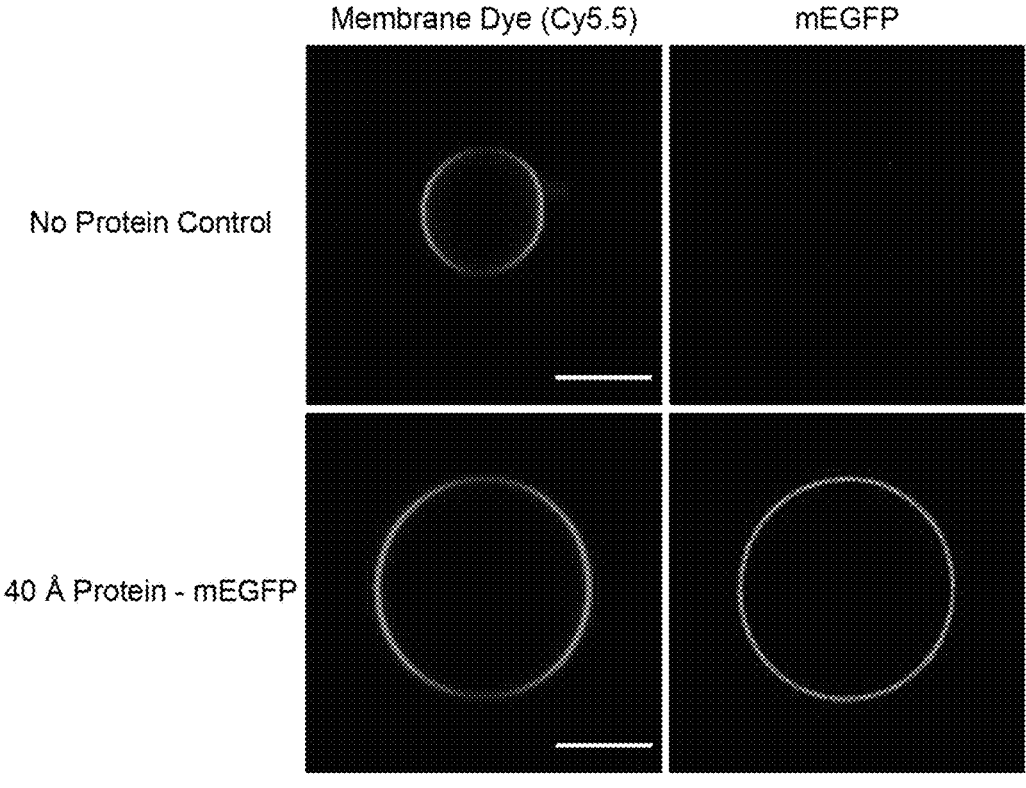
FIG. 3B shows confocal microscopy images showing membrane protein insertion into synthetic membranes.

The impact of hydrophobic mismatch on protein expression was then examined in vitro. Plasmids encoding hairpin proteins were designed. A C-terminal monomeric-enhanced green fluorescence protein (GFP) allowed for monitoring expression and proper folding of proteins by GFP fluorescence (18, 19). By adding a plasmid encoding a membrane protein and pre-assembled phospholipid vesicles to a cell-free protein synthesis system, expression and cotranslational insertion of the designed proteins into synthetic membranes of the vesicles could be tracked. The experimental design is illustrated in FIG. 3A. mEGFP was used as a folding reporter. Shown in FIG. 3B, giant unilamellar vesicles (GUVs) were prepared with Cy5.5 conjugated lipid (left column) and observed using confocal microscopy. When proteins were expressed into synthetic lipids, GFP localized to the membrane, indicating membrane protein insertion and folding (right column). Pictured is the 40 Å protein in a DOPC membrane. Scale bar 10 μm.

Proteins were expressed in the presence of no membrane or a thin, medium, or thick lipid membrane to match the simulations. Protein folding was monitored via GFP fluorescence and protein expression was measured via western blots. As illustrated in FIGS. 4A and 4B, the GFP fluorescence data shows that all designed proteins expressed poorly in the absence of vesicles, suggesting that their enhanced expression in the presence of membranes is due to co-translational protein folding and insertion into synthetic membranes. Also, protein expression was maximized in hydrophobically matched membranes. Values represent the mean of 3 independent replicates, normalized to the maximum increase in fluorescence for each protein construct. The data in FIG. 4B is plotted as a bar graph to display error in FIG. 4C. Increase in GFP fluorescence was normalized to the maximum increase for each construct. n=3, error bars represent S. E. M. FIG. 4D illustrates Western plots performed on the samples represented in FIG. 4B-C. Protein band intensity was normalized to the most intense band for each construct. n=3, error bars represent S. E. M. When comparing the expression of each protein in the presence of the three lipid systems, it was found that expression and proper folding was generally maximized when membrane-protein hydrophobic mismatch was minimized for each studied protein Furthermore, GFP fluorescence, determined experimentally, correlated linearly with membrane compression, determined computationally (MD simulation), as illustrated in FIG. 4E. Together, these data demonstrate that membrane-protein hydrophobic mismatch inhibits membrane protein expression.

Figure 5:
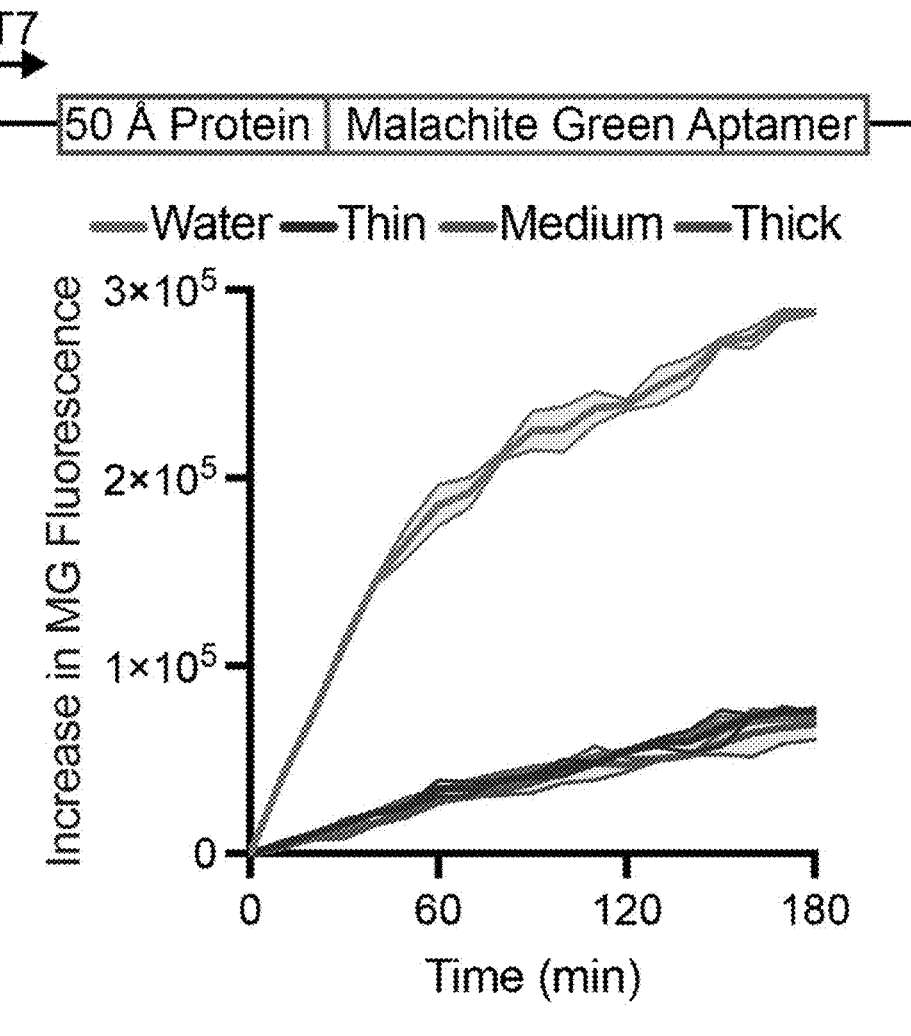
FIG. 5 illustrates transcription of the 50 Å protein as a function of membrane-protein hydrophobic mismatch.
Figure 7:
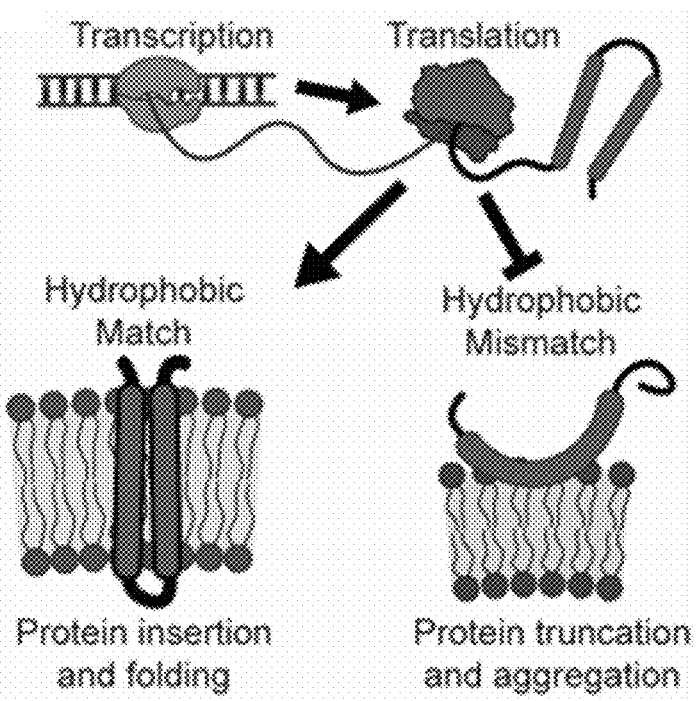
FIG. 7 is a schematic of cell-free protein expression of proteins into membranes of different hydrophobic thicknesses.

Next, the effects of hydrophobic mismatch on transcription and translation were examined. Transcription was measured by adding the DNA sequence for the malachite green aptamer immediately after the gene encoding the 50 Å protein. As the aptamer is transcribed, it binds to malachite green and dye fluorescence increases (20). The presence of vesicles inhibited transcription of the 50 Å protein; however, no significant differences in malachite green fluorescence were observed between the three lipid systems suggesting that hydrophobic mismatch does not measurably affect transcription (FIG. 5, n=3, error bars represent S. E. M.) (18). To characterize how translation is affected by membrane-protein hydrophobic mismatch, an N-terminal FLAG tag was added to the 50 Å protein to monitor the formation of both full-length and truncated protein products. The construct is illustrated in FIG. 6A. The construct was expressed in the presence of water, 14:1 PC, 18:1 PC, and 22:1 PC, and protein formation was assessed via western blot (FIG. 6B). The intensity of the full-length product and truncation products was measured using ImageJ and the ratio of full-length to truncation product intensity was plotted in FIG. 6C. FIG. 6D shows the uncropped western blot for all replicates displayed in FIG. 6B. Together, analysis of the expression of 50 Å by western blot showed an increase in incomplete protein products relative to full-length protein as a function of hydrophobic mismatch. The higher proportion of truncated protein products in hydrophobically mismatched systems suggests that translation is affected by hydrophobic mismatch. Without being bound by any particular theory, it is believed that this effect arises from the energy cost of deforming membranes to accommodate differences in hydrophobic mismatch, which reduces the probability of protein co-translational insertion and proper folding. Misfolded proteins may capture nascent proteins from the ribosome, thus reducing the rate of protein insertion and folding, and increasing the frequency of incomplete translation. FIG. 7 is a schematic of cell-free protein expression of proteins into membranes of different hydrophobic thicknesses. Proteins insert and fold best into hydrophobically matched membranes.

Figure 8A:
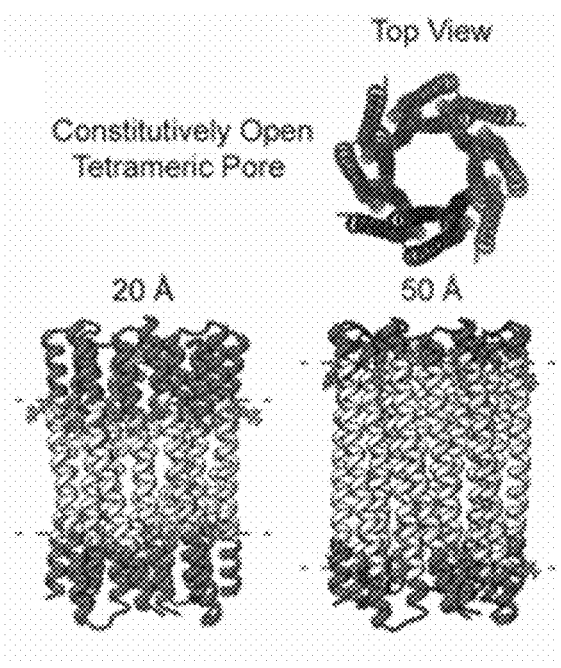
FIG. 8A illustrates the design of constitutively open pore proteins.
Figure 8B:
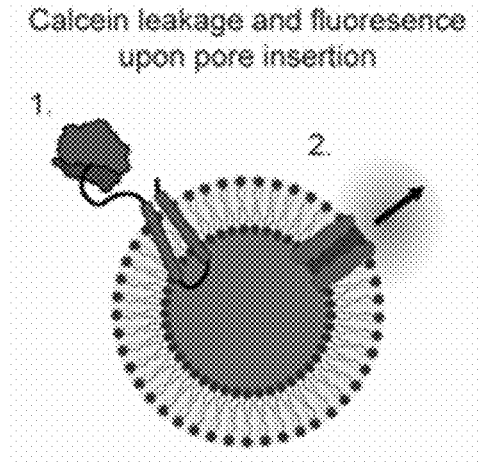
FIG. 8B illustrates assessment of proper folding and insertion of pore proteins via calcein leakage.

Example 3—Protein-Lipid Hydrophobic Matching can be Used to Organize Proteins Between Membranes and Impart Differentiated Functionality The differential expression and integration of membrane proteins into membranes of different thicknesses raised the possibility that this physical phenomenon could be used to enrich select populations of vesicles with a membrane protein in one pot. Based on the designs discussed above, transmembrane pore proteins with a constitutively open 10 Å pore and with hydrophobic thicknesses ranging from 20 to 50 Å were created (FIG. 8A) (16). To validate that pore proteins inserted into membranes, they were expressed in the presence of vesicles encapsulating calcein, a self-quenching dye (FIG. 8B). Upon expression of pore proteins, calcein leakage and increased fluorescence were observed (21).

Figure 9:
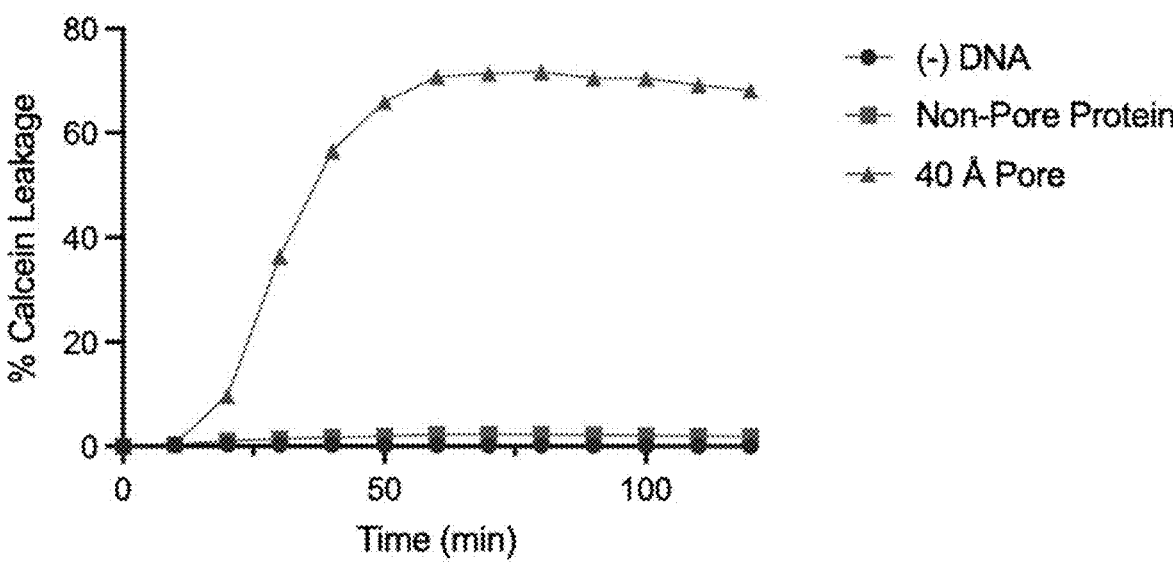
FIG. 9 illustrates the release of calcein dye after expression and insertion of transmembrane pore proteins.

First, it was confirmed that calcein leakage was specific to pore insertion. 50 mM calcein, a self-quenching dye, was encapsulated into DOPC vesicles. The vesicles were then added to a cell free reaction without DNA, or with DNA encoding the 40 Å hairpin or pore protein. As shown in FIG. 9, upon expression and insertion of the 40 Å pore protein, fluorescence increased due to calcein leakage and subsequent dequenching. This demonstrates that calcein leakage is specific to pore protein expression and integration into vesicle membranes, and not due to interactions with PUR-Express or insertion of non-pore proteins.

Figure 10:
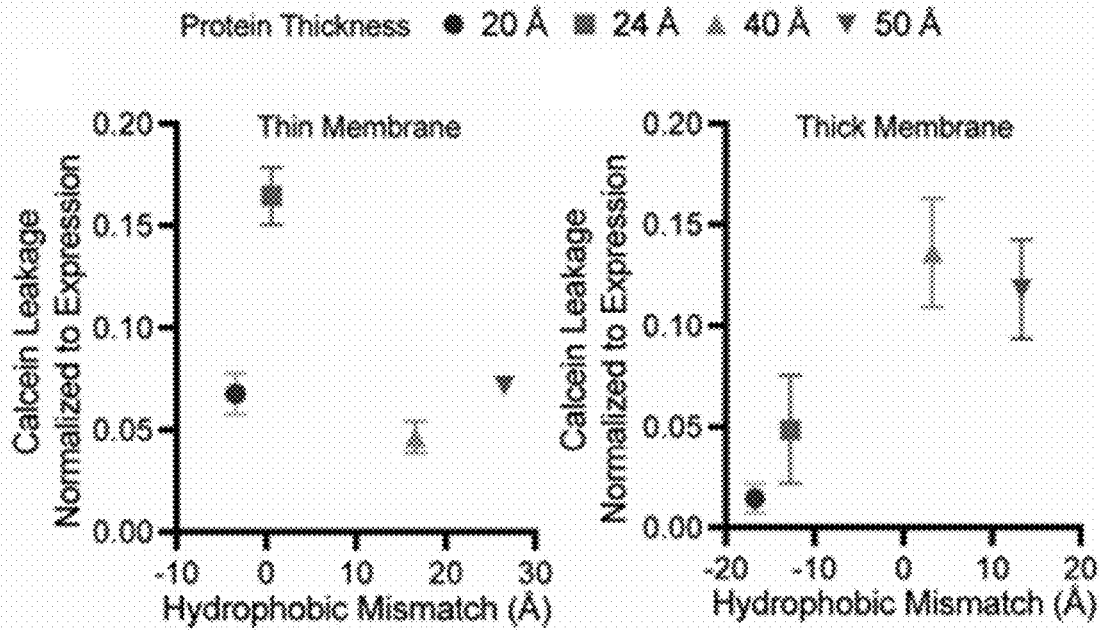
FIG. 10 illustrates calcein leakage through de novo designed channel proteins is thin (left panel) and thick (right panel) membranes.

The pores were then expressed in the presence of vesicles with thick or thin membranes, encapsulating calcein. When normalized by protein expression, as determined by western blot, hydrophobically matched proteins released the most amount of calcein (FIG. 10). This result demonstrates that reducing hydrophobic mismatch between the designed pore proteins and membranes maximizes the functional incorporation of membrane proteins. All experiments were performed 3 times, error bars represent the S. E. M.

Next, the extent of protein expression and folding of a single protein (20, 24, 40, or 50 Å in hydrophobic thickness) into thick and thin membranes (37 and 23 Å respectively) when both membranes were present within one reaction was assessed. To evaluate differential integration, a flow cytometry-based assay was developed in which each set of vesicles was labeled with an orthogonal lipid conjugated dye and each protein contained a C-terminal FLAG tag. Proteins were expressed in the presence of the vesicles and were collected with anti-FLAG antibody-conjugated beads. The beads were analyzed by flow cytometry and read for colocalized vesicle fluorescence, which is expected occur by way of interactions of membrane-integrated proteins with the beads (FIG. 11A). FIG. 11B shows the gating strategy for the sorting assays. Beads were first gated on sizes (left panel) to analyze larger beads and reduce analysis of unbound vesicles, then gated by the presence of antibody (right panel). As illustrated in FIG. 11C, the ratio of fluorescence from the thick membranes to the thin membranes that was colocalized to the beads was monitored and, as hydrophobic thickness of a protein increased, the fluorescence ratio increased. The vertical dotted lines correspond to membrane hydrophobic thickness. The results indicate that proteins preferentially fold into hydrophobically matched membranes and that protein enrichment in one population of membranes can be increased relative to another vesicle population by minimizing hydrophobic mismatch. All experiments were performed 3 times, error bars represent the S. E. M.

The capacity of hydrophobic mismatch to assemble vesicles with a distinct functionality, particularly enhanced permeability, due to preferred integration of membrane proteins was explored. Membrane permeability to a biotinylated fluorophore (~1 kDa)(16) was measured. Streptavidin was encapsulated in the lumen of thick and thin membranes, each labeled with a distinct lipid-conjugated fluorescent dye. Proteins of different hydrophobic thicknesses were expressed in the presence of both vesicles, free streptavidin was purified away, and the vesicles were then incubated with biocytin conjugated AlexaFluor 488. Biocytin entry into vesicles, which should vary as a function of the number of functional pores in each vesicle membrane, was monitored via vesicle-localized biocytin fluorescence since biocytin cannot leave the vesicles after it is bound to streptavidin in the vesicle lumen, as illustrated in FIG. 11D. To selectively deliver cargo in a mixed vesicle population, pore proteins were expressed in the presence of thick and thin membranes, encapsulating streptavidin. Following protein expression, vesicles were incubated with AF488-biocytin, which could enter vesicles following pore integration. The amount of dye that was delivered to each population of vesicles was measured by flow cytometry and the ratio of thick and thin vesicles encapsulating AlexaFluor 488 was compared. As shown in FIG. 11E, as protein hydrophobic thickness increased, the ratio increased, suggesting that the population of vesicles to which biotin-AlexaFluor 488 was preferentially delivered could be tuned by biasing protein integration into hydrophobically matched vesicles membranes. The vertical dotted lines correspond to membrane hydrophobic thickness. All experiments were performed 3 times, error bars represent the S. E. M. FIGS. 11F and G show the gating strategy and population metrics for pore permeability flow data presented in FIG. 11E. Thin and thick membrane vesicles were labeled with a single membrane dye, either Cy5.5 or Rhodamine, respectively. As shown in FIG. 11F, to analyze subsequent flow cytometry data, events were first gated via a curly quad gating strategy. This identified vesicle populations with only a single membrane dye (left image, top left gate and bottom right gate). A negative control sample without Alexa Fluor 488 dye was used to set the threshold for an Alexa Fluor 488 (AF488) positive signal (right). This gate was then applied to single positive vesicle populations to determine Alexa Fluor 488AF488 signal as a measure of functional protein pore insertion. FIG. 11G shows the population level metrics of the data presented in FIG. 11E. The left panel depicts the percentage of vesicles with a single membrane dye that are also AF488 positive per the gating strategy in FIG. 11F for different protein pore thicknesses. The right panel depicts the AF488 mean fluorescence intensity (MFI) of vesicles with a single membrane dye for a given pore protein thickness (i.e., the MFI is calculated from samples gated per only the left image in FIG. 11F. In both cases, the data are background subtracted; the background was determined from vesicles incubated with biocytin but not a co-expressed pore protein. Data points represent the three replicates for each condition, the bar graphs represent the mean, and the error bars represent the standard deviation. The numbers are ratios of thick membrane average to thin membrane average for a given metric and pore protein thickness. Together, these data suggest that membrane compartments can be enriched with distinct protein content and therefore endowed with distinct function by modulating lipid-protein hydrophobic mismatch. The results highlight the capacity of protein-membrane hydrophobic mismatch alone to organize proteins between distinct membranes in vitro and suggest a route to engineer more complex membrane-based materials, such as differentiated-nested vesicles or synthetic organelles.

Example 4—Hydrophobic Mismatch Coupled with Phase Separating Lipid Mixtures Controls Protein-Protein Interactions within a Single Membrane The lateral organization of membrane proteins in a single membrane is important to control protein-protein and protein-lipid interactions and subsequent signaling activity (7, 22). This organization arises due to different lipid-lipid, lipid-protein, and cytoskeletal interactions. While the functional relationship between protein organization and signaling has been explored in cellular contexts, it had not yet been recapitulated in vitro. Demonstrating this organization experimentally was critical to identify the molecular and physical origin of these interactions. Doing so uncovers the extent to which protein and lipid driven organization may enable protein organization in cells, and also provides a route to design more complex sensing and signaling modalities within membrane-based materials.

Previous work has demonstrated that peptides can be laterally organized through membrane ordering in unsaturated lipid systems (23) and that beta-barrel proteins can associate with liquid-ordered lipid phases through the modulation of protein hydrophobic thickness (24). However, contradicting phase behavior of proteins in cellular, in silico, and synthetic membranes has been noted (25, 26), likely due to the use of microdomain forming lipid mixtures in synthetic lipid systems, which are more ordered than biological membranes, hindering protein association with ordered lipid phases. It was hypothesized that by designing membranes just above a lipid demixing transition, like biological membranes (27), an induction of lipid domains induced by local changes in curvature or hydrophobic thickness around membrane components, such as proteins (28-30), could be observed.

Figure 12:
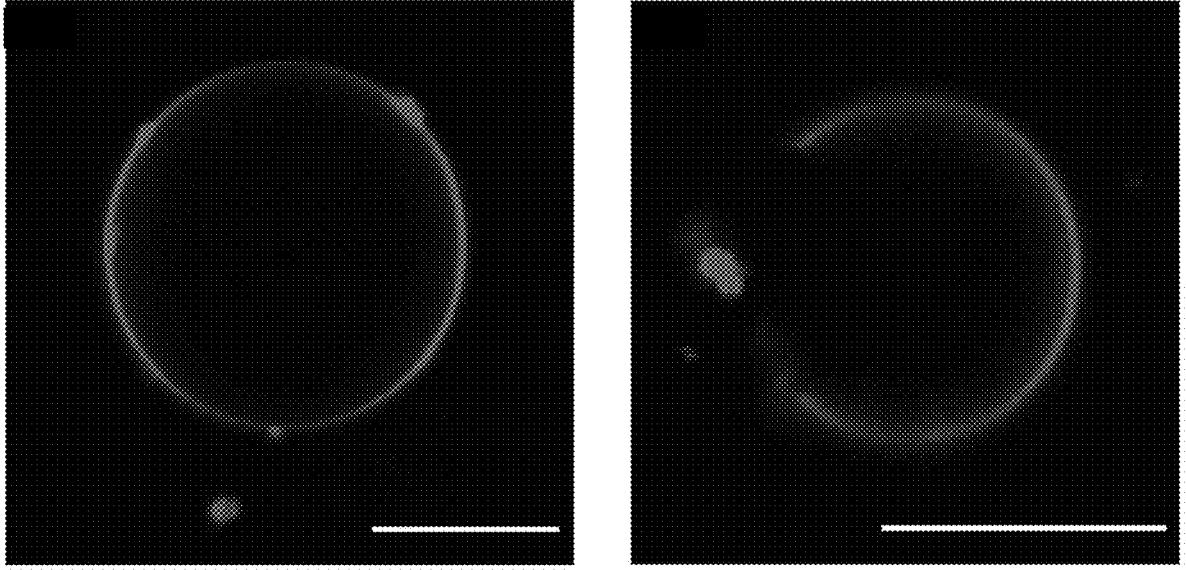
FIG. 12 shows fluorescent microscopy of giant unilamellar vesicles.

To examine the ability of hydrophobic mismatch to affect protein location and protein-protein interactions in a single membrane, the way that single proteins co-localize with lipid components based on hydrophobic mismatch was characterized. Membranes were prepared with a shorter unsaturated lipid, 14:1 PC, a thicker saturated lipid, DPPC (16:0 PC), and cholesterol. This combination of lipids is prone to phase separation and, at different lipid ratios, can form homogenous and phase separated membranes (31). A lipid composition just above a demixing transition was chosen (25, 26, 32) (FIG. 12). Fluorescent microscopy images of giant unilamellar vesicles are shown in FIG. 12. In the left image, vesicles were composed of 42.5 mol % 14:1 PC/27.5 mol % DPPC/30 mol % Chol (composition used in this study). In the right image, the vesicles were composed of 40 mol % 14:1 PC/40 mol % DPPC/20 mol % Chol. The membranes were labeled with 0.1 mol % 18:1 PC Rhodamine, which localized to the lipid disordered phase. Absence of dye, as seen in the right panel, indicates the presence of microdomain formation, a property often selected in previous studies. By increasing the cholesterol content and decreasing the amount of DPPC, membranes that do not exhibit microdomain formation were formed, as shown in the left panel. Samples with higher cholesterol content do not exhibit microdomain formation. Scale bars are 10 μm.

Figure 13:
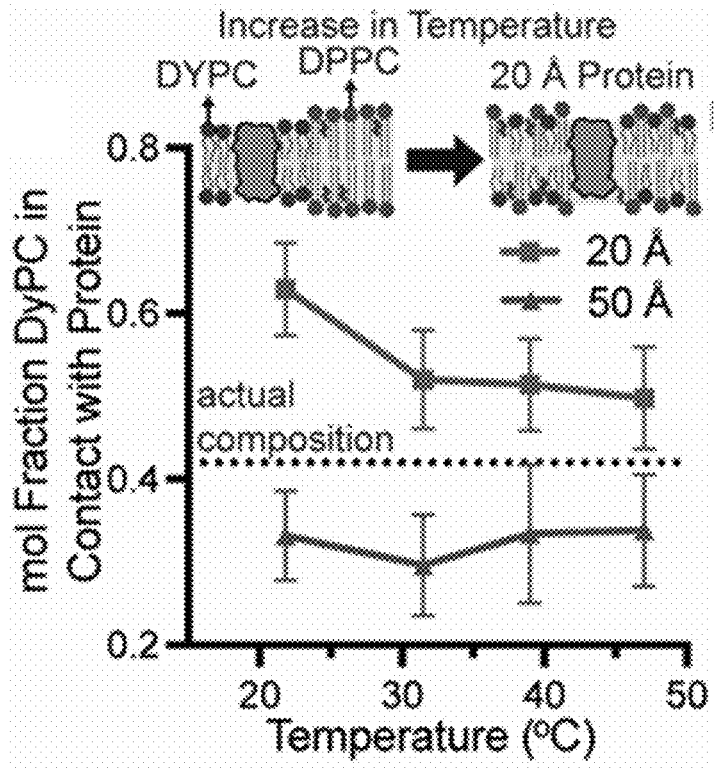
FIG. 13 illustrates MD simulations of 20 Å and 50 Å hairpin protein interaction with DyPC lipids.

Membrane interactions with thin (20 Å) and thick (50 Å) proteins were simulated using coarse-grained MD simulations of lipid composition comparable to the experimental system. It was observed that insertion of membrane proteins into an initially homogenous lipid mixture induced lipid reorganization. As shown in FIG. 13, distinct lipid-protein domains formed: a domain rich in thinner, unsaturated lipid (DyPC) appeared around the 20 Å protein and a domain rich in the thicker, saturated lipid (DPPC) appeared around the 50 Å protein over time. The effect of increasing temperature was studied as a means to dissolve lipid-protein domains, as saturated and unsaturated lipids become more miscible at elevated temperatures (31). As temperature increased, protein-lipid contacts converged toward the average composition of the membrane (FIG. 13). The dotted line indicates the actual composition of DyPC, 42.5 mol %. Experiments were performed 3 times, error bars represent the S. E. M.

Lipid-protein FRET (fluorescence resonance energy transfer) was used to assess how proteins were organized in the membranes. To accomplish this, rhodamine dye conjugated to 18:1 PC, which localizes with shorter, unsaturated lipids, was added into the membranes; and a C-terminal SNAP tag was fused to each protein, allowing conjugation of AlexaFluor 488.

Using FRET between SNAP Alexa Fluor 488 and the lipid-conjugated rhodamine dye, the local concentration of rhodamine around the protein in domain forming membranes (14:1 PC/DPPC/Chol) compared to homogenous membranes (DOPC), could be calculated. This is represented as $C_D/C_H$:

$$C_D/C_H = \ln\left(\frac{F}{F_o}\right)D/\ln\left(\frac{F}{F_o}\right)H,$$

wherein F is the fluorescent intensity of donor in the presence of acceptor, $F_o$ is the fluorescent intensity of donor after the addition of trypsin and Triton-X. D denotes samples with domain forming membrane and H denotes samples with homogenous membranes.

Figure 14A:
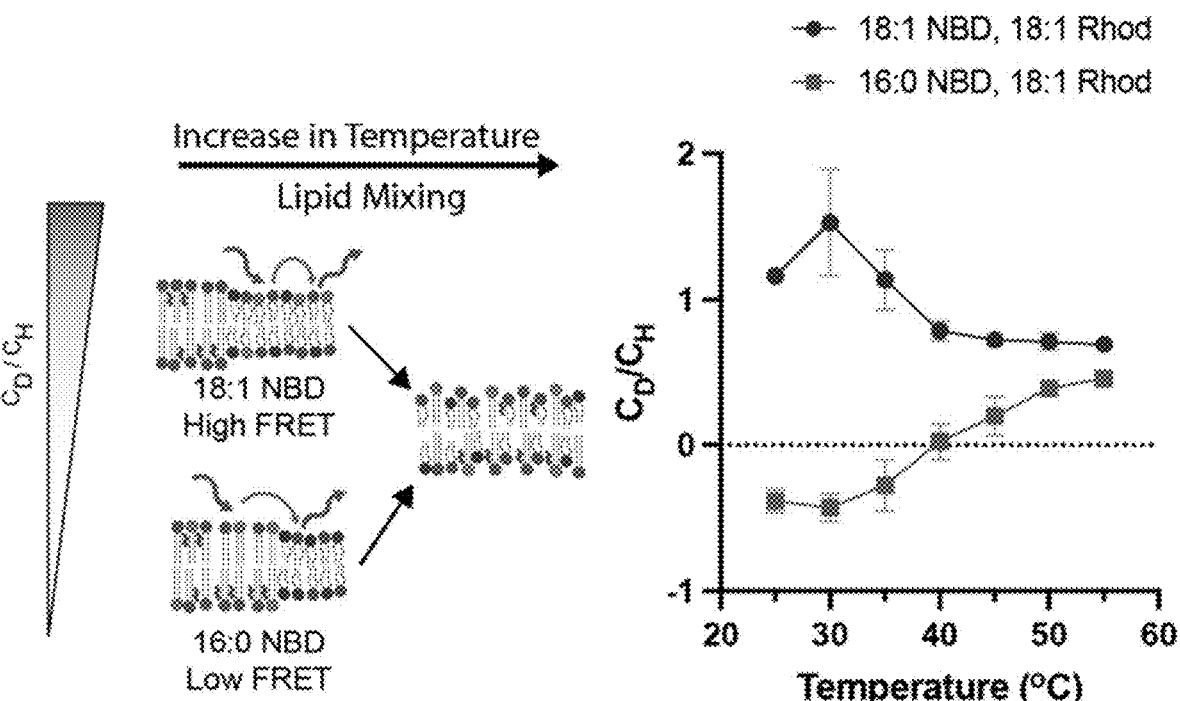
FIG. 14A-14C.
Figure 14B:
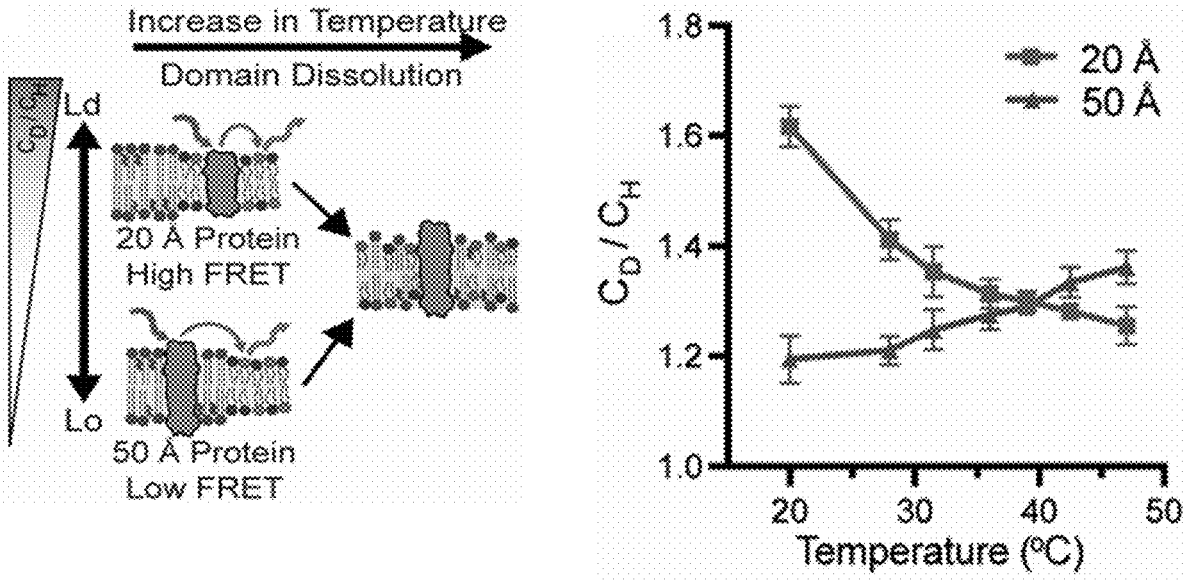
Figure 14C:
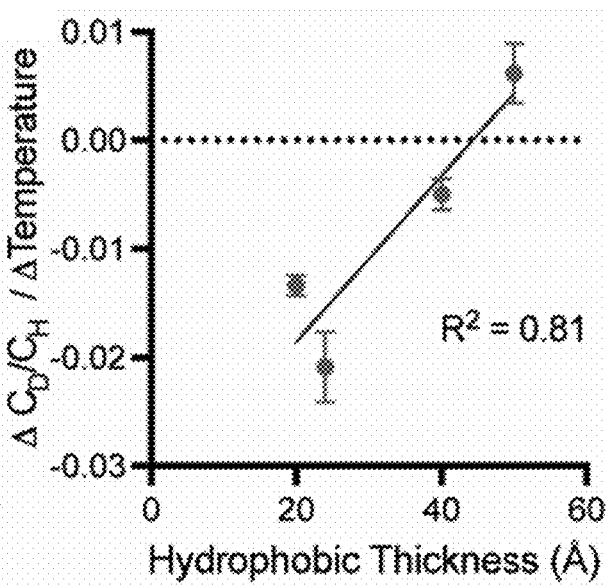

Using this metric, $C_D/C_H$ is higher when proteins and dye partition to the same lipid domain and low when they partition to separate domains (FIG. 14) (24). As shown in FIG. 14A, differences in $C_D/C_H$ were measured when incorporating either 18:1 or 16:0 conjugated NBD (ex. 460 nm/em. 535 nm) in vesicles composed of 42.5 mol % 14:1 PC/27.5 mol % DPPC/30 mol % Cholesterol and 18:1 PC Rhodamine (ex. 560 nm/em. 590 nm). Lipid-lipid FRET was used to validate $C_D/C_H$. 18:1 PC NBD resided in the liquid disordered lipid phase, with 18:1 Rhodamine, and this had a higher $C_D/C_H$ compared to vesicles with 16:0 NBD, which resided in the liquid ordered phase, farther from 18:1 Rhodamine (lower $C_D/C_H$). Upon increasing temperature, $C_D/C_H$ converged, indicating that lipids intermix at higher temperatures due to increases in fluidity and subsequent lipid miscibility. Similarly, as shown in FIG. 14B, $C_D/C_H$ values of the 20 and 50 Å protein were measured over a range of temperatures. At room temperature, the 20 Å protein had a higher $C_D/C_H$, indicating that it resides in the dye containing, thinner and more unsaturated 14:1 PC rich phase. Upon increasing temperature to dissolve domains, the average distance between the unsaturated lipid dye and thinner protein increased. Conversely, the 50 Å protein had lower $C_D/C_H$ values at lower temperatures that increased with increasing temperature. This increase in $C_D/C_H$ values suggests the larger 50 Å protein shifted from an original position in the dye poor, thicker and more saturated DPPC rich lipid phase to one more well mixed with the lipid dye. As temperature increases, the membrane becomes more fluid enabling lipid mixing and convergence of the two $C_D/C_H$ curves (FIG. 14B). This FRET data obtained as a function of temperature mirrors the simulation data in FIG. 13 quite well. Further, $C_D/C_H$ and its change over temperature for the 20, 24, 40, and 50 Å hairpin proteins correlated with hydrophobic thickness, as shown in FIG. 14C and FIG. 15. FIG. 15A shows spectra of SNAP conjugated protein in a homogenous DOPC membrane containing 0.1 mol % 18:1 Rhodamine before and after the addition of trypsin and triton. The dequenching of AF488 after the addition of triton and trypsin indicates that lipid-protein FRET is occurring. As shown in FIG. 15B, at room temperature, $C_D/C_H$ values were higher for membrane proteins with shorter transmembrane domains, indicating that the shorter the transmembrane domain, the closer the protein is to rhodamine on average. As shown in FIG. 15C, upon increasing temperature, $C_D/C_H$ for all constructs converged to the same value, indicating that lipid and proteins mixing can occur at elevated temperatures. The simulations and FRET data demonstrate lipid composition around a protein can be tuned by hydrophobic mismatch. This suggests that hydrophobic mismatch coupled with lipid domain formation can be leveraged to organize proteins into distinct regions within synthetic membranes. All experiments were performed 3 times, error bars represent the S. E. M.

Next, the ability to modulate protein-protein interactions by localizing proteins to separate lipid domains was explored. Controlling the interactions between membrane proteins within a membrane would offer substantial advantages in the design of membrane-based technologies such as those that utilize transmembrane signaling transduction modules (9, 10). MD simulations were performed for the 20 Å and 50 Å hairpin protein in a homogenous, single component and heterogenous, ternary membranes (FIG. 16A). In homogenous DOPC membranes, 20 Å and 50 Å proteins can be close to one another, however in phase separating lipid mixtures proteins remain farther from one another as predicted by MD simulations. As shown in FIG. 16B, at room temperature, protein-protein distance between the 20 and 50 Å hairpin was on average smaller in homogenous, single component DOPC membranes compared to membranes composed of 42.5 mol % 14:1 PC/27.5 mol % DPPC/30 mol % Cholesterol (Domains). At 47° C., protein-protein distance decreases in membranes composed of 42.5 mol % 14:1 PC/27.5 mol % DPPC/30 mol % Cholesterol due to increased lipid mixing. These simulations demonstrated that proteins were able to be close to one another in homogenous membranes but remained separated in the mixed, phase segregated membrane. Histograms were generated from 3 independent simulations.

Figure 17A:
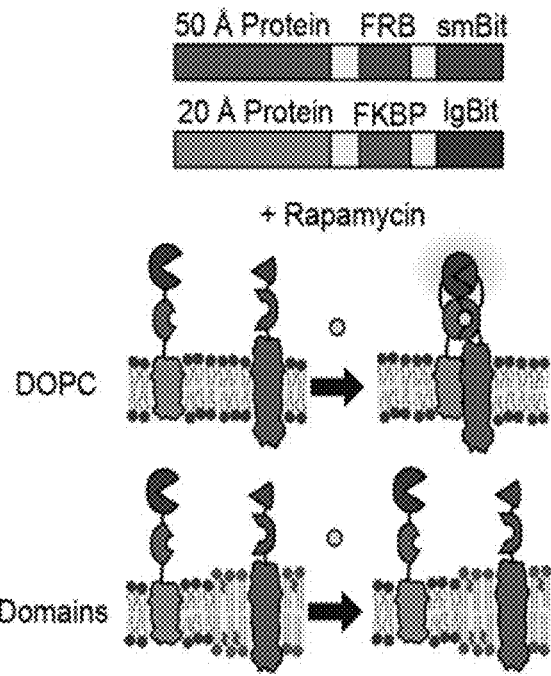
Figure 17B:
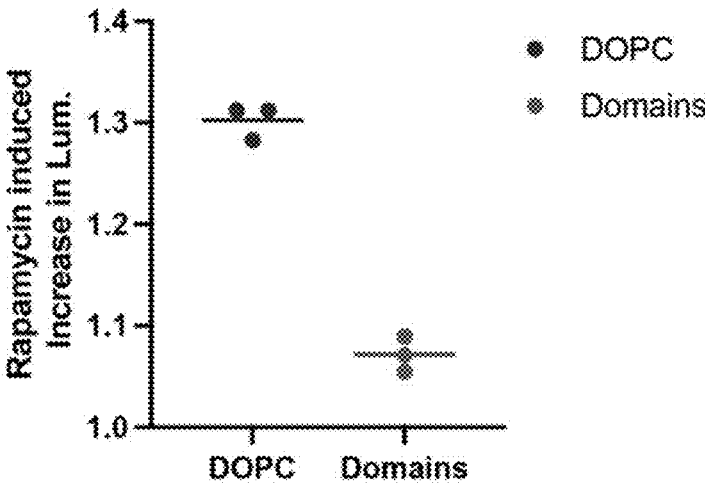

To determine if this behavior could be recapitulated, rapamycin inducible-dimerizing domains and NanoBit, a split nano luciferase (33), were fused to the C terminus of the 20 and 50 Å proteins. To assess how lipid domains affected protein compartmentalization and subsequent NanoBit assembly, smBit and lgBit fused to the 20 Å and 50 Å protein, respectively, were co-expressed with homogenous or phase separated membranes. Illustrated in FIG. 17A, FRB (lgBit) and FKBP (smBit) were fused to the C-terminus of the 20 and 50 Å protein, respectively. The luminescence changed following the addition of rapamycin (9), which chemically induces protein dimerization, and subsequent luciferase. As shown in FIG. 17B, upon addition of rapamycin, luminescence increased when proteins were in homogenous membranes (DOPC); however, the increase was minimal in phase separated membranes (Domains), suggesting that proteins were unable to dimerize due to segregation into different lipid domains.

A temperature ramp was performed on these systems to dissolve lipid domains (FIG. 17C). In phase separated systems, luminescence increased with temperature when lgBit and smBit were fused to the hetero-pair of 20 and 50 Å protein, respectively, relative to when smBit and lgBit were both conjugated to homo-pairs of either the 20 or 50 Å proteins. Importantly, only a slight increase in luminescence was observed with increase in temperature when proteins were in homogenous membranes, indicating the proteins were more evenly distributed in the homogenous membrane (FIG. 17D, raw data in left panel).

Figure 18A:
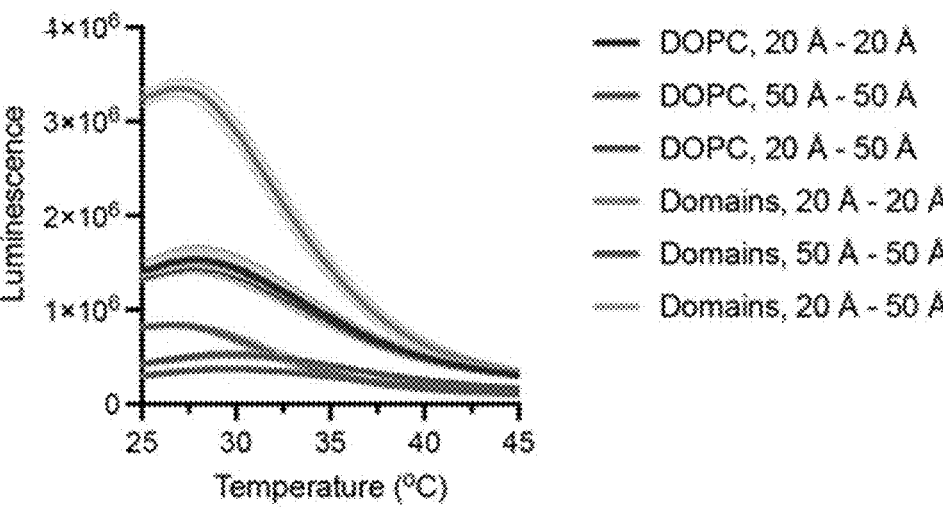
FIGS. 18A-18C illustrate analysis of split luciferase reconstitution in response to domain dissolution via heating.
Figure 18B:
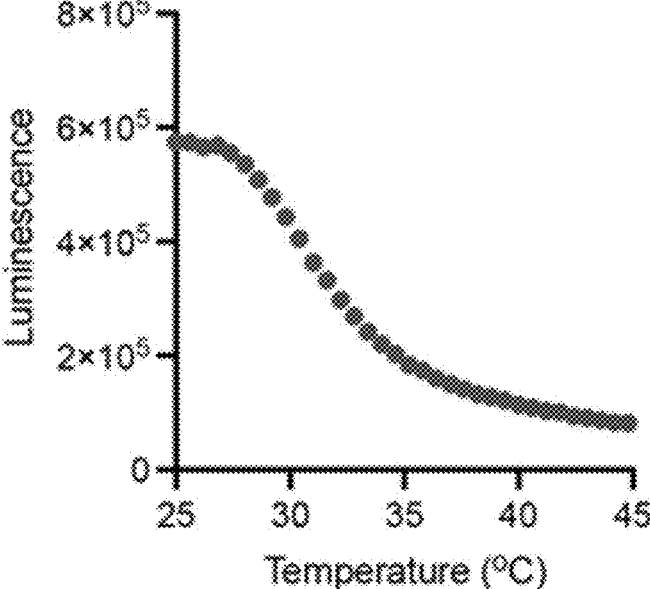
Figure 18C:
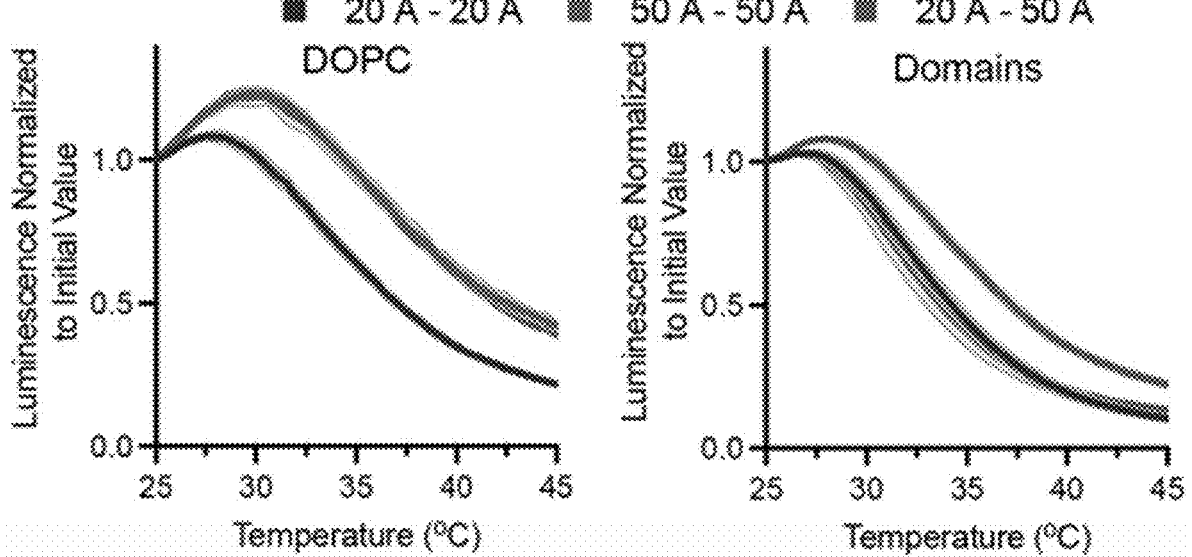

Further analysis is shown in FIG. 18. FIG. 18A shows raw luminescence data of split luciferase constructs in DOPC and domain forming membranes. Luminescence values differed due to differences in expression. Values decreased with increasing temperature, as luciferase is less efficient at elevated temperatures as demonstrated by a luminescence vs temperature for soluble NanoBit (FIG. 18B). By normalizing by the initial value, changes in luminescence for each combination of proteins changes in DOPC (FIG. 18C, left panel) and domain forming membranes (FIG. 18C, right panel) were compared. For domain forming mixtures, transmembrane homodimers decreased more quickly than the heterodimer case. This suggests that homodimers become more dilute as a result of lipid demixing and heterodimers are able to interact more and thus reconstitute luciferase. An increase in luminescence was also observed in domain forming mixtures when luminescence values were normalized by soluble luciferase luminescence at each temperature. Combined, the simulation and experimental data suggest lipid-lipid and lipid-protein interactions can together be harnessed to modulate protein interactions in a single membrane. Such methods may be used to control multienzyme or split enzyme activity or alter the spatial presentation of binding proteins to interact with cells and initiate cellular signaling cascades.

REFERENCES

1. P. Lujan, F. Campelo, Should I stay or should I go?Golgi membrane spatial organization for protein sorting and retention. Archives of Biochemistry and Biophysics. 707, 108921 (2021).
2. Y. Guo, D. W. Sirkis, R. Schekman, Protein Sorting at the trans-Golgi Network. http://dx.doi.org/10.1146/annurev-cellbio-100913-013012. 30, 169-206 (2014).
3. S. Rodriguez-Gallardo, K. Kurokawa, S. Sabido-Bozo, A. Cortes-Gomez, A. Ikeda, V. Zoni, A. Aguilera-Romero, A. M. Perez-Linero, S. Lopez, M. Waga, M. Araki, M. Nakano, H. Riezman, K. Funato, S. Vanni, A. Nakano, M. Muniz, Ceramide chain length-dependent protein sorting into selective endoplasmic reticulum exit sites. Science Advances. 6, 8237-8248 (2020).
4. R. Prasad, A. Sliwa-gonzalez, Y. Barral, Mapping bilayer thickness in the ER membrane (2020).
5. H. J. Sharpe, T. J. Stevens, S. Munro, A Comprehensive Comparison of Transmembrane Domains Reveals Organelle-Specific Properties. Cell. 142, 158 (2010).
6. J. H. Lorent, K. R. Levental, L. Ganesan, G. Rivera-Longsworth, E. Sezgin, M. Doktorova, E. Lyman, I. Levental, Plasma membranes are asymmetric in lipid unsaturation, packing and protein shape. Nature Chemical Biology 2020 16:6. 16, 644-652 (2020).
7. J. H. Lorent, B. Diaz-Rohrer, X. Lin, K. Spring, A. A. Gorfe, K. R. Levental, I. Levental, Structural determinants and functional consequences of protein affinity for membrane rafts. Nature Communications. 8, 1-10 (2017).
8. T. Harayama, H. Riezman, Understanding the diversity of membrane lipid composition. Nature Reviews Molecular Cell Biology 2018 19:5. 19, 281-296 (2018).
9. K. A. Schwarz, N. M. Daringer, T. B. Dolberg, J. N. Leonard, Rewiring human cellular input-output using modular extracellular sensors. Nature Chemical Biology 2016 13:2. 13, 202-209 (2016).
10. C. Y. Wu, K. T. Roybal, E. M. Puchner, J. Onuffer, W. A. Lim, Remote control of therapeutic T cells through a small moleculeâ€"gated chimeric receptor. Science (1979). 350 (2015), doi:10.1126/SCIENCE.AAB4077/SUPPL_FILE/WU.SM.PDF.

11. J. G. Rurik, I. Tombdcz, A. Yadegari, P. O. Mendez Ferndndez, S. v. Shewale, L. Li, T. Kimura, O. Y. Soliman, T. E. Papp, Y. K. Tam, B. L. Mui, S. M. Albelda, E. Pure, C. H. June, H. Aghajanian, D. Weissman, H. Parhiz, J. A. Epstein, CAR T cells produced in vivo to treat cardiac injury. Science (1979). 375, 91-96 (2022).

12. Y. Lin, J. Wu, W. Gu, Y. Huang, Z. Tong, L. Huang, J. Tan, Y. Lin, J. Wu, W. Gu, J. Tan, Y. Huang, Z. Tong, L. Huang, Exosome-Liposome Hybrid Nanoparticles Deliver CRISPR/Cas9 System in MSCs. Advanced Science. 5, 1700611 (2018).

13. T. Q. Vu, J. A. Peruzzi, L. E. Sant'Anna, E. W. Roth, N. P. Kamat, Nano Letters, in press, doi:10.1021/ACS.NANOLETT.1C04365.

14. Z. jie Yang, Z. yan Yu, Y. ming Cai, R. rong Du, L. Cai, Engineering of an enhanced synthetic Notch receptor by reducing ligand-independent activation. Communications Biology 2020 3:1. 3, 1-7 (2020).

15. P. Lu, D. Min, F. DiMaio, K. Y. Wei, M. D. Vahey, S. E. Boyken, Z. Chen, J. A. Fallas, G. Ueda, W. Sheffler, V. K. Mulligan, W. Xu, J. U. Bowie, D. Baker, Accurate computational design of multipass transmembrane proteins. Science (1979). 359, 1042-1046 (2018).

16. C. Xu, P. Lu, T. M. Gamal El-Din, X. Y. Pei, M. C. Johnson, A. Uyeda, M. J. Bick, Q. Xu, D. Jiang, H. Bai, G. Reggiano, Y. Hsia, T. J. Brunette, J. Dou, D. Ma, E. M. Lynch, S. E. Boyken, P. S. Huang, L. Stewart, F. DiMaio, J. M. Kollman, B. F. Luisi, T. Matsuura, W. A. Catterall, D. Baker, Computational design of transmembrane pores. Nature 2020 585:7823. 585, 129-134 (2020).

17. F. A. Heberle, M. Doktorova, H. L. Scott, A. D. Skinkle, M. N. Waxham, I. Levental, Direct label-free imaging of nanodomains in biomimetic and biological membranes by cryogenic electron microscopy. Proc Natl Acad Sci USA. 117, 19943-19952 (2020).

18. M. L. Jacobs, M. A. Boyd, N. P. Kamat, Diblock copolymers enhance folding of a mechanosensitive membrane protein during cell-free expression. Proc Natl Acad Sci USA. 116, 4031-4036 (2019).

19. G. S. Waldo, B. M. Standish, J. Berendzen, T. C. Terwilliger, Rapid protein-folding assay using green fluorescent protein. Nature Biotechnology 1999 17:7. 17, 691-695 (1999).

20. A. D. Silverman, N. Kelley-Loughnane, J. B. Lucks, M. C. Jewett, Deconstructing Cell-Free Extract Preparation for in Vitro Activation of Transcriptional Genetic Circuitry. ACS Synthetic Biology. 8, 403-414 (2019).

21. C. E. Hilburger, M. L. Jacobs, K. R. Lewis, J. A. Peruzzi, N. P. Kamat, Controlling Secretion in Artificial Cells with a Membrane and Gate. ACS Synthetic Biology. 8 (2019), doi:10.1021/acssynbio.8b00435.

22. E. Sezgin, I. Levental, S. Mayor, C. Eggeling, The mystery of membrane organization: composition, regulation and roles of lipid rafts. Nature Reviews Molecular Cell Biology. 18, 361-374 (2017).

23. H. J. Kaiser, A. Orlowski, T. Róg, T. K. M. Nyholm, W. Chai, T. Feizi, D. Lingwood, I. Vattulainen, K. Simons, Lateral sorting in model membranes by cholesterol-mediated hydrophobic matching. Proc Natl Acad Sci USA (2011), doi:10.1073/pnas.1103742108.

24. Q. Lin, E. London, Altering hydrophobic sequence lengths shows that hydrophobic mismatch controls affinity for ordered lipid domains (rafts) in the multitransmembrane strand protein perfringolysin O. Journal of Biological Chemistry. 288, 1340-1352 (2013).

25. J. P. Schlebach, P. J. Barrett, C. A. Day, J. H. Kim, A. K. Kenworthy, C. R. Sanders, Topologically Diverse Human Membrane Proteins Partition to Liquid-Disordered Domains in Phase-Separated Lipid Vesicles. Biochemistry. 55, 985-988 (2016).

26. L. v. Schafer, D. H. de Jong, A. Holt, A. J. Rzepiela, A. H. de Vries, B. Poolman, J. A. Killian, S. J. Marrink, Lipid packing drives the segregation of transmembrane helices into disordered lipid domains in model membranes. Proc Natl Acad Sci USA. 108, 1343-1348 (2011).

27. D. Lingwood, J. Ries, P. Schwille, K. Simons, Plasma membranes are poised for activation of raft phase coalescence at physiological temperature. Proceedings of the National Academy of Sciences. 105, 10005-10010 (2008).

28. B. Sorre, A. Callan-Jones, J. B. Manneville, P. Nassoy, J. F. Joanny, J. Prost, B. Goud, P. Bassereau, Curvature-driven lipid sorting needs proximity to a demixing point and is aided by proteins. Proceedings of the National Academy of Sciences. 106, 5622-5626 (2009).

29. S. Katira, K. K. Mandadapu, S. Vaikuntanathan, B. Smit, D. Chandler, Pre-transition effects mediate forces of assembly between transmembrane proteins. Elife. 5 (2016), doi:10.7554/eLife.13150.

30. J. Steinkühler, P. Fonda, T. Bhatia, Z. Zhao, F. S. C. Leomil, R. Lipowsky, R. Dimova, Superelasticity of Plasma- and Synthetic Membranes Resulting from Coupling of Membrane Asymmetry, Curvature, and Lipid Sorting. Advanced Science. 8, 2102109 (2021).

31. S. L. Veatch, S. L. Keller, Separation of Liquid Phases in Giant Vesicles of Ternary Mixtures of Phospholipids and Cholesterol. Biophysical Journal. 85, 3074 (2003).

32. J. T. Marinko, J. T. Marinko, A. K. Kenworthy, A. K. Kenworthy, C. R. Sanders, C. R. Sanders, Peripheral myelin protein 22 preferentially partitions into ordered phase membrane domains. Proc Natl Acad Sci USA. 117, 14168-14177 (2020).

33. A. S. Dixon, M. K. Schwinn, M. P. Hall, K. Zimmerman, P. Otto, T. H. Lubben, B. L. Butler, B. F. Binkowski, T. MacHleidt, T. A. Kirkland, M. G. Wood, C. T. Eggers, L. P. Encell, K. v. Wood, NanoLuc Complementation Reporter Optimized for Accurate Measurement of Protein Interactions in Cells. ACS Chemical Biology. 11, 400-408 (2016).

The invention claimed is:

1. A method comprising:

incubating together a) a plasmid encoding a first protein, the first protein having a first hydrophobic thickness;

b) a cell-free protein synthesis system; and c) a lipid structure comprising a lipid bilayer, the lipid bilayer comprising a first domain having a second hydrophobic thickness;

wherein the incubation is done under conditions that promote integration of the first protein into the first domain of the lipid bilayer, wherein the first protein traverses the lipid bilayer, wherein the first hydrophobic thickness and the second hydrophobic thickness have a difference of no greater than about 5 angstroms.

2. The method of claim 1, wherein the lipid structure is a synthetic vesicle.

3. The method of claim 2, wherein prior to incubating the synthetic vesicle the method further comprises preparing the vesicle with cholesterol and one or more phosphatidylcholines.

4. The method of claim 1, wherein the lipid structure is a lipid nanoparticle, a cell, or an organelle.

5. The method of claim 1, wherein the first hydrophobic thickness is between about 20 and about 40 angstroms.

6. The method of claim 1, further comprising incubating the lipid structure with a molecule after the first protein integrates into the lipid bilayer.

7. The method of claim 6, wherein the molecule is selected from an analyte and a drug.

8. The method of claim 1 wherein the lipid bilayer comprises a second domain having a third hydrophobic thickness, wherein the method further comprises providing a second protein having a fourth hydrophobic thickness, wherein the second hydrophobic difference and the third hydrophobic thickness have a difference of greater than about 5 angstroms, and wherein the third hydrophobic thickness and the fourth hydrophobic thickness have a difference of no greater than about 5 angstroms.

9. The method of claim 1, wherein a) comprises one or more additional plasmids encoding additional proteins that traverse the lipid bilayer; and wherein each of the first protein and the one or more additional proteins has a protein hydrophobic thickness, and wherein each protein hydrophobic thickness has a difference of greater than about 5 angstroms;

wherein the lipid bilayer comprises one or more additional domains;

wherein each of the first domain and the one or more additional domains has a different hydrophobic thickness, and wherein each domain hydrophobic thickness has a difference of greater than about 5 angstroms; and wherein each protein thickness is no greater than 5 angstroms different than the hydrophobic thickness of one of the domains.

10. The method of claim 9, wherein the incubation is done at a temperature of between about 20 and about 37° C.

11. The method of claim 10, further comprising increasing the temperature to between about 37 and about 80° C. after the proteins are integrated into the lipid bilayer.

12. The method of claim 9, wherein the lipid structure is a synthetic vesicle comprising cholesterol and one or more phosphatidylcholines.

13. The method of claim 12, wherein the synthetic vesicle comprises at least 20 mol % cholesterol and less than 30 mol % cholesterol.

14. The method of claim 12, wherein the synthetic vesicle comprises 20 mol % cholesterol.

* * * * *

SEQUENCE LISTING

```
Sequence total quantity: 30
SEQ ID NO: 1          moltype = AA  length = 104
FEATURE               Location/Qualifiers
source                1..104
                      mol_type = protein
                      organism = synthetic construct
SEQUENCE: 1
MTRKEIIEKL EKSLRRQKEL AERLLILLLL LLRLLHELLE LLRRLEELQR RGSSDEEVHE   60
LLRRIIELVE RIIYLVIFII ALVREIIKLA EHQRRLVEEL KKQD                     104
```

```
SEQ ID NO: 2               moltype = AA   length = 104
FEATURE                    Location/Qualifiers
source                     1..104
                           mol_type = protein
                           organism = synthetic construct
SEQUENCE: 2
MTRKEIIEKL EKSLRRQKKL ARFLLILLLL LLALLLELLE LLRRLEELQR RGSSDEEVHE   60
LLRRIIELVE YIILLVLFII VLVRIIIKLA EHQRRLVEEL KKQD                    104

SEQ ID NO: 3               moltype = AA   length = 104
FEATURE                    Location/Qualifiers
source                     1..104
                           mol_type = protein
                           organism = synthetic construct
SEQUENCE: 3
MTRTEIIREL ERSLREQRVL AIFLLALLIV LLWLLQQLKE LLRELERLQR EGSSDEDVRE   60
LLREIKELVE NIVYLVIIIM VLVLVIIALA RTQKYLVEEL KRQD                    104

SEQ ID NO: 4               moltype = AA   length = 104
FEATURE                    Location/Qualifiers
source                     1..104
                           mol_type = protein
                           organism = synthetic construct
SEQUENCE: 4
MTRTEIIREL ERSLRLQLVL AIFLLGLLIV LLWLLQQLKE LLRELERLQR EGSSDEDVRE   60
LLREIKELVE NIVYLVIIIM VLVLVIIALT VTQKYLVEEL KRQD                    104

SEQ ID NO: 5               moltype = AA   length = 104
FEATURE                    Location/Qualifiers
source                     1..104
                           mol_type = protein
                           organism = synthetic construct
SEQUENCE: 5
MTRTEIITRL SFSLLLQLVL AIFLLALLIV LLWLLQQLKE LLRELERLQR EGSSDEDVRE   60
LLREIKELVE NIVYLVIIIM VLVLVIIALA VLQMYLVREL KRQD                    104

SEQ ID NO: 6               moltype = AA   length = 104
FEATURE                    Location/Qualifiers
source                     1..104
                           mol_type = protein
                           organism = synthetic construct
SEQUENCE: 6
MTRTEIITRL SFSLLLQLVL AIFLLALLIV LLVLLIYLKE LLRELERLQR EGSSDEDVRE   60
LLREIKWLVI VIVALVIIIM VLVLVIIALA VLQMYLVREL KRQD                    104

SEQ ID NO: 7               moltype = AA   length = 119
FEATURE                    Location/Qualifiers
source                     1..119
                           mol_type = protein
                           organism = synthetic construct
SEQUENCE: 7
MVLSHHFGKE FASATMTRTE IITRLSFSLL LQLVLAIFLL ALLIVLLVLL IVLMILLIAL   60
EYLQKEGSSD EDVKELLVLI MILVIVIVAL VIIIMVLVLV IIALAVLQMY LVRELKRQD    119

SEQ ID NO: 8               moltype = AA   length = 204
FEATURE                    Location/Qualifiers
source                     1..204
                           mol_type = protein
                           organism = synthetic construct
SEQUENCE: 8
MSAEELLRRS REYLKKVAKF QLVIALVFLI LLEILSRRSE ELIRELEEKG AASEAELARM   60
KQQHMTAYLQ AALTAWEIIS KSLIALLLLQ QNQLNLELNT DTDKNVAEEL LRRSREYLKK   120
VAKKQLVIAF VFLILLEILS RRSEELIREL EEKGAASEAE LARMKQQHMT AYLQAALTAW   180
EIISKSLIAL LLLQQNQLNL ELRH                                          204

SEQ ID NO: 9               moltype = AA   length = 204
FEATURE                    Location/Qualifiers
source                     1..204
                           mol_type = protein
                           organism = synthetic construct
SEQUENCE: 9
MSAEELLRRS REYLKKVAKI QLVIALVFLI LLIILSRRSE ELIRELEEKG AASEAELARM   60
KQQHMTAYLQ AALTAWEIIS KSVIALLLLQ QNQLNLELNT DTDKNVAEEL LRRSREYLKK   120
VAKIQLVIAF VFLILLIILS RRSEELIREL EEKGAASEAE LARMKQQHMT AYLQAALTAW   180
EIISKSRIAL LLLQQNQLNL ELRH                                          204

SEQ ID NO: 10              moltype = AA   length = 204
FEATURE                    Location/Qualifiers
source                     1..204
```

```
                              mol_type = protein
                              organism = synthetic construct
SEQUENCE: 10
MSAEELLRRS RKYLILVALI QLVIAFVFLI LLILLSWLSW LLIRELEEKG AASEAELARM   60
KIQMMTAYLQ AALTAWEIIV KAVIALLLLR QNQLNLELNT DTDKNVAEEL LRRSRKYLII  120
VALIQLVIAF VFLILLILLS WKSWELIREL EEKGAASEAE LARMKMQVML AYLQAALTAW  180
EIIAKSVIAL LLLLQNQLNL ELRH                                          204

SEQ ID NO: 11              moltype = AA  length = 204
FEATURE                    Location/Qualifiers
source                     1..204
                              mol_type = protein
                              organism = synthetic construct
SEQUENCE: 11
MSAEELLRWS RIYLVIVALI QLVIAFVFLI LLILLSWLSL VLIWELEEKG AASEAELARM   60
ILQVMTAYLQ AALTAWEIIA KVVIALLLLV VNQLNLELNT DTDKNVAEEL LRRSLLYLIM  120
VALIQLVIAF VFLILLILLS WISLLLIWEL EEKGAASEAE LARMAIQLMI AYLQAALTAW  180
EIIAKSVIAL LLLILNQLNL ELRH                                          204

SEQ ID NO: 12              moltype = DNA  length = 1053
FEATURE                    Location/Qualifiers
source                     1..1053
                              mol_type = other DNA
                              organism = synthetic construct
SEQUENCE: 12
atgggctcga cccgcaagga gatcattgaa aagttggaga aatcccttcg tcgtcaaaaa   60
gagttggcgg aacgcctttt gattcttctg ttgttgttat tgcgtttatt acatgagttg  120
cttgagcttt tgcgccgtct ggaagaattg cagcgtcgcg ggtcgtcaga tgaggaggtg  180
catgaacttc tgcgtcgcat tattgaattg gtcgagcgca tcatttatct tgtcatcttt  240
atcattgctc tggtacgcga aattatcaaa cttgcagagc accagcgtcg tttggtagaa  300
gagcttaaaa agcaggacgg tagcagcgga tccatggtga gcaagggcga ggagctgttc  360
accgggtgg tgcccatcct ggtcgagctg gacggcgacg taaacggcca caagttcagc  420
gtgtccggcg agggcgaggg cgatgccacc tacggcaagc tgaccctgaa gttcatctgc  480
accaccggca agctgcccgt gccctggccc accctcgtga ccaccctgac ctacggcgtg  540
cagtgcttca gccgctaccc cgaccacatg aagcagcacg acttcttcaa gtccgccatg  600
cccgaaggct acgtccagga gcgcaccatc ttcttcaagg acgacggcaa ctacaagacc  660
cgcgccgagg tgaagttcga gggcgacacc ctggtgaacc gcatcgagct gaagggcatc  720
gacttcaagg aggacggcaa catcctgggg cacaagctgg agtacaacta caacagccac  780
aacgtctata tcatggccga caagcagaag aacggcatca aggtgaactt caagatccgc  840
cacaacatcg aggacggcag cgtgcagctc gccgaccact accagcagaa cacccccatc  900
ggcgacggcc ccgtgctgct gcccgacaac cactacctga gcacccagtc caagctgagc  960
aaagacccca acgagaagcg cgatcacatg gtcctgctgg agttcgtgac cgccgccggg 1020
atcactctcg gcatggacga gctgtacaag taa                              1053

SEQ ID NO: 13              moltype = DNA  length = 1053
FEATURE                    Location/Qualifiers
source                     1..1053
                              mol_type = other DNA
                              organism = synthetic construct
SEQUENCE: 13
atgggctcga ctcgcaagga aatcattgag aagttagaaa agagcctgcg tcgccagaag   60
aaactggcac gtttcctttt aatcttactt ttactgttgt tagctctgct gcttgaatta  120
ttggagcttt tgcgccgtct ggaagagttg cagcgtcgcg gctcaagtga cgaagaagtc  180
catgaattat tacgccgtat cattgagctt gtggaatata ttatccttct ggtgttgttc  240
atcatcgtac ttgtccgcat catcatcaaa ttagcagagc atcaacgtcg cttggttgag  300
gaactgaaga agcaggacgg tagcagcgga tccatggtga gcaagggcga ggagctgttc  360
accgggtgg tgcccatcct ggtcgagctg gacggcgacg taaacggcca caagttcagc  420
gtgtccggcg agggcgaggg cgatgccacc tacggcaagc tgaccctgaa gttcatctgc  480
accaccggca agctgcccgt gccctggccc accctcgtga ccaccctgac ctacggcgtg  540
cagtgcttca gccgctaccc cgaccacatg aagcagcacg acttcttcaa gtccgccatg  600
cccgaaggct acgtccagga gcgcaccatc ttcttcaagg acgacggcaa ctacaagacc  660
cgcgccgagg tgaagttcga gggcgacacc ctggtgaacc gcatcgagct gaagggcatc  720
gacttcaagg aggacggcaa catcctgggg cacaagctgg agtacaacta caacagccac  780
aacgtctata tcatggccga caagcagaag aacggcatca aggtgaactt caagatccgc  840
cacaacatcg aggacggcag cgtgcagctc gccgaccact accagcagaa cacccccatc  900
ggcgacggcc ccgtgctgct gcccgacaac cactacctga gcacccagtc caagctgagc  960
aaagacccca acgagaagcg cgatcacatg gtcctgctgg agttcgtgac cgccgccggg 1020
atcactctcg gcatggacga gctgtacaag taa                              1053

SEQ ID NO: 14              moltype = DNA  length = 1053
FEATURE                    Location/Qualifiers
source                     1..1053
                              mol_type = other DNA
                              organism = synthetic construct
SEQUENCE: 14
atgatgggca ccaggacaga gatcatcagg gagcttgagc gatccttgcg agagcagcgc   60
gtgcttgcta ttttcctcct ggcgttgctc atcgtacttc tctggctgct gcaacaactt  120
aaagaattgt tgcgcgagct ggaacggctg caaagagaag gttcatccga cgaggatgta  180
agagaattgc ttagagaaat caaagaactt gttgagaaca ttgtatatct ggtaataata  240
```

```
atcatggtcc tcgtcctggt aatcatagcc ctggcaagaa cgcaaaaata ccttgtcgaa   300
gagctgaagc ggcaggatgg tagcagcgga tccatggtga gcaagggcga ggagctgttc   360
accggggtgg tgcccatcct ggtcgagctg gacggcgacg taaacggcca caagttcagc   420
gtgtccggcg agggcgaggg cgatgccacc tacggcaagc tgaccctgaa gttcatctgc   480
accaccggca agctgcccgt gccctggccc accctcgtga ccaccctgac ctacggcgtg   540
cagtgcttca gccgctaccc cgaccacatg aagcagcacg acttcttcaa gtccgccatg   600
cccgaaggct acgtccagga gcgcaccatc ttcttcaagg acgacggcaa ctacaagacc   660
cgcgccgagg tgaagttcga gggcgacacc ctggtgaacc gcatcgagct gaagggcatc   720
gacttcaagg aggacggcaa catcctgggg cacaagctgg agtacaacta caacagccac   780
aacgtctata tcatggccga caagcagaag aacggcatca aggtgaactt caagatccgc   840
cacaacatcg aggacggcag cgtgcagctc gccgaccact accagcagaa cacccccatc   900
ggcgacggcc ccgtgctgct gcccgacaac cactacctga gcacccagtc caagctgagc   960
aaagacccca acgagaagcg cgatcacatg gtcctgctgg agttcgtgac cgccgccggg  1020
atcactctcg gcatggacga gctgtacaag taa                                1053
```

```
SEQ ID NO: 15               moltype = DNA   length = 1044
FEATURE                     Location/Qualifiers
source                      1..1044
                            mol_type = other DNA
                            organism = synthetic construct
SEQUENCE: 15
atgacccgaa cggaaatcat tagggagctg gagcgaagtt tgcgcctcca gctggtcctt   60
gcgatatttc tgctcggact tttgatcgta cttctgtggc tgttgcagca gctgaaagaa  120
ctgttgcggg agcttgaaag gctccaacgg gagggtagca gcgatgagga cgttcgggag  180
ctgcttaggg agattaagga gcttgtggag aacattgttt atttggtcat tattatcatg  240
gtgttggttc tcgtaataat agcactcact gtaactcaaa agtatctggt ggaggaactt  300
aaacggcagg atggcggcgg atccatggtg agcaagggcg aggagctgtt caccggggtg  360
gtgcccatcc tggtcgagct ggacggcgac gtaaacggcc acaagttcag cgtgtccggc  420
gagggcgagg gcgatgccac ctacggcaag ctgaccctga gttcatctg caccaccggc  480
aagctgcccg tgccctggcc caccctcgtg accaccctga cctacggcgt gcagtgcttc  540
agccgctacc cgaccacat gaagcagcac gacttcttca gtccgccat gcccgaaggc  600
tacgtccagg agcgcaccat cttcttcaag gacgacggca actacaagac ccgcgccgag  660
gtgaagttcg agggcgacac cctggtgaac cgcatcgagc tgaagggcat cgacttcaag  720
gaggacggca acatcctggg gcacaagctg gagtacaact acaacagcca caacgtctat  780
atcatggccg acaagcagaa gaacggcatc aaggtgaact tcaagatccg ccacaacatc  840
gaggacggca gcgtgcagct cgccgaccac taccagcaga acacccccat cggcgacggc  900
cccgtgctgc tgcccgacaa ccactacctg agcacccagt ccaagctgag caaagacccc  960
aacgagaagc gcgatcacat ggtcctgctg gagttcgtga ccgccgccgg gatcactctc  1020
ggcatggacg agctgtacaa gtaa                                          1044
```

```
SEQ ID NO: 16               moltype = DNA   length = 1053
FEATURE                     Location/Qualifiers
source                      1..1053
                            mol_type = other DNA
                            organism = synthetic construct
SEQUENCE: 16
atgggctcga cccgtaccga aatcattacc cgtctgagct tcagcctgct gctgcagctg   60
gttctggcga tttttctgct ggcgctgctg atcgtgctgc tgtggctgct gcagcaactg  120
aaggaactgc tgcgtgagct ggaacgtctg caacgtgagg gtagcagcga cgaagatgtt  180
cgtgagctgc tgcgtgagat taaagaactg gtggagaaca tcgtttacct ggtgatcatt  240
atcatggtgc tggttctggt gattatcgcg ctggcggttc tgcagatgta tctggtgcgt  300
gaactgaagc gtcaagacgg tagcagcgga tccatggtga gcaagggcga ggagctgttc  360
accggggtgg tgcccatcct ggtcgagctg gacggcgacg taaacggcca caagttcagc  420
gtgtccggcg agggcgaggg cgatgccacc tacggcaagc tgaccctgaa gttcatctgc  480
accaccggca agctgcccgt gccctggccc accctcgtga ccaccctgac ctacggcgtg  540
cagtgcttca gccgctaccc cgaccacatg aagcagcacg acttcttcaa gtccgccatg  600
cccgaaggct acgtccagga gcgcaccatc ttcttcaagg acgacggcaa ctacaagacc  660
cgcgccgagg tgaagttcga gggcgacacc ctggtgaacc gcatcgagct gaagggcatc  720
gacttcaagg aggacggcaa catcctgggg cacaagctgg agtacaacta caacagccac  780
aacgtctata tcatggccga caagcagaag aacggcatca aggtgaactt caagatccgc  840
cacaacatcg aggacggcag cgtgcagctc gccgaccact accagcagaa cacccccatc  900
ggcgacggcc ccgtgctgct gcccgacaac cactacctga gcacccagtc caagctgagc  960
aaagacccca acgagaagcg cgatcacatg gtcctgctgg agttcgtgac cgccgccggg  1020
atcactctcg gcatggacga gctgtacaag taa                                1053
```

```
SEQ ID NO: 17               moltype = DNA   length = 1044
FEATURE                     Location/Qualifiers
source                      1..1044
                            mol_type = other DNA
                            organism = synthetic construct
SEQUENCE: 17
atgactagga cggagattat aactaggctc tcttttttctc ttttgttgca gctcgtgctc   60
gctatatttc tccttgctct tctgatagtc cttcttgttc tgcttatcta tttgaaggaa  120
cttctccgcg agttggagcg actccagagg gaggggtcaa gcgacgaaga tgtacgagaa  180
ttgttgcgcg aaattaaatg gttggtaatt gtgattgtgg ctctcgtaat cattataatg  240
gtcttggtat tggtaatcat cgctcttgct gtgttgcaaa tgtacctcgt tcgcgaactg  300
aaacggcagg atggcggcgg atccatggtg agcaagggcg aggagctgtt caccggggtg  360
gtgcccatcc tggtcgagct ggacggcgac gtaaacggcc acaagttcag cgtgtccggc  420
gagggcgagg gcgatgccac ctacggcaag ctgaccctga gttcatctg caccaccggc  480
```

-continued

```
aagctgcccg tgccctggcc caccctcgtg accaccctga cctacgcgcg tgcagtgcttc   540
agccgctacc ccgaccacat gaagcagcac gacttcttca agtccgccat gcccgaaggc   600
tacgtccagg agcgcaccat cttcttcaag gacgacggca actacaagac ccgcgccgag   660
gtgaagttcg agggcgacac cctggtgaac cgcatcgagc tgaagggcat cgacttcaag   720
gaggacggca acatcctggg gcacaagctg gagtacaact acaacagcca caacgtctat   780
atcatggccg acaagcagaa gaacggcatc aaggtgaact tcaagatccg ccacaacatc   840
gaggacggca gcgtgcagct cgccgaccac taccagcaga acacccccat cggcgacggc   900
cccgtgctgc tgcccgacaa ccactacctg agcacccagt ccaagctgag caaagacccc   960
aacgagaagc gcgatcacat ggtcctgctg gagttcgtga ccgccgccgg gatcactctc  1020
ggcatggacg agctgtacaa gtaa                                          1044
```

```
SEQ ID NO: 18            moltype = DNA   length = 1089
FEATURE                  Location/Qualifiers
source                   1..1089
                         mol_type = other DNA
                         organism = synthetic construct
SEQUENCE: 18
atggtgctgt ctcatcattt tggcaaagaa ttcgctagcg ccaccatgac ccgcacggag   60
attatcacca ggctcagttt ttcccttttg ttgcaacttg tcttggcaat ttttttgctc   120
gcactgctga tcgtactctt ggtgcttttg atagttctga tgattctcct tatagcgttg   180
gaatatcttc aaaaagaggg atcttcagat gaggatgtga aagaactcct ggtgctcata   240
atgattttgg tgatagtgat tgttgccctg gtaattataa tcatggtact ggtcctcgtt   300
ataatcgctc tggctgtgtt gcagatgtac ctggttcggg aactcaagcg acaagacggc   360
ggcggatcca tggtgagcaa gggcgaggag ctgttcaccg gggtggtgcc catcctggtc   420
gagctggacg gcgacgtaaa cggccacaag ttcagcgtgt ccggcgaggg cgagggcgat   480
gccacctacg gcaagctgac cctgaagttc atctgcacca ccggcaagct gcccgtgccc   540
tggcccaccc tcgtgaccac cctgacctac ggcgtgcagt gcttcagccg ctaccccgac   600
cacatgaagc agcacgactt cttcaagtcc gccatgcccg aaggctacgt ccaggagcgc   660
accatcttct tcaaggacga cggcaactac aagacccgcg ccgaggtgaa gttcgagggc   720
gacaccctgg tgaaccgcat cgagctgaag ggcatcgact tcaaggagga cggcaacatc   780
ctggggcaca gctggagta caactacaac agccacaacg tctatatcat ggccgacaag   840
cagaagaacg gcatcaaggt gaacttcaag atccgccaca catcgagga cggcagcgtg   900
cagctcgccg accactacca gcagaacacc cccatcggcg acggccccgt gctgctgccc   960
gacaaccact acctgagcac ccagtccaag ctgagcaaag accccaacga gaagcgcgat  1020
cacatggtcc tgctggagtt cgtgaccgcc gccgggatca ctctcggcat ggacgagctg  1080
tacaagtaa                                                          1089
```

```
SEQ ID NO: 19            moltype = DNA   length = 713
FEATURE                  Location/Qualifiers
source                   1..713
                         mol_type = other DNA
                         organism = synthetic construct
SEQUENCE: 19
taatacgact cactataggg agaccacaac ggtttccctc tagaaataat tttgtttaac   60
tttaagaagg agatatacat atgatggtgc tgtctcatca ttttggcaaa gaattcgcta   120
gcgccaccat gacccgcacg gagattatca ccaggctcag tttttttccctt ttgttgcaac   180
ttgtcttggc aatttttttg ctcgcactgc tgatcgtact cttggtgctt ttgatagttc   240
tgatgattct ccttatagcg ttggaatatc ttcaaaaaga gggatcttca gatgaggatg   300
tgaaagaact cctggtgctc ataatgattt tggtgatagt gattgttgcc ctggtaatta   360
taatcatggt actggtcctc gttataatcg ctctggctgt gttgcagatg tacctggttc   420
gggaactcaa gcgacaagac ggcggcggat ccgactataa agacgatgac gataaataag   480
tcgacgggat cccgactggc gagagccagg taacgaatgg atcgggtcgg catggcatct   540
ccacctcctc gcggtccgac ctgggcatcc gaaggaggac gtcgtccact cggatggcta   600
agggagcggc tgctaacaaa gcccgaaagg aagctgagtt ggctgctgcc accgctgagc   660
aataactagc ataacccctt ggggcctcta aacgggtctt gaggggtttt ttg          713
```

```
SEQ ID NO: 20            moltype = DNA   length = 1119
FEATURE                  Location/Qualifiers
source                   1..1119
                         mol_type = other DNA
                         organism = synthetic construct
SEQUENCE: 20
atggattaca aggatgacga cgataagcat atggtgctgt ctcatcattt tggcaaagaa   60
ttcgctagcg ccaccatgac ccgcacggag attatcacca ggctcagttt ttcccttttg   120
ttgcaacttg tcttggcaat ttttttgctc gcactgctga tcgtactctt ggtgcttttg   180
atagttctga tgattctcct tatagcgttg gaatatcttc aaaaagaggg atcttcagat   240
gaggatgtga aagaactcct ggtgctcata atgattttgg tgatagtgat tgttgccctg   300
gtaattataa tcatggtact ggtcctcgtt ataatcgctc tggctgtgtt gcagatgtac   360
ctggttcggg aactcaagcg acaagacggc ggcggatcca tggtgagcaa gggcgaggag   420
ctgttcaccg gggtggtgcc catcctggtc gagctggacg gcgacgtaaa cggccacaag   480
ttcagcgtgt ccggcgaggg cgagggcgat gccacctacg gcaagctgac cctgaagttc   540
atctgcacca ccggcaagct gcccgtgccc tggcccaccc tcgtgaccac cctgacctac   600
ggcgtgcagt gcttcagccg ctaccccgac cacatgaagc agcacgactt cttcaagtcc   660
gccatgcccg aaggctacgt ccaggagcgc accatcttct tcaaggacga cggcaactac   720
aagacccgcg ccgaggtgaa gttcgagggc gacaccctgg tgaaccgcat cgagctgaag   780
ggcatcgact tcaaggagga cggcaacatc ctggggcaca gctggagta caactacaac   840
agccacaacg tctatatcat ggccgacaag cagaagaacg gcatcaaggt gaacttcaag   900
atccgccaca catcgagga cggcagcgtg cagctcgccg accactacca gcagaacacc   960
cccatcggcg acggccccgt gctgctgccc gacaaccact acctgagcac ccagtccaag  1020
```

```
ctgagcaaag accccaacga gaagcgcgat cacatggtcc tgctggagtt cgtgaccgcc    1080
gccgggatca ctctcggcat ggacgagctg tacaagtaa                          1119
```

SEQ ID NO: 21          moltype = DNA   length = 882
FEATURE                Location/Qualifiers
source                 1..882
                       mol_type = other DNA
                       organism = synthetic construct
SEQUENCE: 21

```
atgggctcga ctcgcaagga aatcattgag aagttagaaa agagcctgcg tcgccagaag    60
aaactggcac gtttcctttt aatcttactt ttactgttgt tagctctgct gcttgaatta    120
ttggagcttt tgcgccgtct ggaagagttg cagcgtcgcg gctcaagtga cgaagaagtc    180
catgaattat tacgccgtat cattgagctt gtggaatata ttatccttct ggtgttgttc    240
atcatcgtac ttgtccgcat catcatcaaa ttagcagagc atcaacgccg cttggttgag    300
gaactgaaga agcaggacgg tagcagcgga tccatggaca aagattgcga aatgaaacgt    360
accaccctgg atagcccgct gggcaaactg gaactgagcg gctgcgaaca gggcctgcat    420
gaaattaaac tgctgggtaa aggcaccagc gcggccgatg cggttgaagt tccggccccg    480
gccgccgtgc tgggtggtcc ggaaccgctg atgcaggcga ccgcgtggct gaacgcgtat    540
tttcatcagc cggaagcgat tgaagaattt ccggttccgg cgctgcatca tccggtgttt    600
cagcaggaga gctttacccg tcaggtgctg tggaaactgc tgaaagtggt taaatttggc    660
gaagtgatta gctatcagca gctggcggcc ctggcgggta tccggcggc caccgccgcc    720
gttaaaaccg cgctgagcgg taacccggtg ccgattctga ttccgtgcca tcgtgtggtt    780
agctctagcg gtgcggttgg cggttatgaa ggtggtctgg cggtgaaaga gtggctgctg    840
gcccatgaag gtcatcgtct gggtaaaccg ggtctgggat aa                       882
```

SEQ ID NO: 22          moltype = DNA   length = 876
FEATURE                Location/Qualifiers
source                 1..876
                       mol_type = other DNA
                       organism = synthetic construct
SEQUENCE: 22

```
atgggcacca ggacagagat catcagggag cttgagcgat ccttgcgaga gcagcgcgtg    60
cttgctattt tcctcctggc gttgctcatc gtacttctct ggctgctgca acaacttaaa    120
gaattgttgc gcgagctgga acggctgcaa agagaaggtt catccgacga ggatgtaaga    180
gaattgctta gagaaatcaa agaacttgtt gagaacattg tatatctggt aataataatc    240
atggtcctcg tcctggtaat catagccctg gcaagaacgc aaaaatacct tgtcgaaagc    300
ctgaagcggc aggatggcgg cggatccatg gacaaagatt gcgaaatgaa acgtaccacc    360
ctggatagcc gctgggcaa actggaactg agcggctgcg aacagggcct gcatgaaatt    420
aaactgctgg gtaaaggcac cagcgcggcc gatgcggttg aagttccggc cccggccgtg    480
ctggttggtg gtccggaacc gctgatgcag gcgaccgcgt ggctgaacgc gtattttcat    540
cagccggaag cgattgaaga atttccggtt ccggcgctgc atcatccggt gtttcagcag    600
gagagcttta cccgtcaggt gctgtggaaa ctgctgaaag tggttaaatt tggcgaagtg    660
attagctatc agcagctggc ggccctggcg ggtaatccgg ttccgcaccg cgccgttaaa    720
accgcgctga gcggtaaccc ggtgccgatt ctgattccgt gccatcgtgt ggttagctct    780
agcggtgcgg ttgcgggtta tgaaggtggt ctggcggtga aagagtggct gctggcccat    840
gaaggtcatc gtctgggtaa accgggtctg ggataa                              876
```

SEQ ID NO: 23          moltype = DNA   length = 873
FEATURE                Location/Qualifiers
source                 1..873
                       mol_type = other DNA
                       organism = synthetic construct
SEQUENCE: 23

```
atgactagga cggagattat aactaggctc tctttttctc ttttgttgca gctcgtgctc    60
gctatatttc tccttgctct tctgatagtc cttcttgttc tgcttatcta tttgaaggaa    120
cttctccgcg agttggagcg actccagagg gaggggtcaa gcgacgaaga tgtacgagaa    180
ttgttgcgcg aaattaaatg gttggtaatt gtgattgtgg ctctcgtaat cattataatg    240
gtcttggtat tggtaatcat cgctcttgct gtgttgcaaa tgtacctcgt tcgcgaactg    300
aaacggcagg atggcggcgg atccatggac aaagattgcg aaatgaaacg taccaccctg    360
gatagcccgc tgggcaaact ggaactgagc ggctgcgaac agggcctgca tgaaattaaa    420
ctgctgggta aaggcaccag cgcggccgat gcggttgaag ttccggcccc ggccgccgtg    480
ctgggtggtc cggaaccgct gatgcaggcg accgcgtggc tgaacgcgta ttttcatcag    540
ccggaagcga ttgaagaatt tccggttccg gcgctgcatc atccggtgtt tcagcaggag    600
agctttaccc gtcaggtgct gtggaaactg ctgaaagtgg ttaaatttgg cgaagtgatt    660
agctatcagc agctggcggc cctggcgggt aatccggcgg ccaccgccgc cgttaaaacc    720
gcgctgagcg gtaacccggt gccgattctg attccgtgcc atcgtgtggt tagctctagc    780
ggtgcggttg cggttatgaa aggtggtctg gcggtgaaag agtggctgct ggcccatgaa    840
ggtcatcgtc tgggtaaacc gggtctggga taa                                 873
```

SEQ ID NO: 24          moltype = DNA   length = 918
FEATURE                Location/Qualifiers
source                 1..918
                       mol_type = other DNA
                       organism = synthetic construct
SEQUENCE: 24

```
atggtgctgt ctcatcattt tggcaaagaa ttcgctagcg ccaccatgac ccgcacggag    60
attatcacca ggctcagttt ttcccttttg ttgcaacttg tcttggcaat ttttttgctc    120
gcactgctga tcgtactctt ggtgcttttg atagttctga tgattctcct tatagcgttg    180
gaatatcttc aaaaagaggg atcttcagat gaggatgtga agaactcct ggtgctcata    240
```

-continued

```
atgatttttgg tgatagtgat tgttgccctg gtaattataa tcatggtact ggtcctcgtt   300
ataatcgctc tggctgtgtt gcagatgtac ctggttcggg aactcaagcg acaagacggc   360
ggcggatcca tggacaaaga ttgcgaaatg aaacgtacca ccctggatag cccgctgggc   420
aaaactggaac tgagcggctg cgaacagggc ctgcatgaaa ttaaactgct gggtaaaggc   480
accagcgcgg ccgatgcggt tgaagttccg gccccggccg ccgtgctggg tggtccggaa   540
ccgctgatgc aggcgaccgc gtggctgaac gcgtattttc atcagccgga agcgattgaa   600
gaatttccgg ttccggcgct gcatcatccg gtgtttcagc aggagagctt tacccgtcag   660
gtgctgtgga aactgctgaa agtggttaaa tttggcgaag tgattagcta tcagcagctg   720
gcggccctgg cgggtaatcc ggcggccacc gccgccgtta aaaccgcgct gagcggtaac   780
ccggtgccga ttctgattcc gtgccatcgt gtggttagct ctagcggtgc ggttggcggt   840
tatgaaggtg gtctggcggt gaaagagtgg ctgctggccc atgaaggtca tcgtctgggt   900
aaaccgggtc tgggataa                                                 918
```

```
SEQ ID NO: 25            moltype = DNA   length = 654
FEATURE                  Location/Qualifiers
source                   1..654
                         mol_type = other DNA
                         organism = synthetic construct
SEQUENCE: 25
atgagtgccg aggaactgct gcgtcgttcg cgcgaatatc ttaagaaggt tgctaagttt   60
caacttgtga tcgcactcgt attccttatc ctgctggaaa tcctttcgcg ccgtagcgag   120
gagctgatcc gtgaattaga agagaaaggc gcagcctcag ggccccgcatg   180
aaacaacaac acatgactgc ctacctgcaa gccgcgttaa ccgcctggga gatcatcagc   240
aagagcctca tcgccctgtt attactccag cagaatcagc tcaatctgga acttaacacg   300
gatacagaca agaacgtagc cgaggagtta cttcgtcgta gccgtgagta tcttaagaag   360
gtggcgaaga agcaactggt tattgctttt gtattcctca tcttgctcga gattttaagc   420
cgccgtagtg aggagttaat tcgtgagtta gaggagaagg gcgcggcgtc ggaagccgaa   480
ttggctcgca tgaagcaaca acacatgacc gcctatttgc aggcagcgct gactgcctgg   540
gagatcattt ccaaatcttt aatcgcgctc ctgcttctgc aacagaatca actgaatctc   600
gagctccgcc atggcggatc cgggagcgac tacaaagacg atgacgataa gtaa          654
```

```
SEQ ID NO: 26            moltype = DNA   length = 654
FEATURE                  Location/Qualifiers
source                   1..654
                         mol_type = other DNA
                         organism = synthetic construct
SEQUENCE: 26
atgtccgccg aggagttact gcgccgttcc cgcgagtact taaagaaggt cgctaaaatt   60
cagctggtta ttgctctcgt cttcttgatc cttctcatca ttttgtcccg ccgtagcgag   120
gaactcatcc gcgaactcga ggagaaggc gccgccagcg aggccgagtt ggcccgcatg   180
aagcaacaac acatgacggc gtatttgcag gccgcgttga ctgcttggga aatcatctca   240
aaatctgtta ttgctctgtt acttttgcaa cagaatcaat taaatttgga gcttaatacc   300
gacaccgaca agaatgtggc tgaggagtta ttacgccgct cacgtgagta tctgaagaag   360
gtagcaaaga tccagttagt tatcgcctc gtgttcctta ttcttctgat catttttaagc   420
cgtcgctcag aggagctgat tcgtgagctt gaagaaaagg gagcggcttc agaagcggaa   480
ctggcccgta tgaagcaaca gcacatgacg gcatatcttc aggccgcgtt aacggcttgg   540
gagattattt caaagagtcg catcgcattg cttctgttac aacaaaatca gttgaacctg   600
gagctccgtc acggtggatc cgggtcagac tataaagatg atgacgacaa gtaa          654
```

```
SEQ ID NO: 27            moltype = DNA   length = 654
FEATURE                  Location/Qualifiers
source                   1..654
                         mol_type = other DNA
                         organism = synthetic construct
SEQUENCE: 27
atgtcagccg aggagttgct gcgtcgctct cgcaagtact taattttggt ggctttgatt   60
caactggtga tcgccttcgt tttcctcatt cttctgattc ttttgagctg gctctcatgg   120
ctgttaattc gtgagctcga ggagaaaggg gcagcgagcg aggctgagtt ggcgcgcatg   180
aagattcaga tgatgactgc ctatctgcag gccgcgctga ccgcctggga gatcattgtt   240
aaagccgtta ttgccttgct cctgctccgc caaaatcaac tgaatcttga gctcaacact   300
gacacagaca agaatgtggc agaggagctt ctccgtcgta gccgcaagta cttaatcatt   360
gtggccttaa ttcagttggt aatcgcattc gtctttctga tcctgttaat cttgctttca   420
tggaagtcgt gggagctgat tcgcgagctt gaagagaagg gcgccgcctc ggaagccgaa   480
ctcgctcgta tgaagatgca agtgatgtta gcctatctcc aagcagctct gaccgcttgg   540
gaaattattg cgaagtcagt aattgcgtta ttacttctcc tgcaaaacca attaaacctg   600
gagctgcgcc acggcggatc cggaagtgac tacaaggatg acgatgacaa gtaa          654
```

```
SEQ ID NO: 28            moltype = DNA   length = 654
FEATURE                  Location/Qualifiers
source                   1..654
                         mol_type = other DNA
                         organism = synthetic construct
SEQUENCE: 28
atgtctgctg aggagttgtt acgttggagc cgcatttatt tagtcatcgt ggccttaatc   60
cagttggtta tcgctttcgt attccttatt ttgctcatct tgctgtcctg gctttcatta   120
gtgctcatct gggagttaga ggagaaggc gctgcaagtg aggcggagct tgcgcgcatg   180
attctccagg tcatgacggc gtacttgcaa gcagcctaa ctgcgtggga gattatcgca   240
aaggtcgtaa ttgccctgct cctgcttgtg gttaaccagc ttaatctcga gctgaacacg   300
gacacagata agaacgtcgc cgaggagctg ttacgccgtt cccttttgta tctgatcatg   360
```

-continued

```
gtagccctca ttcaattagt cattgcattc gtattcctta tcttgttaat tctcttgagc    420
tggatctcgc ttctgcttat ctgggaactc gaggaaaagg gcgctgcgag cgaagcagag    480
ctcgcccgta tggcgatcca attaatgatt gcttatctcc aagcggccct gaccgcatgg    540
gagatcattg caaagagcgt catcgccttg cttcttctca tcttaaatca actgaatctt    600
gaactgcgtc acgaggatc cggtagtgac tacaaggacg acgacgacaa gtaa           654
```

```
SEQ ID NO: 29          moltype = DNA   length = 1200
FEATURE                Location/Qualifiers
source                 1..1200
                       mol_type = other DNA
                       organism = synthetic construct
SEQUENCE: 29
atgggctcga ctcgcaagga aatcattgag aagttagaaa agagcctgcg tcgccagaag     60
aaactggcac gtttcctttt aatcttactt ttactgttgt tagctctgct gcttgaatta    120
ttggagcttt tgcgccgtct ggaagagttg cagcgtcgcg gctcaagtga cgaagaagtc    180
catgaattat tacgccgtat cattgagctt gtggaatata ttatccttct ggtgttgttc    240
atcatcgtac ttgtccgcat catcatcaaa ttagcagagc atcaacgccg cttggttgag    300
gaactgaaga agcaggacgg tagcagcgga tccgcaagtc cggcagcacc ggcaccggca    360
tcaccagctg caccagcacc tagtgcaccg gcaggcggta ttctgtggca tgaaatgtgg    420
cacgaaggtc tggaagaagc aagccgtctg tattttggtg aacgtaatgt gaaaggcatg    480
tttgaagttc tggaaccgct gcatgcaatg atggaacgtg gtccgcagac actgaaagaa    540
accagcttta atcaggccta tggtcgtgat ctgatggaag cacaagaatg gtgtcgcaaa    600
tacatgaaaa gcggtaacgt taaagatctg ctgcaggcat gggatctgta ttatcatgtt    660
tttcgtcgca ttagcaaagg tggtagcggt ggtggtggtt ctggtggtag cagctcaggt    720
ggtgtttta ccctggaaga ttttgttggt gattgggaac agaccgcagc atataatctg    780
gatcaggtgc tggaacaagg tggtgtgagc agcctgctgc agaatctggc agttagcgtt    840
accccgattc agcgtattgt tcgtagcggt gaaaatgccc tgaaaattga tattcatgtg    900
atcatcccgt atgaaggtct gagcgcagat cagatggcac agattgaaga agtgttcaaa    960
gttgtttatc cggtggatga ccaccatttt aaagttattc tgccgtatgg caccctggtt   1020
attgatggtg tgaccccgaa tatgctgaat tatttcggtc gtccttatga aggtattgcc   1080
gtttttgatg gcaaaaaaat caccgttacc ggtacactgt ggaacggtaa caaaattatc   1140
gatgaacgtc tgattacacc ggatggtagc atgctgtttc gtgttaccat taacagctaa   1200
```

```
SEQ ID NO: 30          moltype = DNA   length = 837
FEATURE                Location/Qualifiers
source                 1..837
                       mol_type = other DNA
                       organism = synthetic construct
SEQUENCE: 30
atggtgctgt ctcatcattt tggcaaagaa ttcgctagcg ccaccatgac ccgcacggag     60
attatcacca ggctcagttt ttccctttg ttgcaacttg tcttggcaat tttttttgctc    120
gcactgctga tcgtactctt ggtgcttttg atagttctga tgattctcct tatagcgttg    180
gaatatcttc aaaaagaggg atcttcagat gaggatgtga aagaactcct ggtgctcata    240
atgatttttgg tgatagtgat tgttgccctg gtaattataa tcatggtact ggtcctcgtt    300
ataatcgctc tggctgtgtt gcagatgtac ctggttcggg aactcaagcg acaagacggc    360
ggcggatccg caagtccggc agcaccggca ccggcatcac cagctgcacc agcacctagt    420
gcaccggcag gcggtggtgt tcaggttgaa accattagtc ctggtgatgg tcgtaccttt    480
ccgaaacgtg gtcagacctg tgttgttcat tacaccggta tgctggaaga tggcaaaaaa    540
ttcgatagca gccgtgatcg taataagccg tttaaattca tgctgggtaa acaagaagtt    600
attcgcggtt gggaagaggg tgttgcacag atgagcgttg gtcagcgtgc aaaactgacc    660
atttcaccgg attatgccta tggtgcaacc ggtcatccgg gtattattcc gcctcatgca    720
accctggttt ttgatgttga actgctgaaa ctggaaggtg gtagcggtgg tggtggttct    780
ggtggtagca gctcaggtgg tgttaccggt tatcgtctgt ttgaagaaat tctgtaa       837
```